US010222337B1

(12) United States Patent
Yoo et al.

(10) Patent No.: US 10,222,337 B1
(45) Date of Patent: *Mar. 5, 2019

(54) LASER ABLATION ANALYSIS TECHNIQUES

(71) Applicant: Applied Spectra, Inc., Fremont, CA (US)

(72) Inventors: Jong Hyun Yoo, Milpitas, CA (US); Chunyi Liu, Fremont, CA (US); Alexander A. Bol'shakov, Hayward, CA (US); Richard E. Russo, Walnut Creek, CA (US); Xianglei Mao, Castro Valley, CA (US); Randolph S. Tribe, San Jose, CA (US); Osman Sorkhabi, San Ramon, CA (US)

(73) Assignee: Applied Spectra, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/488,422

(22) Filed: Apr. 14, 2017

Related U.S. Application Data

(63) Continuation-in-part of application No. 15/201,494, filed on Jul. 3, 2016, which is a continuation of
(Continued)

(51) Int. Cl.
*G01J 3/30* (2006.01)
*G01N 21/71* (2006.01)
(Continued)

(52) U.S. Cl.
CPC ......... *G01N 21/718* (2013.01); *B23K 26/048* (2013.01); *H01J 49/0468* (2013.01); *H01J 49/105* (2013.01)

(58) Field of Classification Search
CPC .. G01J 3/443; G01J 3/30; G01J 3/4338; G01J 3/10; B23K 26/03; B23K 26/04;
(Continued)

(56) References Cited

U.S. PATENT DOCUMENTS 4,668,860 A  5/1987 Anthon
5,627,641 A  5/1997 Mauchien
(Continued)

FOREIGN PATENT DOCUMENTS

WO   WO/2012087405   6/2012

OTHER PUBLICATIONS

B.W. Smith, I.B. Gornushkin, L.A. King, J.D. Winefordner, "A laser ablation—atomic fluorescence technique for isotopically selective determination of lithium in solids", Spectrochimica Acta Part B: Atomic Spectroscopy (1998), 53(6-8), pp. 1131-1138.
(Continued)

*Primary Examiner* — Jamil Ahmed
(74) *Attorney, Agent, or Firm* — Microtechnology Law & Analysis; Daniel L. Flamm

(57) ABSTRACT

Methods for laser induced ablation spectroscopy are disclosed. A position sensor, and position motors can move a sample stage in three independent spatial coordinate directions, and a stage position control circuit can move an analysis sample site to selected coordinate positions for ablation. Light from laser ablation can be gathered into a lightguide fiber bundle that is subdivided into branches. One branch can convey a first portion of the light to a broadband spectrometer operable to analyze a relatively wide spectral segment, and a different branch can convey a second portion of the light to a high dispersion spectrometer operable to measure minor concentrations and/or trace elements. Emissions can be simultaneously analyzed in various ways using a plurality of spectrometers having distinct and/or complementary capabilities, and isotope analysis of a sample can be performed.

20 Claims, 31 Drawing Sheets

Related U.S. Application Data application No. 13/492,923, filed on Jun. 10, 2012, now Pat. No. 9,383,260, which is a continuation-in-part of application No. 12/435,970, filed on May 5, 2009, now Pat. No. 8,199,321, application No. 15/488,422, which is a continuation-in-part of application No. 13/835,582, filed on Mar. 15, 2013, now abandoned, which is a continuation-in-part of application No. PCT/US2011/054994, filed on Oct. 5, 2011.

(60) Provisional application No. 61/126,633, filed on May 5, 2008, provisional application No. 61/390,117, filed on Oct. 5, 2010.

(51) Int. Cl.
- *B23K 26/04* (2014.01)
- *H01J 49/04* (2006.01)
- *H01J 49/10* (2006.01)

(58) Field of Classification Search
CPC  B23K 26/032; B23K 26/048; B23K 26/0861; G01N 21/63; G01N 21/718; H01J 49/0468; G06F 19/00
See application file for complete search history.

(56) References Cited

U.S. PATENT DOCUMENTS

| | | | |
|---|---|---|---|
| 5,715,053 A | 2/1998 | Loge | |
| 6,407,811 B1 | 6/2002 | Snyder | |
| 6,426,226 B1 | 7/2002 | Senkan | |
| 6,771,368 B1 * | 8/2004 | Chadwick | G01N 21/718 356/317 |
| 7,566,881 B2 | 7/2009 | Parvin | |
| 7,663,749 B2 * | 2/2010 | Levesque | G01N 21/718 356/318 |
| 8,010,306 B2 | 8/2011 | Wang | |
| 8,199,321 B2 | 6/2012 | Yoo | |
| 9,061,369 B2 | 6/2015 | Yoo | |
| 9,383,260 B1 | 7/2016 | Yoo | |
| 2005/0176012 A1 | 8/2005 | Wozny et al. | |
| 2006/0180581 A1 * | 8/2006 | Swaringen | B23K 26/04 219/121.83 |
| 2007/0046934 A1 * | 3/2007 | Roy | G01J 3/4338 356/318 |
| 2013/0267035 A1 | 10/2013 | Russo et al. | |

OTHER PUBLICATIONS

L.A. King, I.B. Gornushkin, D. Pappas, B.W. Smith, J.D. Winefordner, "Rubidium isotope measurements in solid samples by laser ablation—laser atomic absorption spectroscopy", Spectrochimica Acta Part B: Atomic Spectroscopy (1999), 54(13), pp. 1771-1781.

B.W. Smith, A.Quentmeier, M. Bolshov, K. Niemax, "Measurement of uranium isotope rations in solid samples using laser ablation and diode laser-excited atomic fluorescence spectrometry", Spectrochimica Acta Part B: Atomic Spectroscopy (1999), 54(6), pp. 943-958.

E.H. Evans, J.A. Day, C.D. Palmerc, C.M.M. Smith, "Atomic Spectrometry Update. Advances in atomic spectrometry and related techniques", Journal of Analytical Atomic Spectrometry (2009), 24, pp. 711-733.

H. Niki, S. Kataoka, I. Kitazima, "Measurement Technique of Boron Isotopic Ratio by Laser-induced Breakdown Spectroscopy", Journal Of Nuclear Science And Technology (1998), 35(1), pp. 34-39.

F. Melen, I. Dubois, H. Bredohl, "The A-X and B-X transitions of BO", J. Phys. B: At. Mol. Phys. (1985), 18, pp. 2423-2432.

J.G. Phillips, S.P. Davis, "The Singlet Pi-singlet Sigma system of zirconium oxide", Astrophysical Journal Supplement Series (1976), 32, pp. 537-581.

R.E. Russo, A.A. Bol'Shakov, X. Mao, C.P. Mckay, D.L. Perry, O. Sorkhabi, "Laser Ablation Molecular Isotopic Spectrometry", Spectrochimica Acta Part B (2011), 66, pp. 99-104.

J.L. Gottfried, F.C. De Lucia, C.A. Munson, A.W. Miziolek, "Double-pulse standoff laser-induced breakdown spectroscopy for versatile hazardous materials detection", Spectrochimica Acta, Part B (2007), 62, pp. 1405-1411.

J. González, C. Liu, J. Yoo, X. Mao, R.E. Russo, "Double-pulse laser ablation inductively coupled plasma mass spectrometry", Spectrochimica Acta Part B (2005), 60, pp. 27-31.

X. Mao, A. A. Bol'shakov, D. L. Perry, O.Sorkhabi, R. E. Russo, "Laser Ablation Molecular Isotopic Spectrometry: Parameter influence on boron isotope measurements", Spectrochimica Acta Part B (2011), 66, pp. 604-609.

X. Mao, A.A. Bol'shakov, I. Choi, C.P. Mckay, D. L. Perry, O. Sorkhabi, R. E. Russo, "Laser Ablation Molecular Isotopic Spectrometry: Strontium and its isotopes", Spectrochimica Acta Part B (2011), 66, 767-775.

A.A. Bol'shakov, X. Mao, D.L. Perry, R.E. Russo, "Laser Ablation Molecular Isotopic Spectrometry for rare isotopes of the light elements", Spectroscopy, (2014), 29, No. 6, pp. 30-39.

A.A. Bol'shakov, X. Mao, J. Jain, D.L. Mcintyre, R.E. Russo, "Laser ablation molecular isotopic spectrometry of carbon isotopes", Spectrochimica Acta, Part B.(2015), 113, pp. 106-112.

A.A. Bol'shakov, X. Mao, J.J. Gonzalez, R.E. Russo, "Laser ablation molecular isotopic spectrometry (LAMIS): current state of the art", Journal of Analytical Atomic Spectrometry, (2016), 31, pp. 119-134.

A. K. Carlson "Lead Isotope Analysis of Human Bone for Addressing Cultural Affinity: a Case Study from Rocky Mountain House", Alberta Journal of Archaeological Science (1996) 23, 557-567.

L. Pillonel,R. Badertscher, P. Froidevaux, G. Haberhauer, S. Holzl, P. Horn, "Stable isotope ratios, major trace and radioactive elements in emmental cheeses of different origins", Lebensmittel-Wissenschaft und-Technologie—Food Science and Technology, (2003), 36(6), 615-623.

T. C. Schmidt, L. Zwank, M. Elsner, M. Berg, R. U. Meckenstock, S. B. Haderlein "Compund-specific stable isotope analysis of organic contaminants in natural environments: a critical review of the state of the art, prospects, and future challenges", Analytical and Bioanalytical Chemistry (2004), 378, 283-300.

A. Rossmann, F. Reniero, I. Moussa, H. L. Schmidt, G. Versini, M. H. Merle, "Stable oxygen isotope content of water of EU data-bank wines from Italy, France and Germany", Zeitschrift fur Lebensmittel-Untersuchung und-Forschung A—Food Research and Technology, (1999), 208(5-6), 400-407.

H. P. Balling, A. Rossmann "Countering fraud via isotope analysis—Case report", Kriminalistik (2004), 58(1), 44-47.

A. Moreda-Pineiro, A. Marcos, A. Fisher, S. J. Hill "Evaluation of the effect of data pre-treatment procedures on classical pattern recognition and principal components analysis: A case study for the geographical classification of tea", Journal of Environmental Monitoring, (2001), 3(4), 352-360.

A. Moreda-Pineiro, A. Fisher, S. J. Hill "The classification of tea according to region of origin using pattern recognition techniques and trace metal data", Journal of Food Composition and Analysis (2003), 16(2), 195-211.

W. A. Simpkins, G. Patel, M. Harrison, D. Goldberg "Stable carbon isotope ratio analysis of Australian orange juices", Food Chemistry (2000), 70(3), 385-390.

A. Kawasaki, H. Oda, T. Hirata "Determination of strontium isotope ratio of brown rice for estimating its provenance", Soil Science and Plant Nutrition (2002), 48(5), 635-640.

M. Barbaste, L Halicz, A. Galy, B. Medina, H. Emteborg, F. C. Adams "Evaluation of the accuracy of the determination of lead isotope ratios in wine by ICP MS using quadrupole, multicollector magnetic sector and time-of-light analyzers", Talanta (2001), 54(2), 307-317.

V. Krivan, P. Barth, A. F. Morales "Multielement analysis of green coffee and its possible use for the determination of origin", Mikrochimica Acta (1993), 110,217-236.

(56) References Cited

OTHER PUBLICATIONS

M.P. Day, B.L. Zhang, G.J. Martin "The use of traceelement data to complement stable-isotope methods in the characterization of grapemusts", American Journal of Enology and Viticulture (1994), 45, 79-85.

S.J. Haswell, A.D. Walmsley "Multivariate data visualisation methods based on multi-elemental analysis of wines and coffees using total reflection X-ray fluorescence analysis", Journal of Analytical Atomic Spectrometry (1998), 13 (2), 131-134.

N.A. Zakorina, G.S. Lazeeva, A.A. Petrov, Spectroscopic determination of the isotopic composition of boron trifluoride, Atomnaya Energiya, (1966) 20,348-351. English translation: Journal of Nuclear Energy, (1967), 21, 309-313.

N.A. Zakorina, A.A. Petrov, Isotopic spectral analysis of oxygen in a hot hollow cathode, Journal of Applied Spectroscopy, (1975), 23, 1157-1160.

G.S. Lazeeva, A.A. Petrov, R.V. Khomyakov, Spectral-isotope method for determining carbon in biological objects, Journal of Applied Spectroscopy, (1976), 25, 1199-1205.

G.S. Lazeeva, V.M. Nemets, A.A. Petrov, Spectral-isotopic method of determination of gas-forming elements in organic and inorganic substances, Spectrochimica Acta Part B, (1981), 36, 1233-1242.

V.M. Nemets, I.A. Rodushkin, A.A. Solov'ev, V.N. Funtov, Isotopic carbon analysis using the C2 molecule spectrum, Journal of Applied Spectroscopy, (1990), 52, 461-465.

Y.-K. Xiao, E.S. Beary, J.D. Fassett, An improved method for the high-precision isotopic measurement of boron by thermal ionization mass spectrometry, Int. J. Mass Spectrom. Ion Process., 85 (1988) 203-213.

L. Mercadier, J. Hermann, C. Grisolia, A. Semerok, Plume segregation observed in hydrogen and deuterium containing plasmas produced by laser ablation of carbon fiber tiles from a fusion reactor, Spectrochim. Acta Part B, '2010), 65, 715-720.

D. Vukanovic, V. Vukanovic, "On the behaviour of hydrogen isotopes in a d.c. arc plasma", Spectrochimica Acta Part B, (1969), 24, 579-583.

L. St-Onge, R. Sing, S. Béchard, M. Sabsabi, Applied Physics A, (1999), 69, Suppl. 1, S913-S916.

L.J. Moore, T J. Murphy, I.L. Barnes, P.J. Paulsen, Absolute isotopic abundance ratios and atomic weight of a reference sample of strontium, J. of Res. (NBS) 87 (1982) 1-8.

I.T. Platzner, K. Habfast, A.J. Walder, A. Goetz, Modern isotope ratio mass spectrometry. Wiley, London, 1997, 514 p.

R. C. Stern, B. B. Snavely, "The Laser Isotope Separation Program at Lawrence Livermore Laboratory", Annals of the New York Academy of Sciences, (1976), 267, 71-79.

\* cited by examiner

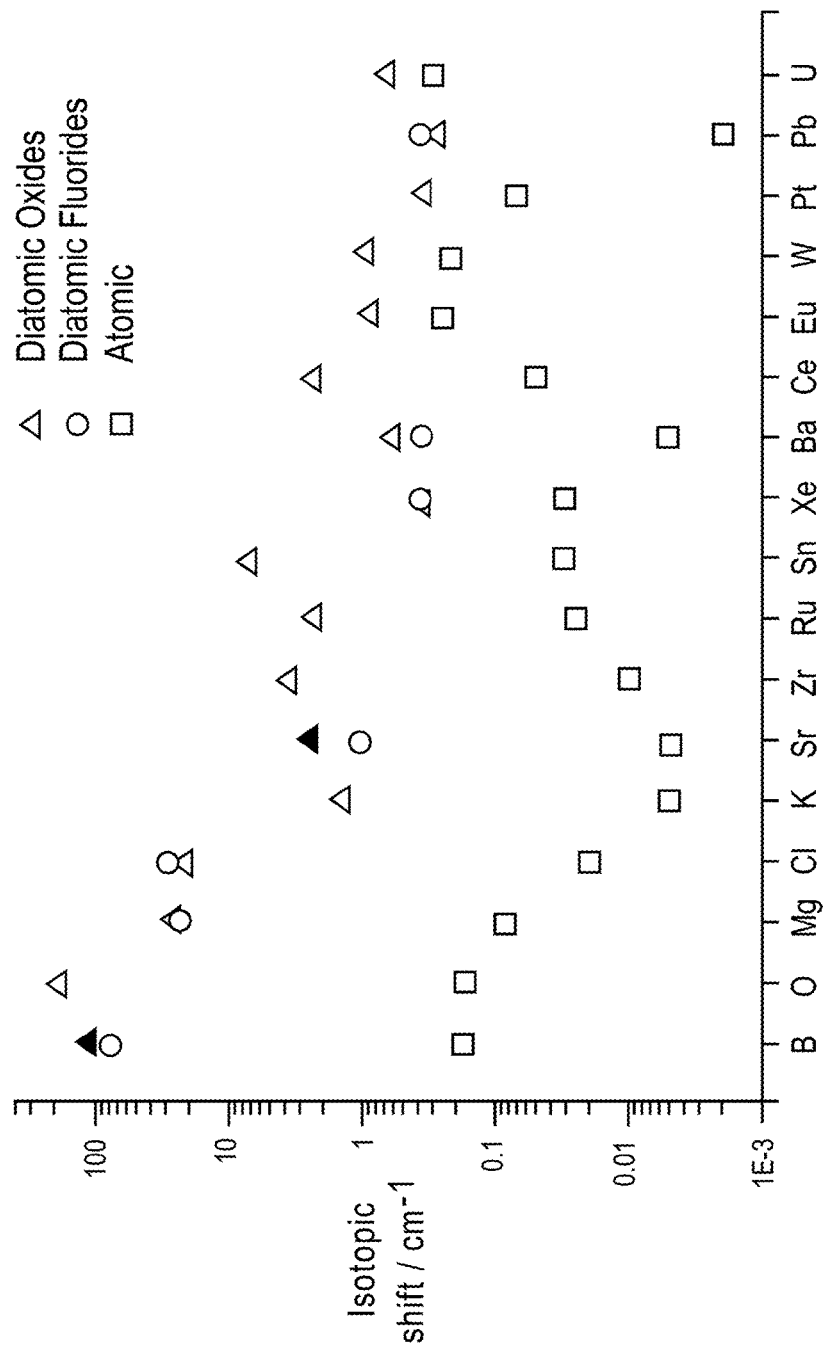

LASER ABLATION ANALYSIS TECHNIQUES

CROSS-REFERENCES TO RELATED APPLICATIONS

This present application is a continuation-in-part of co-pending application U.S. patent application Ser. No. 15/201,494 filed Jul. 3, 2016, which is a continuation of U.S. patent application Ser. No. 13/492,923 filed Jun. 10, 2012, which is a continuation-in-part of U.S. patent application Ser. No. 12/435,970 filed May 5, 2009 which claims the benefit of U.S. Provisional Application No. 61/126,633 filed May 5, 2008; and is a continuation-in-part of co-pending U.S. patent application Ser. No. 13/835,582 filed Mar. 15, 2013, which is a continuation-in-part of International Application No. PCT/US2011/054994, filed Oct. 5, 2011, which claims priority to U.S. Provisional Application No. 61/390,117, filed Oct. 5, 2010, all of which are hereby incorporated by reference in their entirety for all purposes.

FIELD OF THE INVENTION

The present disclosure relates generally to the art of chemical analysis, and more particularly relates to improved apparatus and methods for monitoring the composition of a substrate using spectroscopies based on laser induced ablation.

BACKGROUND

Restriction of hazardous substances by statutes such as the Directive on the Restriction of the Use of Certain Hazardous Substances in Electrical and Electronic Equipment 2002/95/EC (commonly referred to as the Restriction of Hazardous Substances Directive or RoHS) was adopted in February 2003 by the European Union. The state of California has passed a similar law. The directive restricts the use of six hazardous materials in the manufacture of various types of electronic and electrical equipment. The six hazardous materials include Lead, Mercury, Cadmium, Hexavalent chromium (Cr-VI or Cr6+), Polybrominated biphenyls (PBB), and Polybrominated diphenyl ether (PBDE).

Industry seeks efficient and economical measures to comply with RoHS. Dissolution in acid is commonly used to test and measure compositional qualities of sample material. This method has inherent disadvantages. Laser induced breakdown optical emission spectroscopy (LIBS) as well as other laser spectrometry methods are potentially efficient and economical techniques to determining and/or verify the composition of products and other materials.

Isotopic analysis of sample composition can provide important information, particularly in the fields of archaeology, ecology, nuclear forensics, geology, hydrology, paleoclimatology, and national security, among others. Isotopic analysis has typically been done using techniques gas chromatography/mass spectrometry (GC/MS), time of flight mass spectrometry (TOF-MS), or inductively coupled plasma mass spectrometry (ICP/MS). Mass spectrometry (MS) is a powerful technique for isotopic analysis owing to its ability to discriminate ions based on mass to charge ratio. MS techniques can also be quite sensitive. However, these measurements often require time consuming counting and/or complex chemical digestion procedures for the mass spectrometric analysis. In general, mass spectrometric analyses must be performed in a vacuum, have low throughput, and require a gaseous sample.

Various other techniques that have been used for isotopic analysis include inductively coupled plasma-atomic emission spectroscopy, atomic absorption spectroscopy, and gas chromatography-atomic absorption spectroscopy. Each of these techniques has serious limitations and many of them require extensive sample preparation and/or dissolution in a liquid prior to analysis.

The LIBS type of spectrometry has been an unreliable and inexact measurement system since there is a large variation in the recorded data. A major source of variability has been inconsistent plasma plume generation by the pulse laser. Former LIBS type analyses have been unsuccessful in matching known standards achieved with other analysis methods.

SUMMARY

In a first aspect of the present disclosure, a laser ablation spectroscopy apparatus is provided. A pulsed laser is focused on a sample site to generate a plasma plume during a laser ablation process. The plasma plume can be detected with an optical spectrometer having an intensified charge coupled device. A sample of material is coupled to a stage movable in independent x, y and z directions using an array of x-y-z motors. A change in the height of the sample is detected using a sensor. Preferably, the sensor is a triangulation sensor. The apparatus includes a system computer for synchronizing the movement of the stage in the x, y and z direction during the laser ablation process. The height of the sample site can be automatically adjusted following each laser ablation. In one embodiment, the system computer includes a controller, application software and a graphical user interface (GUI).

In another aspect of the present disclosure, a method of laser ablation spectroscopy is provided. The method includes a protocol of generating one or more laser ablations to a sample site. The spectral data of the individual laser ablation sites can be used to form a chemical map of the sample surface or the total number of laser ablations for the sites can be averaged together. In some embodiments, the total number of laser ablations for a sample site equals three laser ablations. The protocol includes laser ablating additional sample sites and averaging the spectral data of the total number of sample sites. In some embodiments, there can be more than 2000 sample sites.

Further aspects disclosed herein provide apparatus for and methods of performing isotopic analysis on a sample. Methods disclosed herein can measure isotope splitting and isotope abundance ratios in laser plasmas at atmospheric pressure. Methods disclosed herein also can measure the isotope splitting and isotope abundance ratio from molecular species that exist and/or are formed from atoms and ions in the plasma.

An innovative aspect of the subject matter described in this disclosure can be implemented a method including (a) applying laser energy to a region of a sample with a laser to generate a plasma, and (b) recording a spectrum generated by a plurality of molecular species in the plasma with a device. In some embodiments, the sample is in a solid phase, a liquid phase, or a gas phase. In some embodiments, the plurality of molecular species is selected from the group consisting of oxides, nitrides, halides, excimers, diatoms, and combinations thereof.

There are embodiments where, the method further includes after operation (a), allowing the plasma to react with species in the surrounding environment to form the plurality of molecular species. In some embodiments, the method further includes after operation (a), allowing species atomized from the sample to react with each other to form the plurality of molecular species.

In some embodiments, operation (a) includes a process selected from the group consisting of ablating the sample with the applied laser energy, vaporizing the sample with the applied laser energy, desorbing the sample with the applied laser energy, and applying the laser energy in a pulse of the laser energy. As well, in some embodiments operation (a) includes applying a first pulse of laser energy at a first angle with respect to the sample and applying a second pulse of laser energy at a second angle with respect to the first angle.

In some embodiments, operation (b) is selected from the group consisting of recording the spectrum with visible spectroscopy, recording the spectrum with ultraviolet spectroscopy, recording the spectrum with infrared spectroscopy, recording the spectrum with near-infrared spectroscopy, recording the spectrum with terahertz spectroscopy, recording the spectrum with microwave spectroscopy, recording direct optical emission of the plurality of molecular species, recording optical absorption of the plurality of molecular species, recording induced fluorescence of the plurality of molecular species, recording Raman scattering of the plurality of molecular species, recording luminescence of the plurality of molecular species, recording phosphorescence of the plurality of molecular species, recording photoacoustics of the plurality of molecular species, and recording photoionization of the plurality of molecular species.

In various aspects, the method further includes (c) quantifying the abundance of isotopes of an element in the sample. In some embodiments, the method further includes performing operations (a), (b), and (c) on an additional region of the sample. In some embodiments, operation (c) includes generating a simulated spectrum for each of the plurality of molecular species with a mathematical model, performing a numerical fitting of the simulated spectrum of each of the plurality of molecular species to the recorded spectrum, and determining the abundance of the isotopes of the element in the sample from the result of the numerical fitting.

There are aspects where a specific period of time between operations (a) and (b) increases the intensity of the spectrum generated by the plurality of molecular species in the plasma and decreases the intensity of atomic emission and ionic emission. In some embodiments, the specific period of time depends on a wavelength of the laser energy, a pulse duration of the laser energy, a power of the laser energy, a spot size of the laser energy, and a fluence of the laser energy.

In some embodiments, operations (a) and (b) are performed in ambient air under ambient pressure. In some embodiments, operations (a) and (b) are performed in a chamber. In some embodiments, operations (a) and (b) are performed in a chamber, the chamber containing a specific gas at a specific pressure.

In some embodiments, the method further includes prior to operation (b), exciting the plasma with an additional energy source. In some embodiments, the additional energy source is selected from the group consisting of a microwave field, a radio frequency field, and additional laser energy.

Yet another aspect of the subject matter described in this disclosure can be implemented with a method including (a) applying laser energy to a sample in a first chamber with a laser to generate a first plasma that reacts to form species, (b) transferring the species from the first chamber to a second chamber, (c) imparting energy to the species in the second chamber to form a second plasma, and (d) recording a spectrum generated by a plurality of molecular species in the second plasma in the second chamber with a device.

Further aspects of the method include exciting the second plasma with an additional energy source in the second chamber. In some embodiments, the method further includes exciting the first plasma with an additional energy source in the first chamber.

There is an aspect that can be implemented with an apparatus including a sample holder configured to hold a sample, a laser, an emission collection system, and a spectrometer coupled to a detector. The apparatus also includes a system controller configured to execute instructions so that the apparatus will perform a method including applying laser energy to a region of a sample with the laser to generate a plasma and recording a spectrum generated by a plurality of molecular species in the plasma using the emission collection system and the spectrometer coupled to the detector.

Other features will become apparent from consideration of the following description taken in conjunction with the accompanying drawings.

BRIEF DESCRIPTION OF DRAWINGS

Various embodiments are illustrated in an exemplary manner by the accompanying drawings. The drawings and accompanying description should be understood to explain principles of the embodiments rather than be limiting. Other embodiments will become apparent from the description and the drawings:

FIG. 22-31 show examples of plots of data collected with or associated with the embodiments disclosed herein.

DETAILED DESCRIPTION

Figure 1:
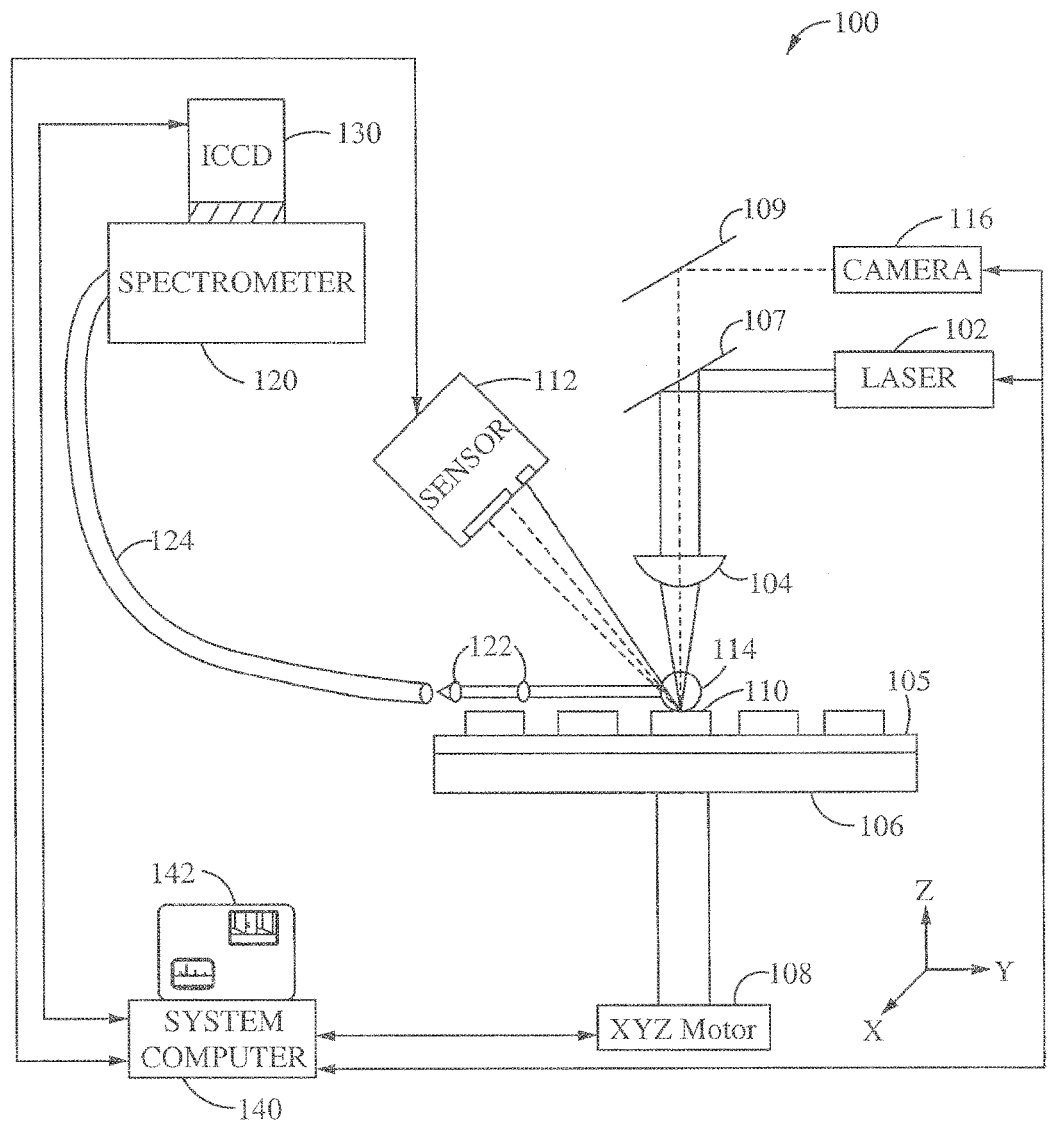
FIG. 1 is a simplified diagram of a laser ablation apparatus embodiment.

Systems, methods, compositions, and apparatus for providing novel laser induced ablation spectroscopy are disclosed. In various embodiments, an apparatus comprises a sample site position sensor, stage position motors operable to move the stage in three independent spatial coordinate directions, and a stage position control circuit to move an analysis sample site to selected coordinate positions for laser ablation, with no human interaction. The ablation of material from an analysis sample site can displace its position from a point where the laser beam has a predetermined spot size. The embodiments can have a laser position sensor to detect a change in the position of the sample site and generate a displacement signal operable for the stage position control circuit to return the sample site to an original position using the stage motors.

In various embodiments, collection optics can gather light from a plasma plume produced with a laser ablation. The collection optics can couple the gathered light into a first end of a lightguide through which the light can be transmitted to a spectrometer. The lightguide can be a single fiber optic bundle including a plurality of optical fibers held generally parallel to one another in a geometric arrangement. However in some embodiments, the various fibers in the single bundle (trunk) at the first end can advantageously be subdivided into smaller bundles (e.g. a plurality of branches) to divert various portions of the light to two or more spectrometers. Depending on the application, different branches can convey distinct preselected fractions of the light from the trunk to different spectrometers. For example, in an embodiment one branch from the trunk fiber bundle can convey a first portion of the light to a broadband spectrometer operable to analyze a relatively wide spectral segment, and a different branch can convey a second portion of the light to a high dispersion spectrometer operable to measure minor concentrations and/or trace elements. Emissions from a plasma plume can thereby be simultaneously analyzed in various ways using spectrometers having distinct and/or complementary capabilities. For example, a spectrometer having a high speed gated detector, a spectrometer having a high speed intensified detector (i.e. an ICCD), a spectrometer having an electron multiplying charge coupled device (EMCCD), and/or a spectrometer having enhanced sensitivity and/or selectivity in particular wavelength regions and or at particular wavelengths, can all receive and analyze radiation from the same plasma plume carried through different branches. It will be understood that various advantageous spectrometer characteristics may not be exclusive. For example, a spectrometer can be configured with a type of detector particularly well suited to the characteristic light throughput (efficiency) and resolution of its dispersive element(s), as well as being selectively gateable to detect light exclusively in a preselected interval following each laser pulse. In particular, an intensified multichannel charge coupled device detector can be intensified to provide very high sensitivity relative sensitivity, and/or can be synchronously gated on during a short interval following each laser pulse to discriminate against background continuum radiation.

The terminology herein is for the purpose of describing particular embodiments and is not intended to be limiting of the invention. It will be understood that, although the terms first, second, etc. may be used to describe various elements, these terms are only used to distinguish one element from another, and the elements should not be limited by these terms. For example, a first element could be termed a second element, and similarly a second element could be termed a first element, without departing from the scope of the instant description. As used herein, the singular forms "a", "an" and "the" are intended to include the plural forms as well, unless the context clearly indicates otherwise. It will be further understood that the terms "comprises," "comprising," "includes," "including," and/or "having," as used herein, are open-ended terms of art that signify the presence of stated features, integers, steps, operations, elements, and/or components, but do not preclude the presence or addition of one or more other features, integers, steps, operations, elements, components, and/or groups thereof. Reference in the specification to "one embodiment", "an embodiment", or some embodiment, etc. means that a particular feature, structure, or characteristic described in connection with the embodiment is included in at least one embodiment. The appearances of the phrase "in one embodiment" in various places in the specification are not necessarily all referring to the same embodiment, nor are separate or alternative embodiments mutually exclusive of other embodiments.

As used here, various terms denoting spatial position such as above, below, upper, lower, leftmost, rightmost and the like are to be understood in a relative sense. The various aspects of the apparatuses described herein are operable without regard to the spatial orientation of the apparatuses as a whole. For example, an apparatus can be configured in a vertical orientation or in a horizontal orientation. Hence a component or module that is described as being above another component or module in a first embodiment having a first orientation, could equivalently be described as being to the left of the other component or module in an equivalent second embodiment configured to be in a second orientation 90 degrees counterclockwise with respect to the first.

The term module refers to a distinct unit that is operable to perform an identifiable function. A module can be a self-contained physical unit or piece of equipment. A module can also be a logical component effectuated by a processor and tangible media having instructions and/or data that are operable for the processor to perform the identifiable function. The term automatic refers to a module, service, or control system that is operable to perform with no human interaction. Monitoring or sensing refers to measuring a physical quantity. Monitoring is often performed for the purpose of regulation or control.

The term gas or gas phase species as used herein includes species not bound to each other that have thermal and/or directed motion in a gas phase. The term is not limited by a specific value of a mean free path between collisions. Hence the term "gas phase species" includes various different species in vapors, atomic or molecular beams, and gaseous suspensions such as aerosols, and the like.

A lightguide refers to a transmission channel for the directed transmission of luminous electromagnetic radiation over a distance. A lightguide can include one or more fine filamentary optical fibers comprised of dielectric material such as silicon dioxide, a transparent polymer, and the like. The outer surface of each individual optical fiber can have a cladding of relatively lower refractive index. A lightguide have a cross section that is circular, rectangular, U-shaped, ribbon-shaped, and others. The cross section can be solid or it can be hollow. By way of further example, a lightguide can be covered with a jacket comprised of transparent material, opaque material, and others.

The term spectrometer is generally used to identify an instrument that can used to view and/or analyze a characteristic of a substance. With reference to LIBS, an optical spectrometer (also referenced as "spectrometer") is an instrument operable to separate and detect different wavelength components in electromagnetic radiation within a range of about 180 nm to 1000 nm (ultraviolet to infrared). However, depending on the context, the term optical spectrometer ("spectrometer") can also be understood to mean the subsystem in an optical spectrometer operable to disperse and/or separate various wavelength components of the electromagnetic radiation (e.g. a monochromator or polychromator exclusive of an electromagnetic radiation detector). The intended meaning can be understood from the context.

The term a mass spectrometer (MS), as used herein, references an instrument that can separate and detect ions gas based on their charge to mass ratio. The term inductively coupled plasma mass spectrometer (ICP-MS) will be understood to mean an analysis instrument based on ionizing gaseous species in a high temperature inductively coupled (thermal) plasma, extracting such ionized species from the plasma, and determining their composition with a mass spectrometer.

The present teachings may be embodied in various different forms. In the following description, for purposes of explanation, numerous specific details are set forth in the description and drawings in order to provide a thorough understanding of the various principles. Furthermore, in various instances, structures and devices are described and/or drawn in simplified and/or block diagram form in order to avoid obscuring the concepts. However, it will be apparent to one skilled in the art that the principles can be practiced in various different forms without these specific details. Hence aspects of the invention should not be construed as being limited to the embodiments set forth herein.

FIG. 1 shows a schematic overview of a laser ablation apparatus 100 according to the present invention. The apparatus 100 generally includes a pulse laser 102, a stage 106, a position sensor 112, a spectrometer 120 and a system computer 140. The apparatus 100 is configured to generate laser pulses from the pulse laser 102. The laser pulses are focused onto a sample 105 with a lens 104 to produce a plasma plume 114 of the sample 105 at a sample site 110. The position sensor 112 is electrically coupled with the system computer 140 for sending a displacement error signal to automatically correct positioning of the stage 106 during an ablating process as describe further below. The apparatus 100 can include a system frame for housing the various components described herein. The system frame can include an air filter for filtering contaminants produced during the ablating process.

The pulse laser 102 in an exemplary embodiment comprises a neodymium doped yttrium aluminum garnet (Nd:YAG) laser for generating energy in the near infrared region of the electromagnetic spectrum with a wavelength of 1064 nm. The pulse duration can be approximately 4 ns for generating a laser beam with a power density that can exceed one GW/cm.sup.2 at a focal point or ablation impact point. The laser 102 can have a repetition rate of approximately 10 hz or alternately lower than 10 hz in some embodiments. Alternatively, the pulse duration can vary to tens or hundreds of nanoseconds. In another embodiment, the pulse duration can be shortened to ultra short femtoseconds. The lens 104 comprises an objective lens used to focus the laser beam on a surface of the sample site 110. The laser beam can be focused to a spot size of approximately 10-500 micrometers on the sample site 110. In an exemplary embodiment, the laser beam can be focused to a spot size of approximately 150-200 micrometers on the sample site 110.

In an alternative embodiment, a spark generator can be used as the ablation source instead of the pulse laser 102 or a spark can be synchronized and used in combination with the laser pulse. An electric spark is passed through a sample material until the sample material reaches a temperature where characteristic spectral emissions can be detected. In an exemplary embodiment, the electric spark can be controlled in an argon atmosphere. A person of ordinary skill in the art can appreciate the construction of such spark generators in spark spectroscopy systems.

A dichroic mirror 107 is used for directing the laser beam toward the sample site 110 and a mirror 109 allows viewing of the sample site 110 using a video camera 116.

The stage 106 includes an attached array of 'x-y-z' motors 108 for providing translation of the stage 106 in a three dimensional space. The x-y-z motors can comprise suitable stepper motors driven by stepping motor controllers (not shown), as known by a person of skill in the art. In one embodiment, the stage 106 can have a translation rate of approximately 10 cm/s. The stage 106 can include a sample securing means.

Figure 1A:
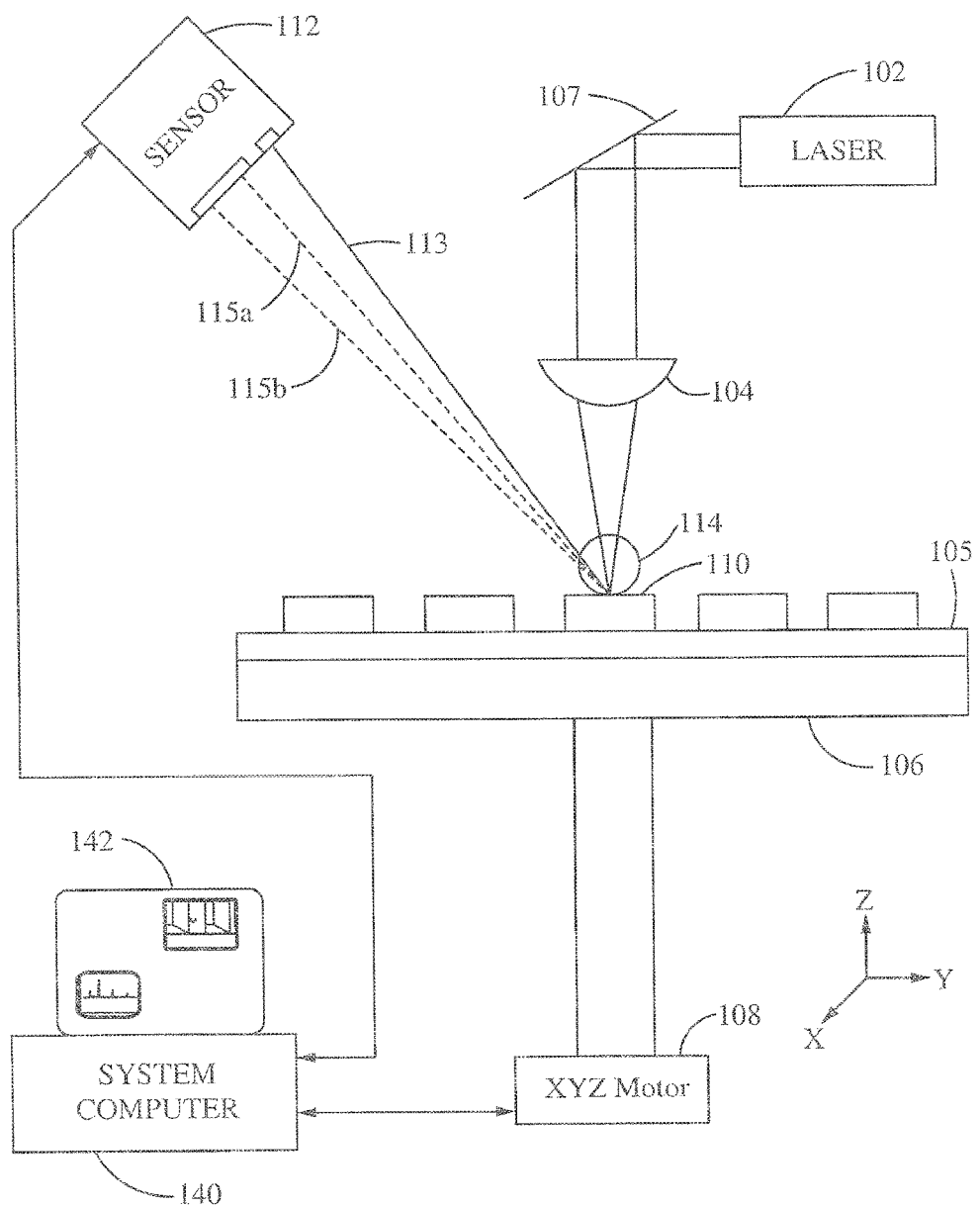
FIG. 1A is another diagram of a laser ablation apparatus embodiment.

The position sensor 112 preferably comprises a laser triangulation sensor. The position sensor 112 preferably uses the principle of triangulation to determine changes in height of the stage 106 and the associated sample 105. As shown in greater detail in FIG. 1A, triangulation occurs when the position sensor 112 emits a triangulation laser beam 113 that is focused on the sample site and a first reflection 115a is sensed by a photodetector within the position sensor 112. A change in height of the sample site 110 causes a displacement in the triangulation laser beam 113 to produce a second reflection 115b and a displacement signal generated by the position sensor 112 is communicated to a system computer 140. The system computer 140 provides positioning information to maintain an optimum height of the sample site. The position sensor 112 can comprise a suitable laser displacement measuring device as known to a person of skill in the art. In one embodiment, the triangulation laser 113 coincides with a spot circle of the laser 102 generated at the sample site. The triangulation laser 113 can also be used as a targeting marker when selecting a specific point on the sample site 110 as seen with the video camera 116 as the triangulation laser 113 can produce a visible spot on the surface of the sample site 110.

The spectrometer 120 (FIG. 1) collects electromagnetic information from the plasma plume 114. The spectrometer 120 can be a monochromator or a polychomator with a detector. The electromagnetic information includes spectral information identifying an elemental composition of the sample site 110. A spectral range for the spectrometer 120 can be chosen to suit different applications. In an exemplary embodiment the spectral range can be approximately 35 nm for observing a portion of the electromagnetic wavelength range. Alternatively, the spectrometer 120 can detect electromagnetic radiation in a range of 200 to 900 nm. Collection optics 122 receive light and plasma lumina generated from the plasma plume 114 and transmits the light and plasma lumina through a fiber cable 124 to the spectrometer 120. The collection optics 122 can be orientated horizontally as shown in FIG. 1. Alternatively, the collection optics 122 can be orientated at any angle above the sample 105 surface plane. A mirror (not shown) within the spectrometer 120 reflects the plasma lumina to a grating that disperses the plasma lumina.

An intensified charge coupled device (ICCD) or detector 130 is coupled with the spectrometer 120 for detecting the dispersed plasma lumina. The detector 130 provides the detected plasma lumina to the system computer 142. The system computer 140 generates spectral information from the plasma lumina of the laser plume 114. The spectral information includes intensity data representing elemental information and composition of the sample site 110. The spectral information can be produced on a display 142.

The detector 130 provides increased resolution and greater selectivity of the spectral information. The detector 130 includes a microchannel image intensifier plate. The intensifier plate is preferably gated during period of time when the plasma plume 114 emits characteristic atomic emission lines of the elements. This period coincides with an optimum plume luminance period. This period follows emission of continuum radiation. Continuum radiation lacks useful specific species or elemental information. In one embodiment, a delay generator (not shown) can be included to provided gating of the detector 130 to allow temporal resolution of the detector 130 response time. Alternative embodiments of the detector 130 can include a detector other than an ICCD, for example a suitable charge coupled device (CCD) or suitable photomultiplier. Accuracy of the spectrometer 120 and detector 130 in one embodiment can generate compositional data in the range of 20 ppm or less. Alternatively, the accuracy can be in the range of a few %. In another embodiment, the accuracy can be in the range of 1%, which is approximately 10,000 ppm.

The system computer 140 can include application software and a controller in the system computer 140 for providing synchronization of the laser 102, spectrometer 120, detector 130, position sensor 112 and the x-y-z motors 108 positioning of the stage 106. The system computer 140 is electrically coupled with the laser 102, spectrometer 120, detector 130, position sensor 112, the x-y-z motors 108 and the camera 116. The system computer 140 includes a display 142 for displaying spectral information. The system computer 140 can present the spectral data generated on the display 142. Alternatively, a separate personal computer can also be coupled with the system computer 140 for separately analyzing the spectral information. The system computer 140 can include a power controller to regulate power to all the apparatus 100 components.

The application software decodes the spectral information from the detector 130 and facilitates analysis of the spectral information and generates composition information of the sample 105. In one embodiment, the intensity data of an elemental peak is subtracted from background data of the elemental peak to calculate a change in intensity (delta I). The application software allows setting of certain parameters for performing the laser ablations of the sample site 110. A laser spot circle size can be set as a parameter and can be consistently and precisely maintained through the laser ablation process described in further detail below. Alternatively, a z value for the sample site 110 can be set as a parameter and can be consistently and precisely maintained through the laser ablation process. The spot circle increases or decreases depending on the change in height of the sample site 110. Keeping the laser 102 spot circle precisely adjusted insures that the sample site 110 produces the plasma plume 114 with consistent optimum plume luminance. Height changes in the sample site can be detected by the position sensor 112 and a correction to the height of the sample site 110 is generated by the controller within the system computer 140. The application software and the controller generate correction signals to reposition the height of the stage 105 after each laser ablation of the sample site.

Figure 2:
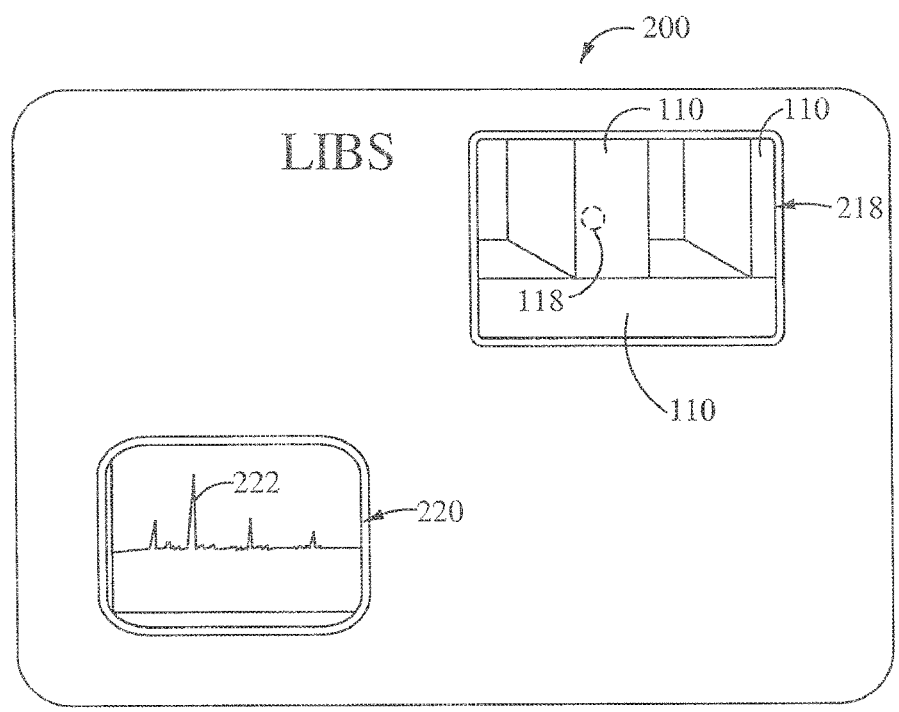
FIG. 2 illustrates a detail of a laser ablation graphical user interface.

FIG. 2 shows a representative graphical user interface (GUI) 200 according to an embodiment of the present invention. The GUI 200 includes a first data window 218 and a second data window 220. The first data window 218 provides real-time video of a sample site 110. A spot circle 118 can be observed on the sample site 110 during and following an ablation. The second data window 220 provides spectral information generated from the system computer 140. In an exemplary embodiment, the spectral information includes a waveform 222 representing intensity and wavelength data of a sample site ablation.

Figure 3:
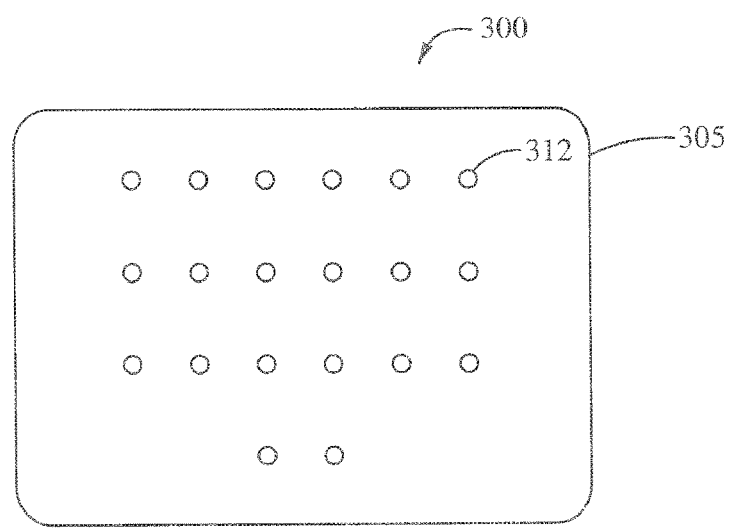
FIG. 3 illustrates a plan view of a testing protocol.

FIG. 3 shows a top view 300 of a protocol for ablating a sample 305 according to an embodiment of the present invention. The protocol includes ablating multiple sample sites 312. In an exemplary embodiment, the sample sites can be uniformly and evenly distributed throughout a surface of the sample 305. Alternatively, the sample sites 312 can be randomly distributed through the surface of the sample site. The number of sample sites 312 ablated can vary depending on a particular sample or a particular application. The spectral data of the individual laser ablation sites can be used to form a chemical map of the sample surface or the total number of laser ablations for the sites can be averaged together. In one embodiment, the number of sample sites comprises twenty. Alternatively, the number of sample sites can be ten or fewer. In another embodiment, the number of sample sites can be thirty or more.

The protocol 300 can include a specific number of pulse laser ablations per sample site 312. Heterogeneous material can include elements having varying thermal properties. A single shot laser ablation can vaporize disproportionately more volatile elements than the less volatile elements. Spectral information from a single ablation may not be a reliable indication of the composition of the sample 305. In an exemplary embodiment, the number of laser ablations per site comprises three laser ablations. Alternatively, the number of laser ablations per site comprises two. In another embodiment, the number of laser ablations per site comprises a single laser ablation. In still another embodiment, the number of laser ablations per site comprises four or more laser ablations.

Figure 4A:
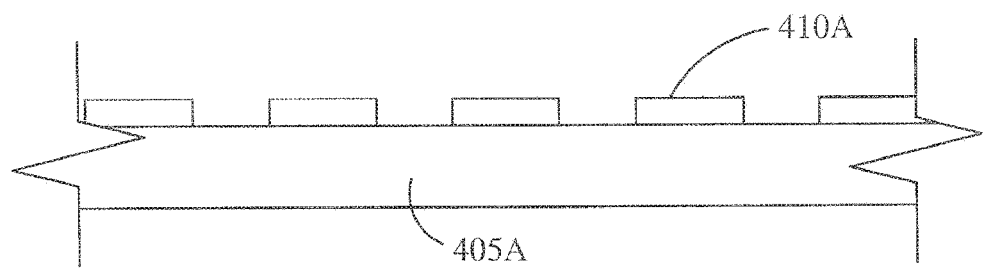
FIGS. 4A and 4B illustrate side views of a topology of a sample according to an embodiment.
Figure 4B:
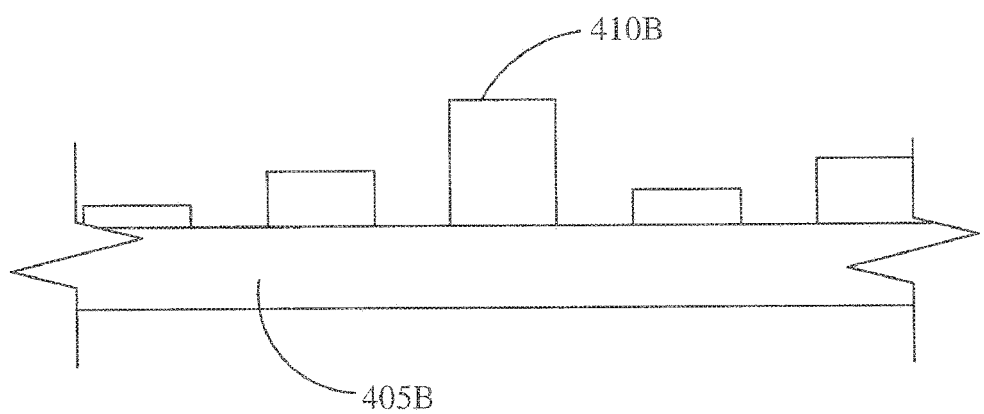

FIGS. 4A and 4B show side views of a first sample 405A and a second sample 405B according to an embodiment of the present invention. The first sample 405A comprises a material having sample sites 410A with substantially uniform topology. The height of the sample sites 410A are substantially the same. The second sample 405B, however, comprises a material having sample sites 410B with erratic or varying topology. The height of the sample sites 410B can be different. The apparatus 100 is configured to provide consistent spectral data for either the uniform sample sites 410A or sample sites 410B with varying heights. The system computer 140 adjusts the height of the stage 106 to achieve the optimal plasma lumina.

Figure 5:
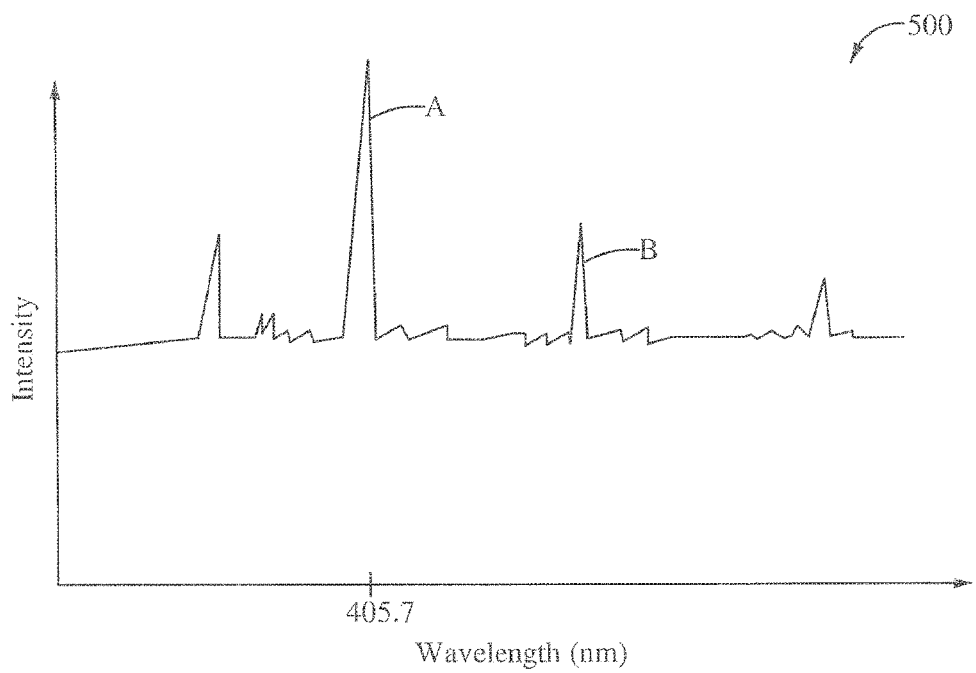
FIG. 5 illustrates a plot of spectral information according to an embodiment.

FIG. 5 shows a plot 500 of spectral data according to an embodiment of the present invention. The plot 500 includes a waveform plotted along a wavelength (nm) versus an intensity (a.u.). An elemental peak 'A' can represent the spectral information for the element Lead (Pb). The elemental peak 'B' can represent spectral information of a different element.

Figure 6:
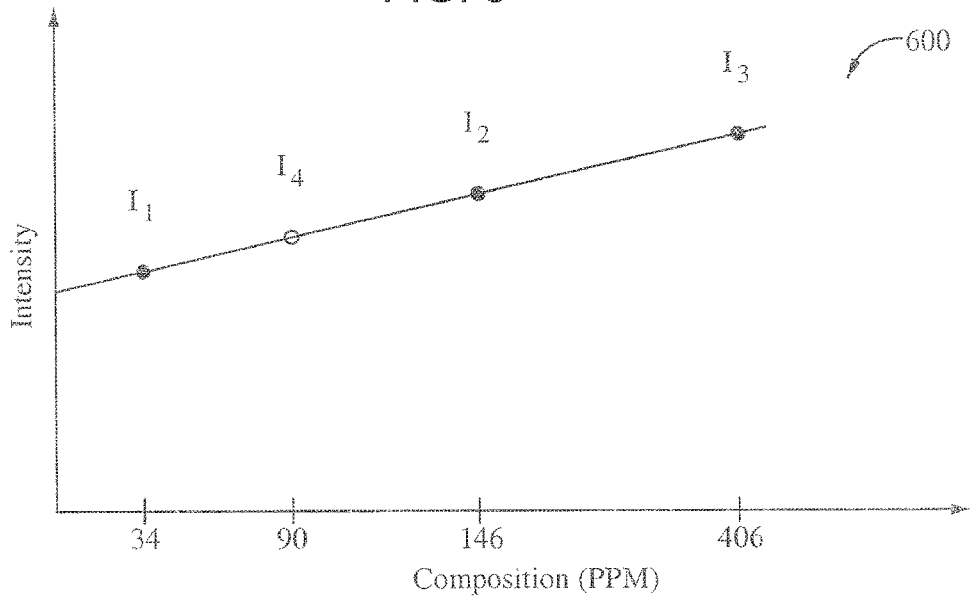
FIG. 6 illustrates a plot of intensities of known standards according to an embodiment.

FIG. 6 shows a plot 600 of compositional data 600 according to an embodiment of the present invention. The plot 600 includes a waveform plotted along a composition (nm) versus an intensity (a.u.). The plot 600 is generated by performing laser ablation according to the method described herein on a known standard sample. The known standard produces intensities I1, I2 and I3 for associated elements at the respective compositions 34 ppm, 146 ppm and 406 ppm. Quantitative analysis of different elements of a particular sample is performed by comparing spectral data of the particular sample with the compositional data 600. For example, spectral information obtained from analysis with the apparatus 100 can include intensity 14. The quantity of the element can be approximated to 90 ppm.

Figure 7:
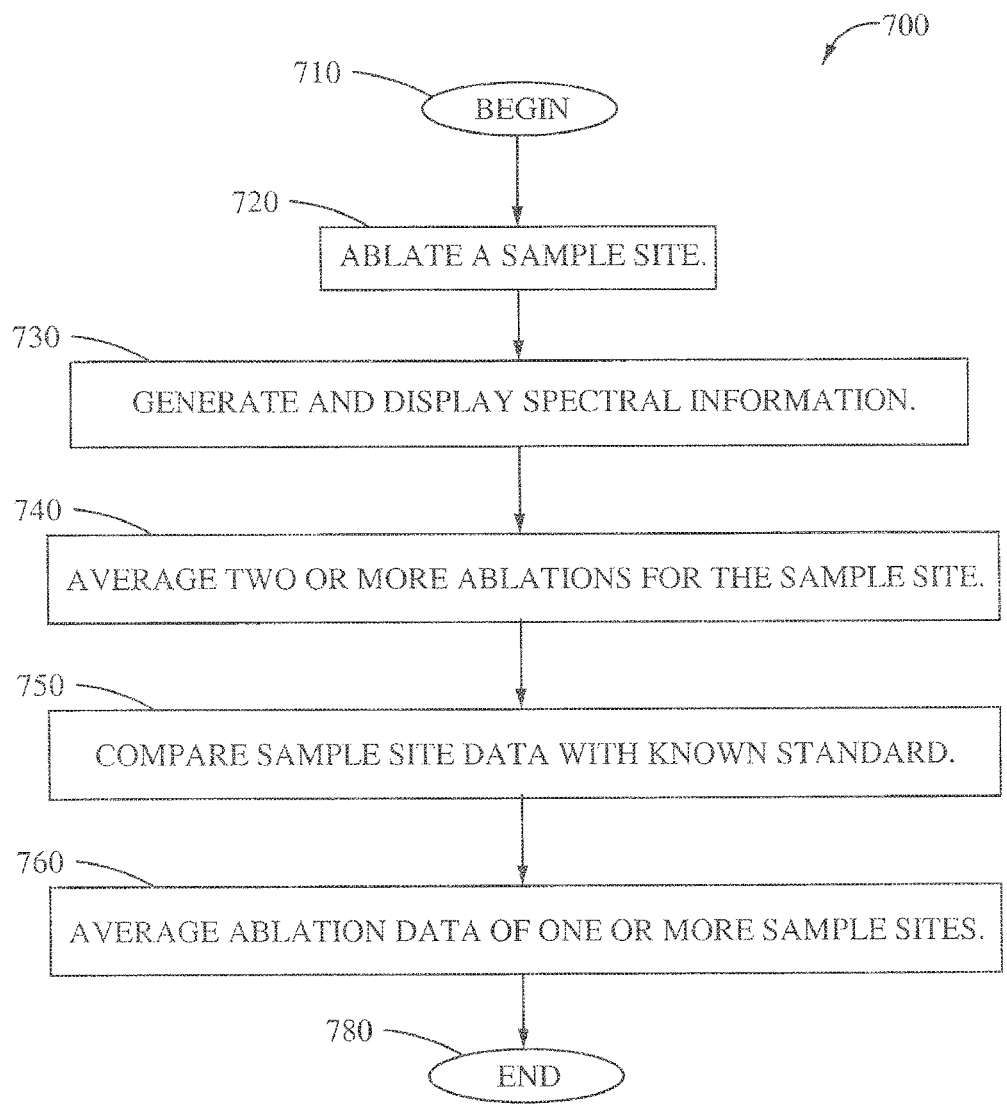
FIG. 7 illustrates a process flow diagram for a method of ablating.

FIG. 7 shows a process flow diagram for a method 700 of laser spectroscopy according to an embodiment of the present invention. The laser ablation apparatus 100 (FIG. 1) is used as an example. The method 700 begins at the step 710. In one embodiment, the method 700 can be fully automated using application software included in the system computer 140. A specific protocol can be entered into the application software instructing the application software of desired parameters or settings for the apparatus 100. Alternatively, the method 700 can be manually performed. At the step 720, a laser pulse is generated to ablate the sample site 110 into an emissive plasma plume. A real-time video image of the sample site 110 is generated on a first window 218 of the GUI 200. The real-time video is received from the video camera 116. The plasma plume 114 is analyzed by the spectrometer 120 and the detector 130. The plasma lumina and the electromagnetic radiation generated by the plasma plume is optically communicated to the spectrometer 120 and detected by the detector 130. The position sensor 112 provides a displacement signal to the system computer 140 indicating any change in the height of the sample site 110. The system computer receives spectral information from the spectrometer 120 and the detector 130.

At the step 730, the system computer 140 generates spectral and wavelength information for presentation on the display 142. In one embodiment, intensity and wavelength data are represented as waveforms on the GUI 200. The waveform is presented in a second window 220 of the GUI 200 and includes the intensity and wavelength data. In another embodiment, a second waveform is superimposed on the first waveform 222 in the second window 220. The second waveform can include additional spectral information. For example, particle imaging information, tracking information or scaled or gated representations of the first waveform 222.

At the step 740, the steps 720 and 730 are repeated for each sample site on the sample. The spectral data for a total number of laser ablations for the sample site 110 can be averaged together. In an exemplary embodiment, the total number of laser ablations for the sample site 110 equals three laser ablations. The spectral data of the three laser ablations are averaged together to generate a 'site sum'. The site sum is a reliable and accurate representation of the elemental composition of the sample 105 at the sample site 110. Alternatively, the site sum comprises spectral data from two laser ablations. In another embodiment, the site sum comprises spectral data from one laser ablation. In still another embodiment, the site sum comprises spectral data from four or more laser ablations.

At the step 750, the site sum can be compared with spectral information generated from performing the method described herein on a known standard material. The known standard material comprises specific known elements at a known composition. Laser spectroscopy performed on the known elements generates known spectral data including known intensity values. An elemental composition for the sample site 110 can be approximated by comparing the site sum with the known standard spectral data.

At the step 760, the steps 720 through 750 can be repeated for one or more additional sample sites to generate additional site sums. The spectral data for the total number of site sums can then be averaged together. In an exemplary embodiment, the total number of site sums equals twenty. The spectral data of the twenty site sums can be averaged together to generate a 'sample sum'. The sample sum is a reliable and accurate representation of the elemental composition of the sample 105 as a whole. Alternatively, the total number of sites sums can be ten or fewer. In another embodiment, the number of sites sums can be thirty or more.

The apparatus 100 can perform laser ablation or laser induced breakdown spectroscopy (LIBS) on a variety of materials. The materials can be heterogeneous or homogeneous solids or semi-solids. Alternatively, the materials can comprise a liquid or even a gas. In another embodiment, the apparatus 100 can be used for LIBS on biological materials. Analysis of biological material can include building a library of known spectral signatures including elemental and compositional data for specific biological material. The spectrometer 120 can collect and detect with the detector 130 spectral information on a broad range from 200 to 900 nm. An unknown biological sample can be compared with the library to determine the biological substance. The method ends at the step 780.

In an alternative embodiment, the method 700 can be used in a remote configuration. The sample material is positioned in a location that is remote from the ablation source or laser. A telescopic device can be integrated with the apparatus 100 to provide optical coupling of plasma lumina. The generation and analysis of spectral data can proceed similarly as described herein. Furthermore, other spectroscopies, in place of and/or in addition to optical emission spectroscopies can be used to obtain characteristic ablation spectral data within the scope of the present invention. For example, laser ablation inductively coupled plasma mass spectrometry (LA-ICP-MS) can be applied in conjunction with and/or as an alternative to the LIBS technique described herein.

Still further embodiments can be understood with respect to FIGS. 8-13. Like numerals in FIGS. 8-13 designate corresponding elements.

Figure 8:
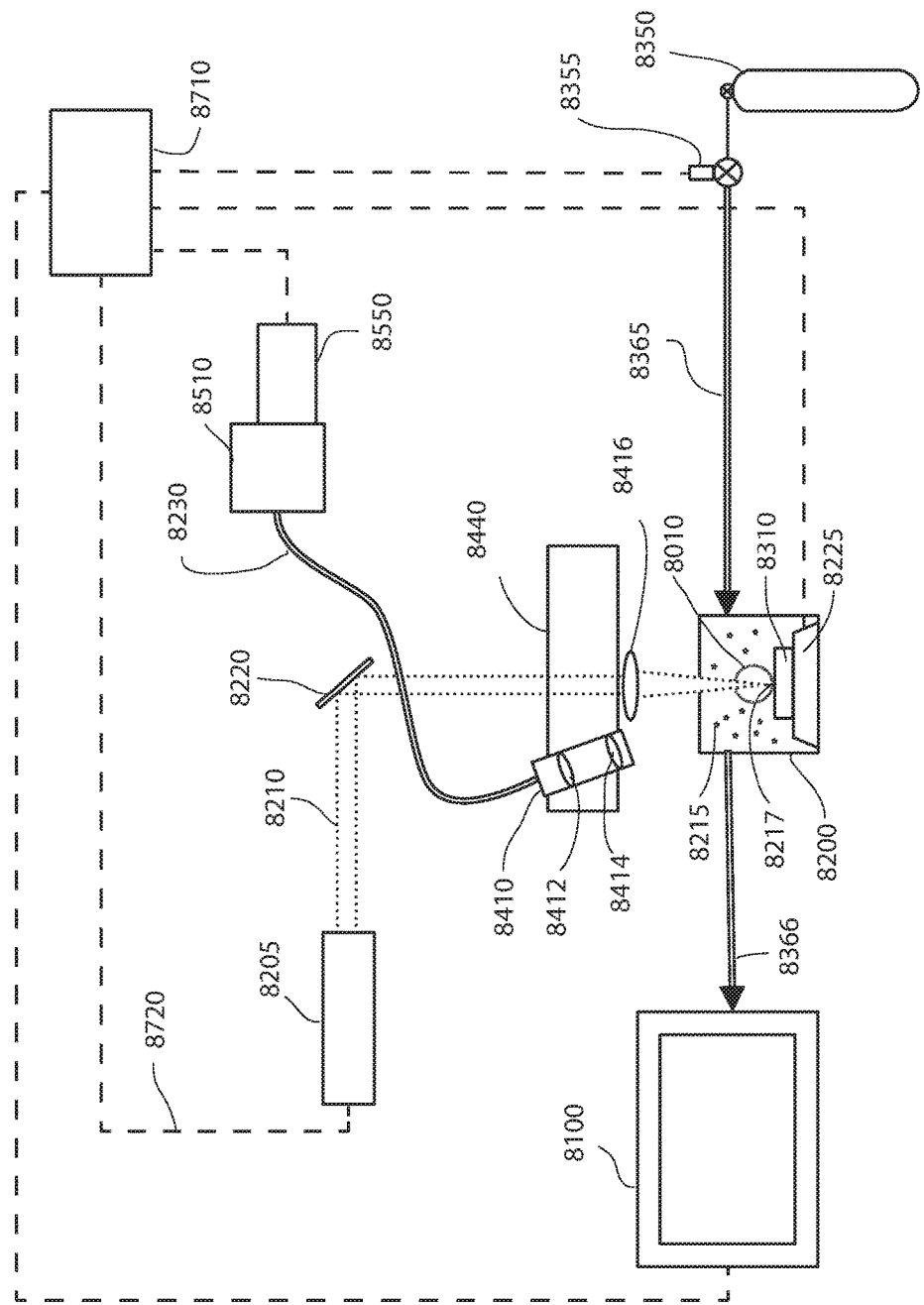
FIG. 8 is a simplified diagram of apparatus for laser induced ablation spectral analysis including LIBS and LA-ICP-MS.

FIG. 8 is a simplified drawing of a system for laser induced ablation spectral analysis of a sample. The system has a movable stage 8225 coupled to x-y-x translation motors (not shown) that can move a sample 8310 on the stage in three independent directions. The system also has a laser 8205 that can emit a pulsed laser beam 8210, and has various optical elements such as a mirror 8220, laser beam focusing optics module 8416 and/or others that can cooperatively focus the laser beam onto a selected sample site 8217 for ablation. The sample 8310 and stage can be in an unreactive gaseous atmosphere confined within enclosure

8200. The atmosphere in the enclosure can be transparent at wavelengths comprising pulsed laser beam and/or characteristic spectral emission emanating from the plasma plume 8010. In a preferred embodiment, the pulsed laser 8205 can be a Nd YAG laser emitting a pulsed laser beam with a near infrared wavelength of 1064 nm, and the unreactive atmosphere can be inert gas such as helium and/or argon.

However an ultraviolet wavelength selected from among 193 nm, 266 nm and 193 nm is preferred for the ablation for some applications, particularly when performing analyses using ICP-MS. UV wavelengths can provide a better sample of gaseous species from a sample site by comparison to a more conventional pulsed laser wavelength in the near infrared. Short UV wavelengths can be generated as harmonics of longer wavelength exicimer and/or solid state lasers as will be understood by those having ordinary skill in the art.

Figure 12A:
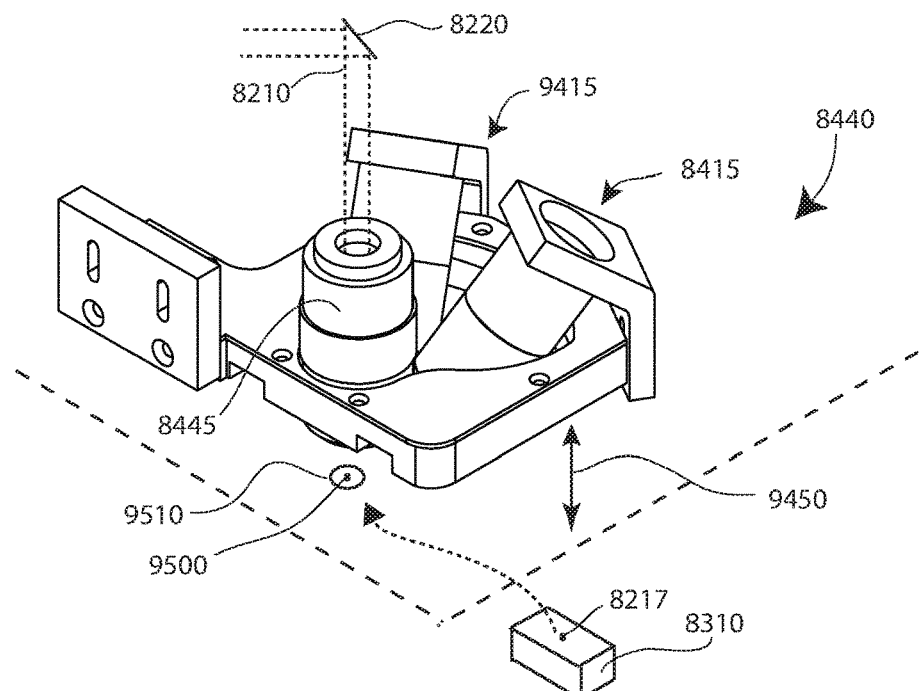
FIG. 12A is an isometric view of an optical frame for an LIBS apparatus.
Figure 12B:
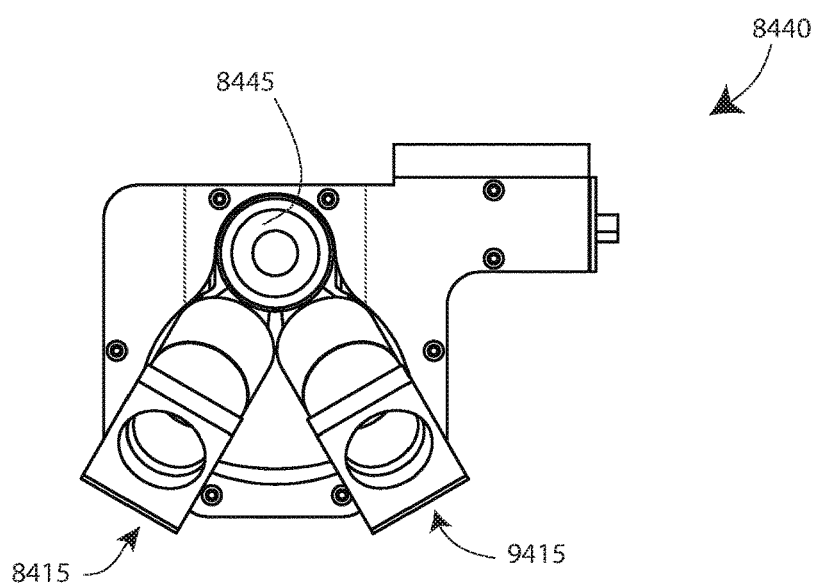
FIG. 12B is an overhead view of the optical frame shown in FIG. 12A.

Characteristic spectral emission emanating from the plasma plume 8010 generated by ablation can be gathered with a collection optics module 8410. The collection optics module can couple the spectral emission into a lightguide 8230. The lightguide can transmit the optical emission to an optical spectrometer comprising wavelength separation unit 8510 and detector 8550. The collection optics module can include lenses 8412, 8414 and/or other optical elements and is disposed in a preselected position and orientation by optical frame 8440. Further details of an optical frame structure 8440 are disclosed in FIGS. 12A, 12B and 13. As shown in FIG. 12A, the laser beam focusing optics module 8445 is secured to frame 8440 in a position where it can center a precise laser spot circle 9510 of predetermined size in plane 9460 on a point 9500. Plane 9460 is a preselected distance 9450 below optical frame 8440. Accordingly, stage 8225 can movably translate a selected sample site 8217 (also see FIGS. 9-10) to the center laser spot circle position to perform precise and consistent laser ablation of material from the selected site.

As can be understood with respect to FIGS. 10-13, the optical frame 8440 has support substructures 8415, 9415 operable to secure collection optics modules 8410 and/or 9410 in a preselected positions with respective central axis/axes 8416 and/or 9416 of each collection optics module aimed at a situs 9300 of the plasma plume. This arrangement positions each laser ablation and its ensuing plasma plume in the same location relative to the optics support structure 8440. Accordingly, each optics support substructure 8415, 9415 can hold a respective collection optics module 8410, 9410 in a fixed position and orientation that can optimize light collection from a plasma plume arising from the spot circle position.

In various embodiments, a gas flow system such as shown with respect to FIG. 8 can maintain an atmosphere of unreactive carrier gas in sample/stage enclosure 8200. A source of pressurized unreactive gas 8350 can be coupled to a flow controller 8355 through a fluid channel comprised of conventional tubing, pipe and/or fittings. The flow controller 8355 can deliver a selected flow rate of the carrier gas to enclosure 8200 through fluid passage 8365. Flow controller 8355 can be a pneumatic flow controller, an electronic mass flow controller, a fixed orifice, and others. The flow rate can be controlled using a computer 8710 to actuate the flow controller and/or provide a setpoint by way of a communication channel represented by the dashed line between a computer 8710 and flow controller 8355.

In some embodiments, gaseous laser ablation products 8215 generated in chamber 8200 can be transported in the carrier gas from enclosure 8200 to an inductively coupled plasma-mass spectrometer (ICP-MS) 8100 through flow channel 8366. In various embodiments, the gaseous laser ablation products can include permanent gases, vapors, molecular clusters, suspended particles, aerosols and/or others. The inductively coupled plasma-mass spectrometer (ICP-MS) 8100 is operable to perform a further spectral analysis of the ablation products based on the mass of ionized species. In various embodiments, the ICP-MS comprises an inductively coupled thermal plasma sustained in an inert carrier gas such as argon. Those having ordinary skill in the art will recognize that thermal plasma sustained in the ICP-MS 8100 have sufficiently high temperature (over 5000K) to ionize the gaseous laser ablation products. Ionized products from the thermal plasma are introduced into a mass analyzer within the ICP-MS where they can be separated and identified based on characteristic charge to mass ratio. Accordingly, the ICP-MS analysis can provide additional information useful to augment, improve, and/or confirm an emission spectroscopy determination of sample site composition based on lumina from the plasma plume.

It has also been found that ICP-MS may not be particularly effective to determine relative relatively light elements (atomic number less than about 10) and elements generally found in organic compounds (carbon, hydrogen, oxygen and nitrogen). In this regard, it has been found that the LIBS analysis can complement and quantify the concentrations of various elements that may not be acceptably measured using ICP-MS alone. Furthermore, it is difficult to measure high concentrations of elements (bulk composition analysis) in an ICP-MS while simultaneously performing trace level chemical analysis with the same instrument. On the other hand ICP-MS is highly sensitive and can perform trace level detection/analysis at levels as low as 1 part per billion, and under some circumstances even lower levels are operable. It has been found that a combination of laser ablation emission spectroscopy and laser ablation ICP-MS can determine both high concentration level analysis as well as trace levels at 1 ppm or even 1 ppb of a single sample site, which could not be performed using either laser ablation emission spectroscopy or laser ablation ICP-MS alone. Yet another advantage having both techniques in combination arises from an ability to detect pulse-to-pulse variations in the amount of ablated material based on a signal level in from wideband emission spectra. The emission signals can be useful to normalize and/or correct the ICP-MS mass/charge intensities thereby improving accuracy.

A system with respect to FIG. 8 can include at least one computer 8710. The computer comprises machine readable media operable to store data and instructions and a processor that can read the data and perform the instructions. Furthermore, media has various modules operable to effectuate various control functions, control loops, displays, human interfaces, and others. The dashed lines 8720 shown in FIG. 8 represent communications channels between the computer and various system components such as pulsed laser 8205, ICP-MS 8100, an optical spectrometer wavelength separation unit 8510, a spectrometer detector 8550, an electronic flow controller 8355, and a stage position controller for x-y-z stage 8255. The system can also include communications channels for a sample site position sensor, and other physical and/or software components not shown in FIG. 8. It will be recognized that a communication channel can be implemented in various different ways. For example, data and/or instructions can be carried by way of physical media as point to point wiring, over a parallel bus, over serial and/or parallel fiber optic connections, with a virtual circuit in a network protocol layer, and/or others.

It will be understood that various embodiments with respect to FIG. 8 can further include a number of additional elements and structures disclosed in relation to FIGS. 1-7 above. These elements are been omitted from the drawing to avoid obscuring other concepts simplify the explanation. By way of example, a system with respect to FIG. 8 can include a video camera, a sample site position sensor and an x-y-z stage position controller in a stage position control circuit, a triangulation laser, and others. Furthermore, some embodiments do not include all of the elements and subsystems shown. For example, there are embodiments with an ICP-MS. In these embodiments unreactive carrier gas from enclosure 8200 can be vented into an exhaust line (not shown).

Figure 9:
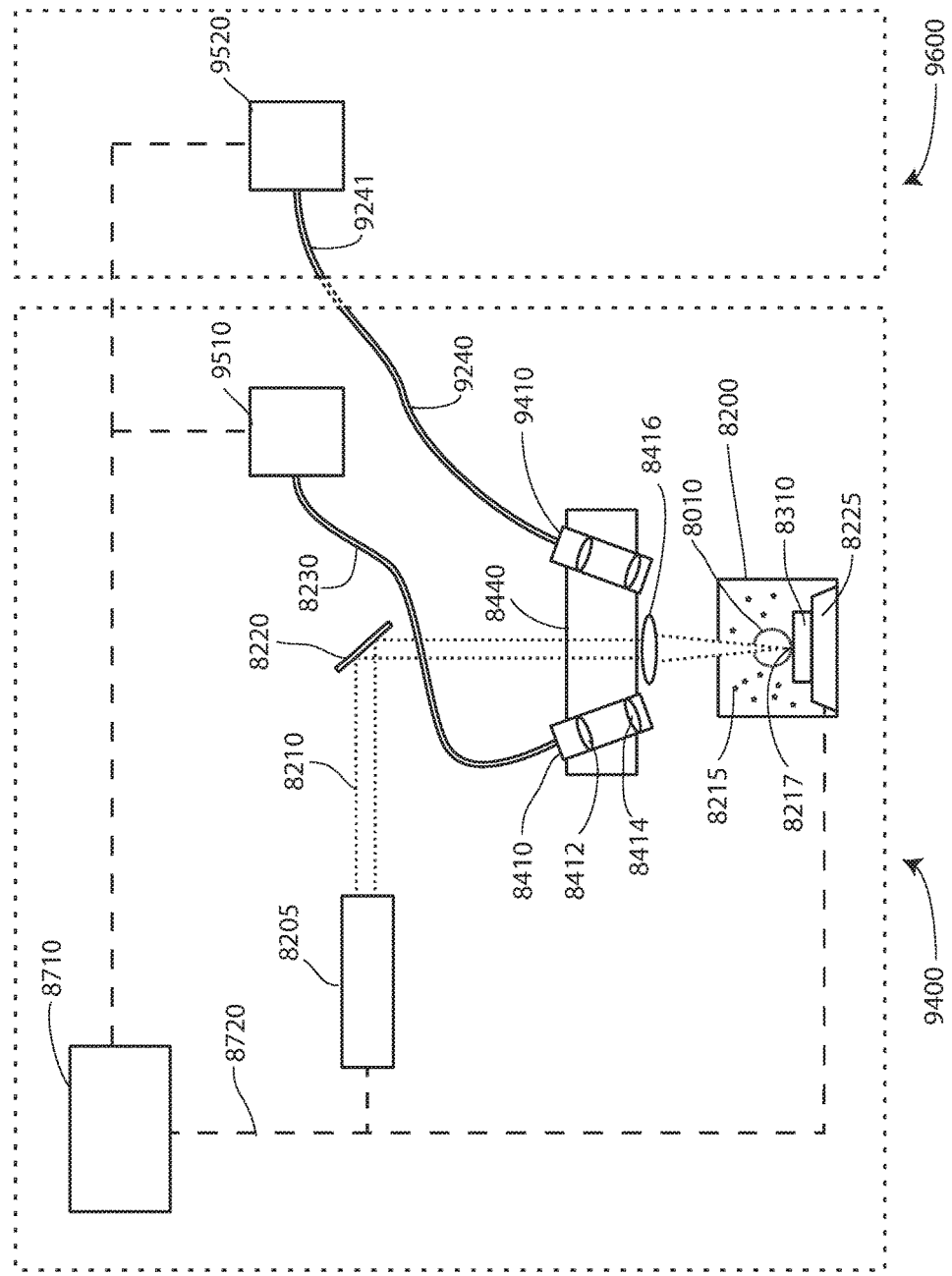
FIG. 9 is a simplified diagram of apparatus for laser induced ablation spectroscopic analysis comprising collection optics modules and fiber bundles to couple optical emission to spectrometers.

Other embodiments of a system for material analysis using LIBS can be understood with respect to the simplified diagram in FIG. 9. A system with respect to FIG. 9 comprises a master system module 9400, and can have an optional extension spectrometer module 9600. The master system module 9400 can include any of the elements and/or structures disclosed with respect to FIG. 8, including elements not shown in FIG. 9 (e.g. the carrier gas components 8350, 8355, and others are omitted for clarity). The optical frame 8440 of master unit 9400 is operable to support a second collection optics module 9410. The second collection optics module can gather spectral emission from a plasma plume 8010 and couple the light into a second lightguide 9240. Lightguide segment 9241 can deliver spectral emission to extension spectrometer 9600. In some embodiments lightguide segment 9240 in the master module and segment 9241 in the extension spectromter module can be portions of one single continuous fiber. In further embodiments, segments 9240 and 9240 can be physically different fibers optically joined through an interface connection between the master module and the extension spectrometer module.

An operable system with respect to FIG. 9 can comprise a master system module without any extension spectrometer 9520 (master only). The master only configuration can perform laser ablation optical spectroscopy using spectrometer 9510. Furthermore, a master only system can be field reconfigured to add an extension module. An extension model upgrade can add the capability to acquire emission spectra from a plume from the master system module spectrometer 9510 and extension spectrometer 9520 simultaneously. Spectral data from similar and/or different types of detectors in spectrometers 9510 and 9520 can be communicated to computer 8710 through communication channels 8720. A collection optics module 9410 to acquire plasma plume light emission for the extension spectrometer module 9600 can be included in master unit module 9400 when it is shipped from the factory, or a second collection optics module module 9410 can added to an optical frame 8440 in the field. Various embodiments with respect to FIG. 9 comprise an optical frame 8440 having collection optics module support substructures 8415, 9425, shown with respect to FIGS. 12A, 12B and 13, to hold respective collection optics modules 8410 and 9410 in a preselected positions and orientations as shown.

Figure 13:
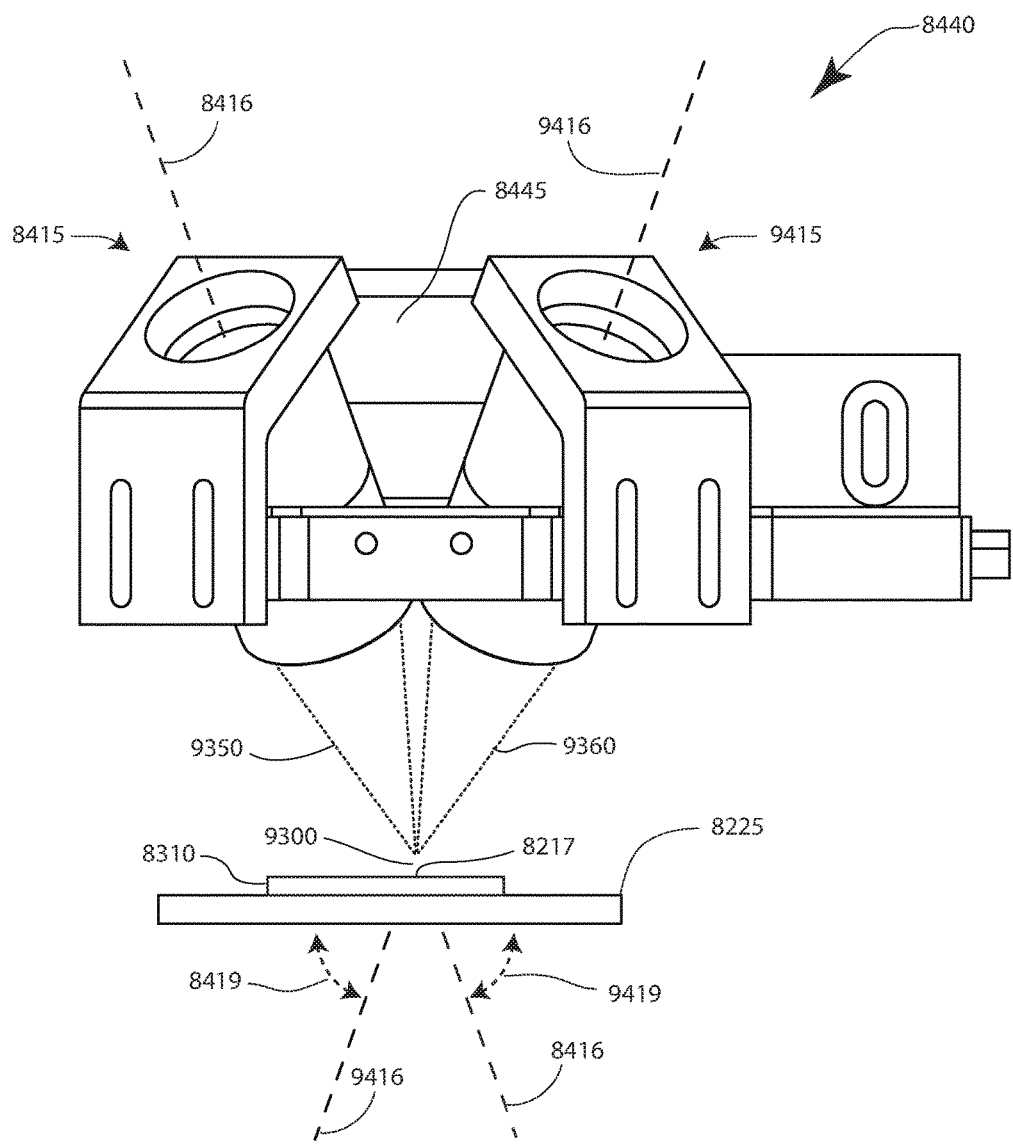
FIG. 13 is a side view of the optical frame shown in FIGS. 12A and 12B.

As shown with in FIG. 13, the supporting substructures 8415 and 9415 can have mirror symmetry with respect one another to be in predetermined positions directing the central axis 8416, 9416 of each collection optics modules to a point 9300 equidistant from each module, where the pulsed laser 8205 spot circle can generate a precise plasma plume. The central axes 8416, 9416 intersect an x-y plane parallel to the stage at equal angles 8419, 9419, from which each module can view from a plume at 9300 and capture equal portions of the light through equal solid angle cones 9350, 9360 subtended by the collection optics modules.

Figure 10:
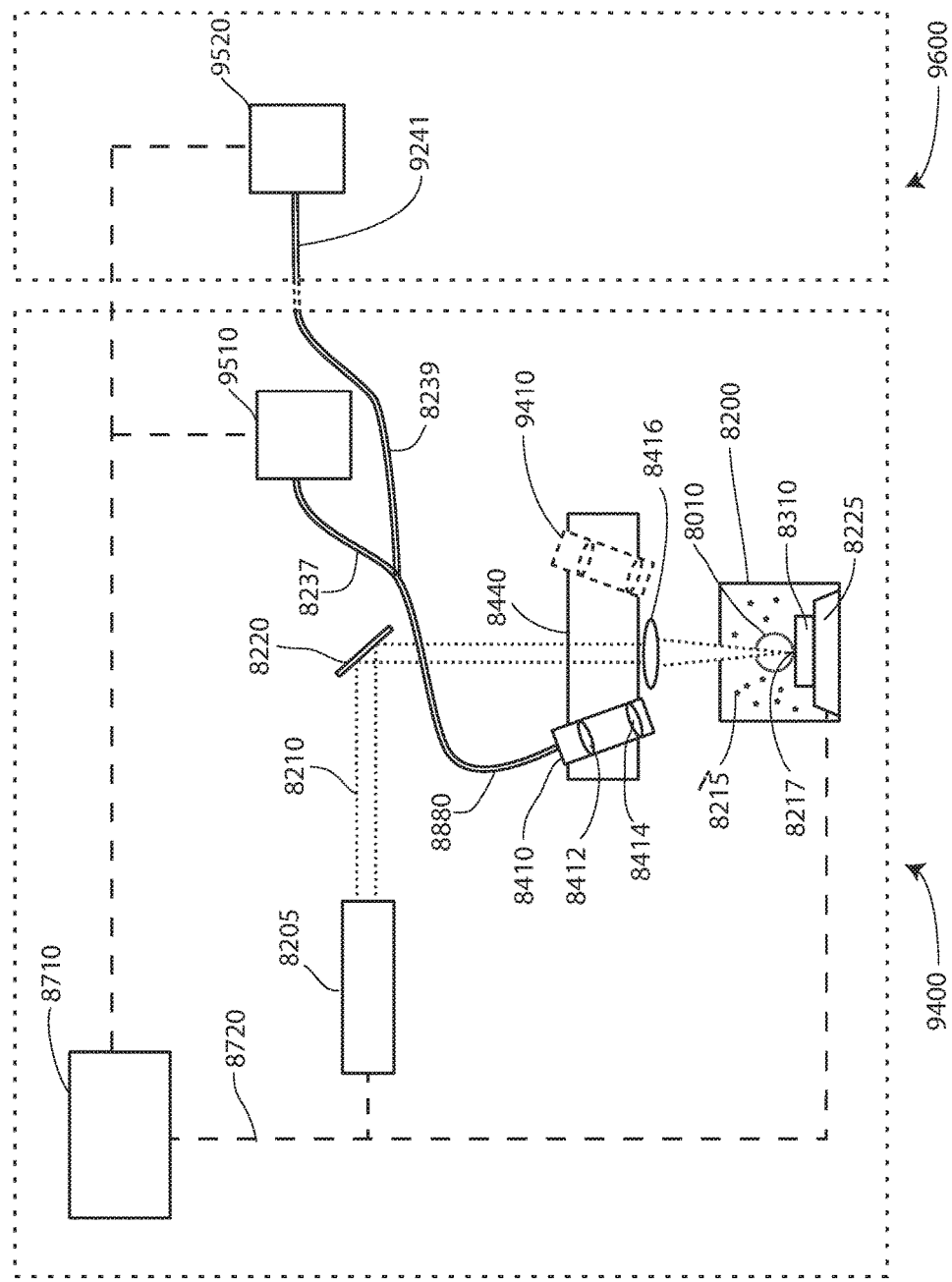
FIG. 10 is a simplified diagram showing an apparatus for LIBS having optical collection modules and lightguides for an internal and optional spectrometer modules.
Figure 11:
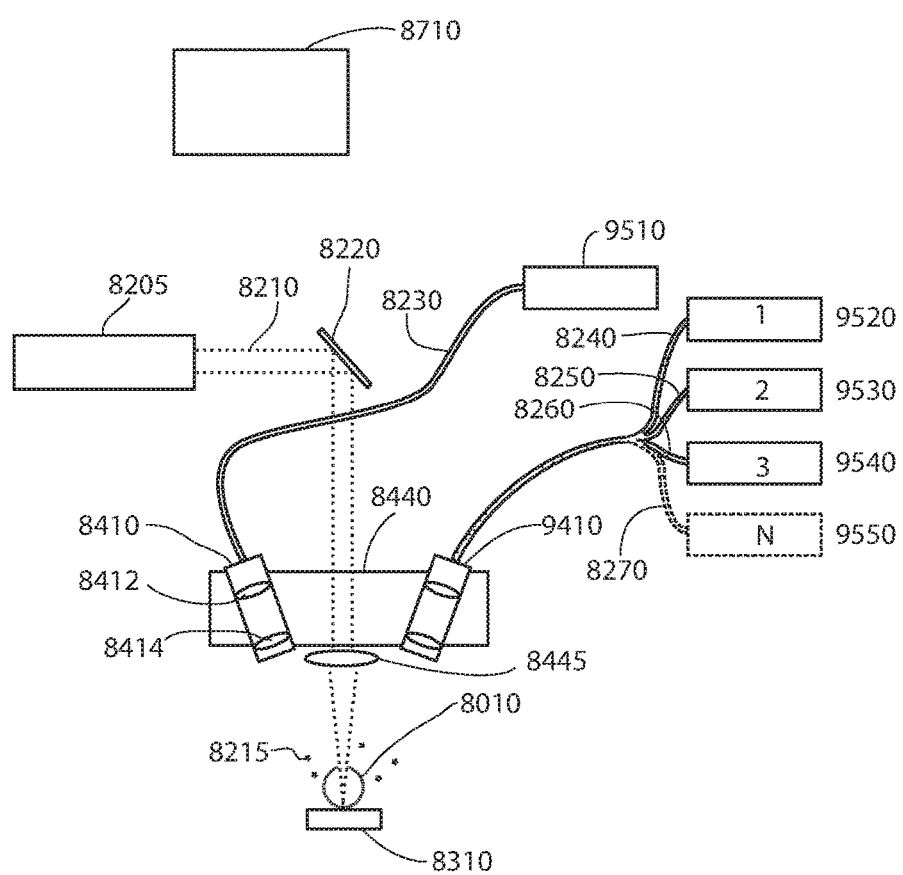
FIG. 11 is a simplified diagram of apparatus for laser induced ablation spectroscopic analysis for LIBS having one optical collection module coupled to an optical fiber bundle having split ends for an internal spectrometer and an optional spectrometer module.

In various other embodiments, a master system module can include one or more of the additional spectrometers and structures shown in an extension module with respect to 9-11 (e.g. a single master module LIBS system can comprise various spectrometers, lightguides (optical fibers), and others disclosed with respect to FIGS. 9-11), within one physical unit (the instrument).

Some further LIBS system embodiments can be understood respect to FIG. 10. A lightguide fiber optic bundle 8880 connected to collection optics module 8410 can have a bundle of equal diameter fibers at a principal (proximal) end that is subdivided into smaller bundles leading to the distal split ends 8237 and 8239. Each of the distal split ends can illuminate a separate spectrometer 9510, 9520.

Furthermore, each of the distal split end bundle portions 8237, 8239 can have different numbers of fibers. Accordingly, luminous flux received from a collection optics module by the proximal end can be divided among the split distal ends in proportion to the number of fibers constituting each split end branch. In various embodiments relative to FIG. 10, total spectral power entering the proximal principal end of fiber bundle 8880 from collection optics module 8410, can be split to deliver a relatively smaller portion of the total power through a split end bundle 8237 comprising a relatively smaller number of fibers, and can deliver a relatively larger portion of the total power through a split end bundle 8239 comprising a relative larger number of fibers. The smaller portion of power can be delivered to a high sensitivity and/or low efficiency spectrometer 9510, and the larger portion of the power can be delivered to a low sensitivity and/or low efficiency spectrometer 9520. It will be appreciated that splitting total power in this manner can provide relatively more illumination where more power is necessary and/or desired, and relatively less illumination can be directed to a spectrometer where light intensity from the collection optics module might otherwise saturate its detector.

Relative to systems having two independent collection modules and two independent lightguides disclosed with respect to FIG. 9, use of a spit end lightguide, and/or split end lightguide optical power distribution system distribution (FIG. 10) can save the costs associated of a second collection module 9410 and/or second collection module support structure elements on the optical frame 8440.

Still further embodiments are disclosed relative to FIG. 11. A system with respect to FIG. 11 can provide a first collection optics module 8410 configured to couple a maximum portion of acquired luminous power to spectrometer 9510 through lightguide 8230. Various embodiments can also have a collection optics module 9410 coupled to the proximal principal end of an n-way split end fiber optic bundle. Each split end branch can convey spectral emission to a separate spectrometer. An embodiment with respect to FIG. 11 comprises a fiber lightguide assembly having 4 distal split end bundles 8240, 8250, 8260, 8270 configured to couple to respectively different spectrometers 9520, 9530, 9540 9550. Various further embodiments can have N different spectrometers coupled to a collection optics module with using an N-way split end fiber optic lightguide. There are also embodiments having a plurality of collections optics, where at least two of the modules are coupled to first and second pluralities of different spectrometers (e.g. N and M) using N-way and M-way split end fiber optic lightguides. In this regard, all of the spectrometers in system embodiments disclosed herein can be operable to simultaneous receive the spectral emission emanating from each plasma plume generated in a laser ablation of a sample site.

An LIBS system with the capacity to analyze the spectral emission from the plasma plume at an ablation site in real time, using a plurality of optical spectrometers to receive spectral emission simultaneously, and/or in tandem, has many advantages that enable superior analytical capability relative to prior art systems. Wavelength separating elements (monochromators, polychromators, filters, and others) as well as the detectors (i.e. CCD, ICCD, EMCCD, silicon photodiodes, photomultipliers, and others) useful in an optical spectrometer have absolute and spectral sensitivity limitations that can make it impractical and/or impossible to have sufficiently high spectral resolution, sensitivity, spectral bandwidth, and temporal resolution in a single optical spectrometer instrument that is operable to broadly determine a composition of unknown samples by LIBS multi-wavelength analysis in real time. However, an individual spectrometer can be optimized to enhance sensitivity, resolution, and/or temporal resolution over limited range wavelengths. Accordingly, a plurality of optical spectrometers, individual selected and/or tuned to have optimal characteristics in a limited wavelength region, can provide spectroscopic analyses that are beyond capability of a single spectrometer system.

Analysis of a sample site by optical emission spectroscopy of the ablation plasma plume also can be limited by inherent characteristics of the plasma plume itself. For example, continuum emission can obscure characteristic spectral lines emanating from the ablated material from a sample site. As already disclosed above, continuum interference can be diminished and/or eliminated by using a high speed detector that is gated to exclusively detect line emission during a time interval after continuum intensity has decayed. Nevertheless, there are also inherent limitations arising from spectral overlap, interference, broadening, and/or low emission intensity at certain characteristic wavelengths, that remain difficult and/or impractical to overcome. Emission spectra analysis has some limitations can be traversed by applying a different spectral technology. For example, an ICP-MS can perform elemental and/or isotopic composition analyses at material concentrations well below 500 ppb, or even less than 1 ppb, that are inaccessible using emission spectroscopy alone. In various embodiments with respect to FIG. 8 simultaneous analysis of gaseous species from a sample site using ICP-MS can provide complementary ion mass to charge ratio peak intensity analytical information. In various embodiments, computer 8710 has analytical software operable to determine the composition of a sample site based on the spectroscopic data from plasma plume emission and the ICP-MS ion mass/charge ratio intensity data as a whole. It is found that the analysis based on LIBS optical emission spectroscopy and ICP-MS ion mass/charge ratio peak intensity data as a whole can detect far more elements, and can have greater analytical accuracy relative to LIBS emission spectroscopy or ICP-MS alone.

A multi-spectrometer system such as disclosed relative to FIGS. 8-11 can have use different types of optical spectrometers and detectors at the same time to advantage. Some embodiments comprise a scanning Czerny Turner spectrograph (CZ) coupled to an ICCD detector. This combination can effectuate extremely high sensitivity owing to maximal light throughput to the ICCD (high efficiency) from the spectrograph, and ICCD capability to amplify weak signals in the detector. Accordingly it is advantageous where the highest possible sensitivity is needed to detect numerous different elements present in the range of 1 to 10 parts per million. However this combination has the disadvantage that it can only capture a relatively narrow range of preselected wavelengths with a predetermined spectral resolution. Furthermore, the wavelength range and resolution vary inversely. The higher the spectral resolution, the narrower the range of wavelengths that can be covered at one time. Accordingly, to capture high resolution spectral information from atomic elements having spectral emissions in widely separated wavelength regions using only one CZ-ICCD, the CZ must be sequentially reconfigured to access each of the separated wavelength regions, and an additional ablation of the sample site must be performed after each reconfiguration to generate the spectral emissions for capture.

An embodiment may also include an Echelle spectrometer coupled to an ICCD detector. This combination has the advantageous capability of being able to capture a broad range of wavelengths at one time in emission from the plasma plume arising from a single ablation (a typical range is 200 nm-900 nm, although in a preferred embodiment the range is 190 nm-1040 nm and it can be greater). On the other hand, an Echelle spectrometer generally has low light throughput (low efficiency). For example an Echelle spectrometer can typically have f/10 aperture light throughput whereas a typical CZ spectrometer generally has about throughput in the range of f/3 to f/4. It can be seen that an Echelle-ICCD system is insensitive by comparison to the CZ-ICCD.

Accordingly, some embodiments comprise a plurality of CZ-ICCD spectrometers wherein each spectrometer is configured to receive a different preselected wavelength range. The plurality of spectrometers as a whole can capture a broad range of wavelengths at one time yet have very high sensitivity and resolution. The wavelength ranges can be contiguous and/or can be separated. Furthermore, various wavelength ranges can be non-overlapping or can have overlapping segments. All of the spectrometers can receive a portion of spectral emission a plasma plume simultaneously from one collection optics module through a split end fiber optic lightguide (described above with respect to FIGS. 10-11), and/or at least some of the spectrometers can receive equal portions of luminous energy from a dedicated of collection optic module as shown with respect to FIGS. 9, 11, and 12-13. One or several of these spectrometers can include a transmission grating operable to provide enhanced sensitivity in the red and near-infrared spectral region.

Some further embodiments comprise an array of Czerny Turner-CCD optical spectrometers (e.g. each comprising a Czerny Turner monochromator with multichannel CCD detector). Each spectrometer covers a preselected, non-overlapping, wavelength region. The array of spectrometers is operable to acquire spectral data synchronously from each ablation. The embodiments have an advantage of being able to capture broadband spectral information in a wide range of wavelengths. For example, an operable range of wavelengths can be 190 nm-1040 nm, although a narrower range can be preferable for greater resolution, depending on the application. In some embodiments there can be overlapping spectrometer wavelength regions. A partially overlapping wavelength region can be useful to calibrate the response of the different spectrometers regions with respect to one another using regions of overlap.

The various detectors and monochromators/spectrographs have advantages and disadvantages with respect to one another. For example, while a CCD detector is generally less sensitivity than an ICCD, CCD technology is relatively inexpensive in comparison to an ICCD having an equivalent number of channels. A CCD detector is well suited for broadband analysis. Besides having less sensitivity, another limitation of CCD detector arrays is that they cannot be gated on and off in very short intervals to discriminate against continuum emission and/or other interference.

In the analysis of unknown samples, a broadband CCD spectrometer and/or array of spectrometers can be first used to survey the principal elements that are present, and identify the elements present in majority, minor, and/or trace concentration levels. After a sample is characterized using a broadband optical spectrometer (such as one comprising a CZ-ICCD or CZ-CCD combination), higher resolution lower intensity spectral data obtained from a high resolution, lower sensitivity spectrometer and/or plurality of high resolution/high sensitivity spectrometers in an array can be provide trace element analysis. As disclosed above, various embodiments can acquire both broadband and low intensity, high resolution spectroscopic data from a single ablation plume simultaneously.

Recently, laser induced breakdown spectroscopy (LIBS) at low pressure has been used for isotopic analysis. The majority of this work has focused on the analysis of atomic species. In general, to detect separate emission lines arising from different isotopes, the width of an elemental atomic spectral line has to be quite narrow before different isotopes can be resolved from one another and distinguished from emissions arising from different elements. For example, the uranium II line emission at 424.437 nm has a U-238/235 isotope shift of 0.025 nm and the Pu I emission line at 594.522 nm has a Pu-239/240 isotope shift of 0.0125 nm. By comparison, the width of a Si 288 nm line is on the order of 1 $cm^{-1}$ when electron number density is in the range of about $10^{17}$ $cm^{-3}$. LIBS plasmas induced in an ambient pressure environment generally have an electron number density well above this value. The width of an emission line in a LIBS plasma decreases with temperature and the number density of gas and electrons.

For these reasons, most attempts to detect different isotopes using LIBS have depended on lowering pressure to a degree necessary to sufficiently reduce both Doppler and Stark broadening (e.g. to ~0.01 nm or less for U-238/235 or Pu-239/240). The requirement of having a vacuum LIBS chamber can obviate many advantages of LIBS since a suitable loadlocked and/or pumped vacuum chamber and pumps are relatively large, heavy, mechanically complex, and not field portable.

Furthermore, when LIBS is performed at low pressures, the laser induced plasma expands far more rapidly relative to an atmospheric pressure environment and the corresponding plasma electron number density decreases more rapidly. Attempts to detect isotopes using LIBS at atmospheric pressure have been limited by broadened and/or unresolved atomic and ionic spectra that severely impaired the ability to measure isotopic abundance ratios.

Figure 14:
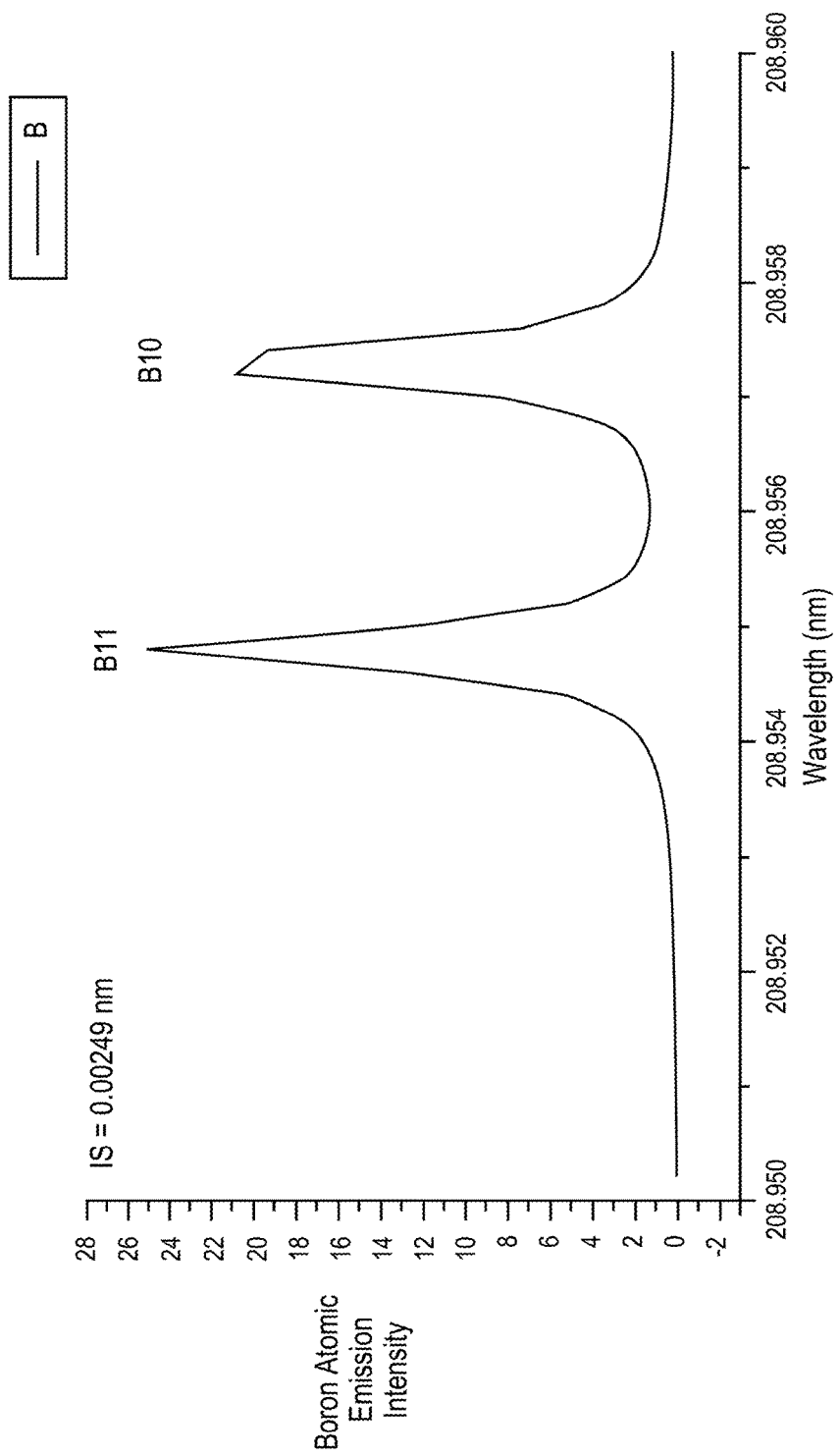
FIG. 14 shows an example of a spectrum showing boron isotope splitting at the appropriate wavelength.

Characteristic features emanating from molecular spectra, on the other hand, can have an isotopic shift magnitude of an isotopic shift that is orders of magnitude larger than seen in atomic spectra. For example, the isotopic shift of atomic boron (B) at 208.889 nm is 0.0025 nm, as shown in FIG. 14. The isotopic shift of atomic boron (B) is almost 3 orders of magnitude less than of molecular boron (e.g., BO). Further details regarding LIBS methods and LIBS systems may be found in U.S. Pat. No. 8,199,321, which is herein incorporated by reference.

In fact atomic species from a sample can be embedded into molecular species during the laser ablation process in various ways. For example, when a laser induced plasma is produced in the presence of oxygen and/or ambient air, an elemental atom arising from ablated sample material may react ambient oxygen to form an oxide species. The use of LIBS techniques to detect isotopes believed to require low pressure environments where Doppler and Stark broadening are greatly reduced. Previous isotope detection using LIBS, even when based on molecular spectral features, was performed in a low pressure sub-atmospheric environment.

Embodiments disclosed below herein provide a method of performing isotopic analysis of a sample. Such a method of performing isotopic analysis of a sample may be referred to as Laser Ablation Molecular Isotopic Spectrometry (LA-MIS) in the scientific literature. Embodiments disclosed herein provide techniques for isotopic analysis that: (i) may be carried out under atmospheric conditions in the ambient environment (e.g., ambient air); (ii) can be applied to wide range of sample types (i.e., any kind of sample); (iii) may have a high throughput (i.e., rapid analysis of many samples with a high speed of analysis); (iv) may have good discrimination; (v) may have good sensitivity (e.g., down to ppm levels or less); (vi) may require minimal sample preparation or no sample preparation; (vii) may have stand-off capability; and (viii) can be used with a numerical (e.g., Partial Least Squares (PLS), multivariate) algorithm for analysis of data.

In some embodiments, the sample may be in a solid phase or a liquid phase (i.e., the sample may be condensed matter). In some embodiments, the sample may be in a gas phase. In some embodiments, the sample may be an aerosol; an aerosol is a suspension of fine solid particles or liquid droplets in a gas.

Figure 15:
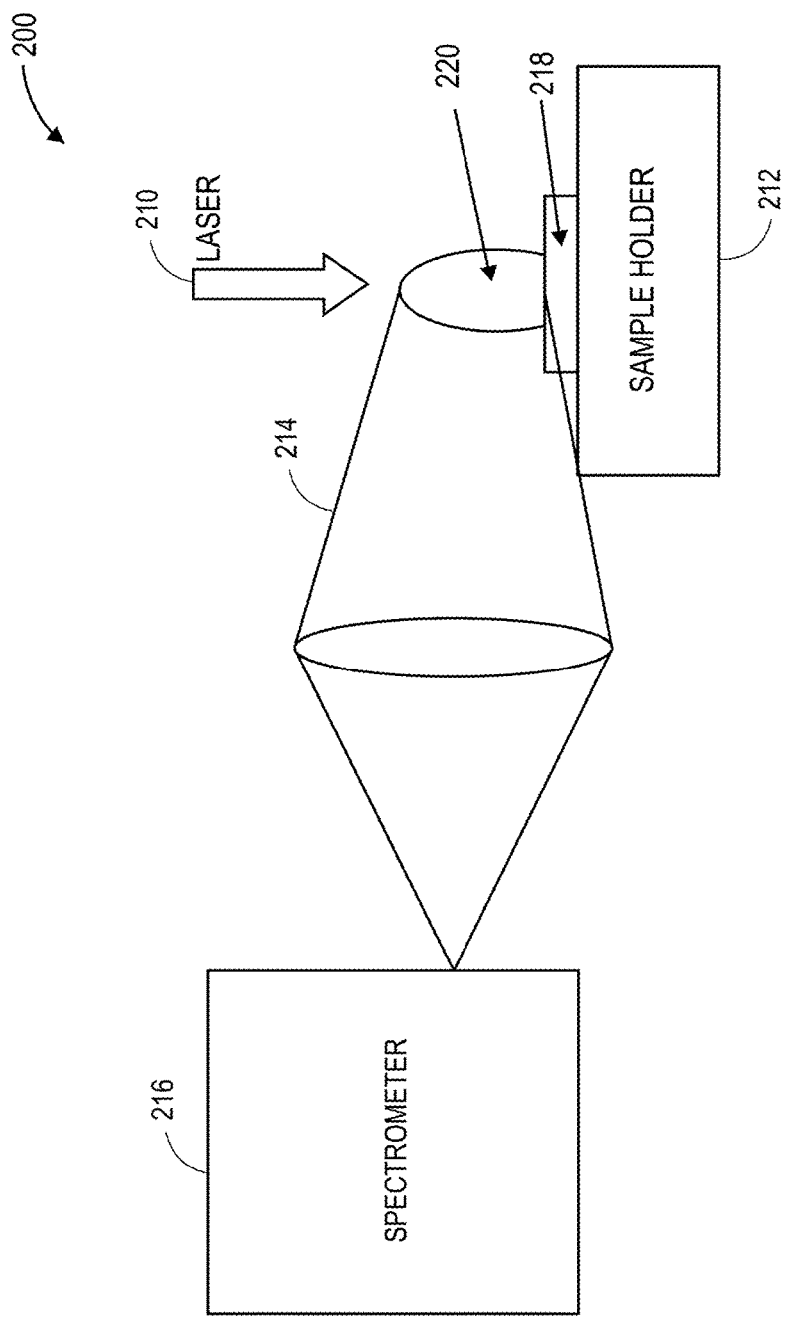
FIG. 15 shows an example of a schematic diagram of an apparatus.

Referring to FIG. 15, in some embodiments an apparatus 200 includes a laser 210, a sample holder 212, an emission collection system 214, and a spectrometer 216. The sample holder 212 is configured to hold a sample 218. The laser 210 is configured to apply laser energy to the sample 218 and generate a plasma 220. The emission collection system 214 is configured to collect optical or electromagnetic emissions from the plasma 220 that may then be input to the spectrometer 216.

In some embodiments, the spectrometer 216 may be operable to detect electromagnetic radiation of a wavelength of about 200 nanometers (nm) to 900 nm. For example, the spectrometer 216 may be operable to detect intensity and wavelength values of the electromagnetic radiation. In some embodiments, the emission collection system 214 may include collection optics configured to receive light from the plasma 220 and a fiber optic cable operable to transmit the light from the collection optics to the spectrometer 216. In some embodiments, a detector that is included as part of the spectrometer may include an intensified charge coupled device (ICCD), a charge-coupled device (CCD), or a photomultiplier tube (PMT).

Figure 16:
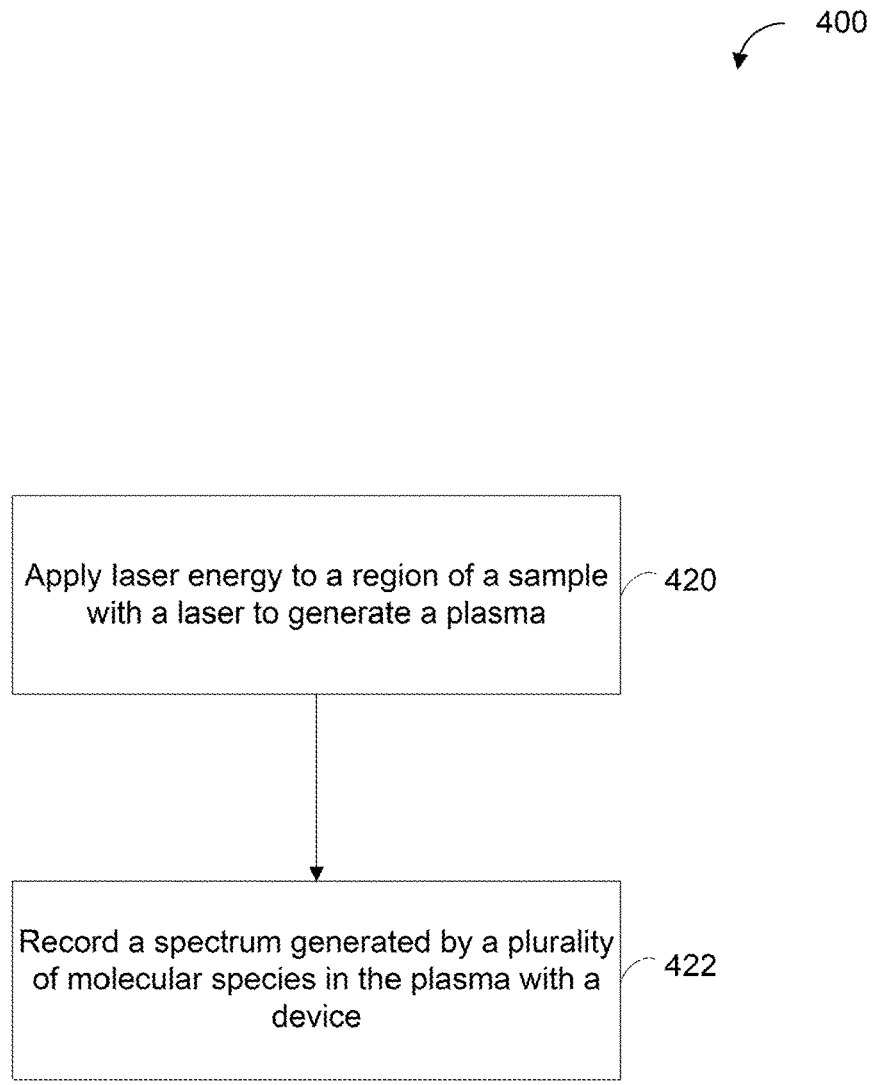
FIG. 16 shows an example of a flow diagram for performing Laser Ablation Molecular Isotopic Spectrometry (LAMIS).

Referring to FIG. 16, in some embodiments a method 400 may be performed with the apparatus 200. Starting with operation 420 of the method 400, laser energy is applied to a region of a sample with a laser to generate a plasma. In some embodiments, the sample may be in a solid phase, a liquid phase, or a gas phase. In some embodiments, the sample may be an aerosol. In operation 422, a spectrum generated by a plurality of molecular species in the plasma is recorded with a spectrometer or other device. For example, with the apparatus 200 shown in FIG. 15, the ablation laser 210 may be used to generate a plasma from the sample, and the emission collection system 214 and the spectrometer 216 may be used to record the spectrum generated by the plurality of molecular species. The spectrometer 216 may detect electromagnetic information (e.g., light) generated by the plasma.

In some embodiments, the laser energy may be applied to the region of the sample in a pulse of laser energy. Any laser wavelength, laser energy, and laser pulse width may be used in operation 420, as long as a plasma is generated. In some embodiments, the laser wavelength may be about 1064 nanometers (nm), the laser energy may be about 50 millijoules (mJ) to 100 mJ, and the laser pulse width may be about 4 nanoseconds (ns). For example, a neodymium doped yttrium aluminum garnet (Nd:YAG) laser may be used to generate energy in the near infrared region of the electromagnetic spectrum with a wavelength of 1064 nm. With a pulse duration of about 4 ns, a laser beam with a power density of greater than one GW/cm2 at the laser beam focal point can be formed. In some embodiments, the pulse duration can be decreased to femtoseconds. In some embodiments, the laser beam can be focused to a spot size of about 10 micrometers to 500 micrometers, or about 150 micrometers to 200 micrometers.

In some embodiments, operation 420 may include ablating the sample with the applied laser energy. Such a process may be referred to as laser ablation or ablation.

In some embodiments, operation 420 may include vaporizing the sample with the applied laser energy. In some embodiments, operation 420 may include desorbing the sample with the applied laser energy. In some embodiments, when operation 420 includes vaporizing the sample or desorbing the sample with the applied laser energy, a plasma may not be formed with the applied laser energy. In these embodiments, the method 400 may further include imparting additional energy to the vaporized or desorbed sample to form a plasma including the plurality of molecular species.

In some embodiments, additional energy may be imparted to the plasma. The additional energy may cause molecular species in the plasma to produce additional optical or electromagnetic emissions that can be detected with the spectrometer. In some embodiments, such additional energy may be imparted to the plasma by preforming operation 420 in a microwave field or a radio frequency (RF) field. In some embodiments, such additional energy may be imparted to the plasma with an additional pulse of laser energy. For example, in some embodiments, operation 420 may include applying a first pulse of laser energy at a first angle with respect to the sample, and then applying a second pulse of laser energy at a second angle with respect to the first angle. In some embodiments, the second angle may be about 0 degrees to 90 degrees with respect to the first angle.

The plasma may include ionic, atomic, and molecular species. In some embodiments, the plasma, immediately after application of the laser energy in operation 420, may include a molecular species or a plurality of molecular species. In some embodiments, species atomized from the sample may react with each other to form a molecular species or a plurality of molecular species. The molecular species may include diatoms (e.g., $Na_2$, $C_2$) or excimers (e.g., $He_2$, $Xe_2$, and XeCl), for example.

In some embodiments, the plasma may be allowed to react with species in the surrounding environment to form a molecular species. For example, operation 420 may be performed in ambient air under ambient pressure. Species in the plasma may react with oxygen or nitrogen, for example, in the air to form oxide molecular species or nitride molecular species, respectively. Whether the as-formed plasma includes molecular species depends in-part on the laser wavelength, the laser pulse duration, the laser power, the laser spot size, and the laser fluence. When the plasma is allowed to react with species in the surrounding environment to form a molecular species, the time needed for such a reaction or reactions also depends in-part on the laser wavelength, the laser pulse duration, the laser power, the laser spot size, the laser fluence, the sample, and the molecular species.

The recording of a spectra generated by molecular species (i.e., molecular emission) versus recording a spectra generated by atomic species (i.e., atomic emission) is one difference between the embodiments disclosed herein (e.g., LAMIS) and the laser induced breakdown spectroscopy (LIBS) technique. Generally, in LIBS a spectrum is recorded after laser energy is imparted to a sample (e.g., a short delay of about 1 microsecond or less) to reduce or minimize spectral line broadening and the background. The delay time depends in part on the laser energy and the sample.

In some embodiments, a period of time between operations 420 and 422 is set or specified to increase or maximize the intensity of molecular emission and to decrease or minimize atomic emission and ionic emission (i.e., emission from atoms and atomic ions). Again, this period of time depends in part on the laser wavelength, the laser pulse duration, the laser power, the laser spot size, the laser fluence, the sample, and the molecular species.

As noted above, in operation 422, optical or other electromagnetic emission generated by the plasma may be recorded by a spectrometer or other device. In some embodiments, operation 422 includes recording the spectrum with visible spectroscopy, recording the spectrum with ultraviolet spectroscopy, recording the spectrum with infrared spectroscopy, or recording the spectrum with near-infrared spectroscopy. In some embodiments, operation 422 includes recording direct optical emission of the plurality of molecular species, recording optical absorption of the plurality of molecular species, recording induced fluorescence of the plurality of molecular species, recording Raman scattering of the plurality of molecular species, recording luminescence of the plurality of molecular species, recording phosphorescence of the plurality of molecular species, recording photoacoustics of the plurality of molecular species, or recording photoionization of the plurality of molecular species.

In some embodiments, the method 400 may be performed more than once or a plurality of times on the same region of the sample. The recorded spectrum for each repetition of the method 400 may then be averaged. For example, in some embodiments, the method 400 may be repeated two times or three times on a region of a sample. Performing the method 400 on the same region of the sample multiple times and averaging the results may yield a spectrum with less noise and less experimental error.

In some embodiments, the method 400 shown in FIG. 16 may further include quantifying the abundance of isotopes of an element in the sample. As known by one of ordinary skill in the art, isotopes of an element all have the same number of protons. Isotopes, however, differ from each other by having different numbers of neutrons. Different elements have different numbers of isotopes; some elements have one isotope, but most elements have more than one isotope.

Figure 17:
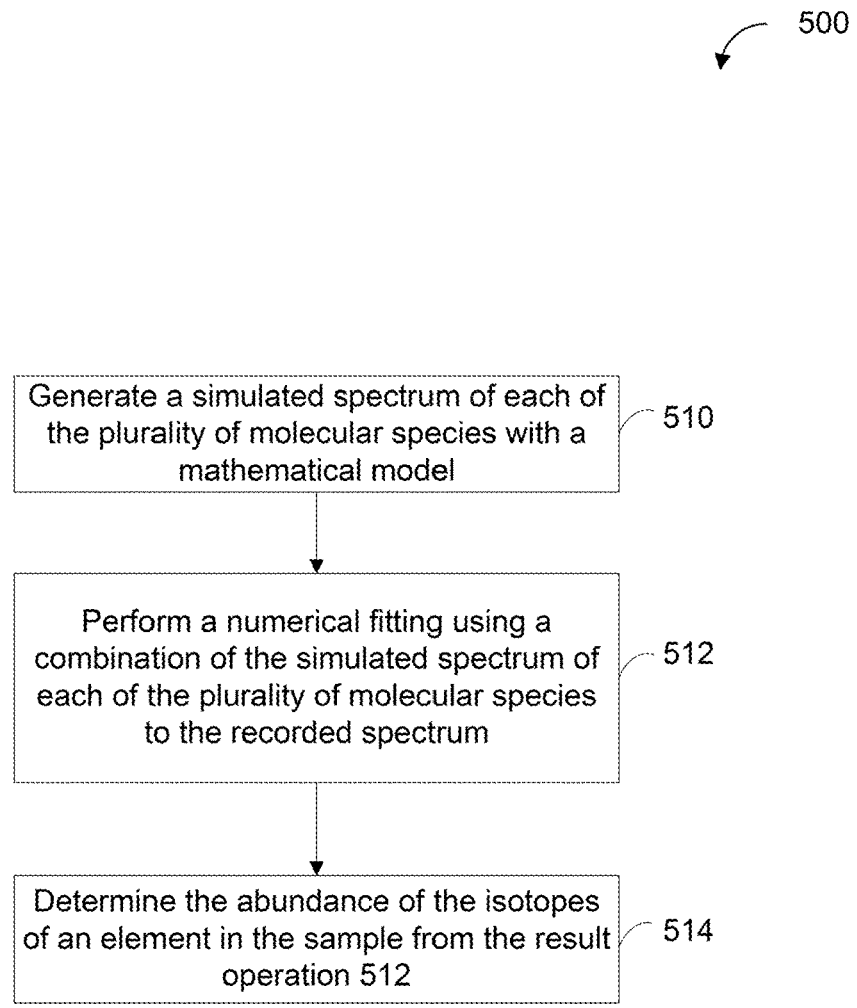
FIG. 17 shows an example of a flow diagram for quantifying the abundance of isotopes in a sample.

Referring to FIG. 17, a method 500 of quantifying the abundance of isotopes in the sample starts with operation 510. In operation 510, a simulated spectrum of each of the plurality of molecular species in the plasma is generated with a mathematical model. In operation 512, a numerical (e.g., least squares) fitting of the simulated spectrum of each of the plurality of molecular species to the recorded spectrum is performed. In operation 514, the abundance of the isotopes of an element in the sample from the result of operation 512 is determined.

For example, in a sample having two isotopes of an element, the recorded spectrum may be fit with the simulated spectrum of each isotope of the element by varying the fraction of each isotope when performing a least squares fitting. That is, each simulated spectrum is multiplied by a percentage (with the percentages adding up to 100%) and the resulting simulated spectra are summed; the percentages are varied to best match the sum of the simulated spectra to the measured spectrum. The percentage assigned to each simulated spectra is the percentage of each isotope of the element in the sample. Experimental results of such a procedure, including a mathematical model which may be used to simulate the spectra of the molecular species, are described below in EXAMPLE 1.

In some embodiments, operation 510 includes simulating the spectrum of each of the molecular species for direct optical emission, simulating the spectrum of each of the molecular species for optical absorption, simulating the spectrum of each of the molecular species for induced fluorescence, simulating the spectrum of each of the molecular species for Raman scattering, simulating the spectrum of each of the molecular species for luminescence, simulating the spectrum of each of the molecular species for phosphorescence, simulating the spectrum of each of the molecular species for photoacoustics, or simulating the spectrum of each of the molecular species for photoionization.

In some embodiments, instead of simulating the spectrum of each of the plurality of molecular species in operation 510, spectra from samples with a known abundance of isotopes may be recorded. For example, samples with a known abundance of isotopes may be obtained from an agency such as the National Institute of Standards and Technology (NIST). These recorded spectra, instead of simulated spectra, may be used in the numerical fitting procedure of operation 512.

In some embodiments, both simulated spectra and recorded spectra are used to calibrate a system. In some embodiments, a multivariate calibration may be performed. In some embodiments, a multivariate calibration may include recording spectra from a plurality of samples, each of the samples having a known but different abundance of isotopes. These recorded spectra may be used to determine isotope ratios in a sample having an unknown abundance of isotopes.

For example, a partial least squares (PLS) linear regression routine may be used to match a spectrum of an unknown sample to one of the reference spectra. The PLS routine may be applied to obtain a multivariate calibration that takes into all intensities at most or every pixel within the wavelength range of interest. This multivariate calibration is different from the traditional univariate calibration, which is usually built using only one pre-selected spectral line (or other single spectral feature) at a specific wavelength. In some embodiments, the multivariate approach is more accurate, robust, and reliable in comparison to univariate calibration. Further, multivariate calibration can be performed correctly even when spectra are only partially resolved; this aspect is particularly important for molecular spectra.

In some embodiments, the method 400 shown in FIG. 16 and the method 500 shown in FIG. 17 may be performed on a different region of the sample. By doing this, variations in the abundance of an isotope or isotopes in different regions of the sample may be determined.

Figure 18:
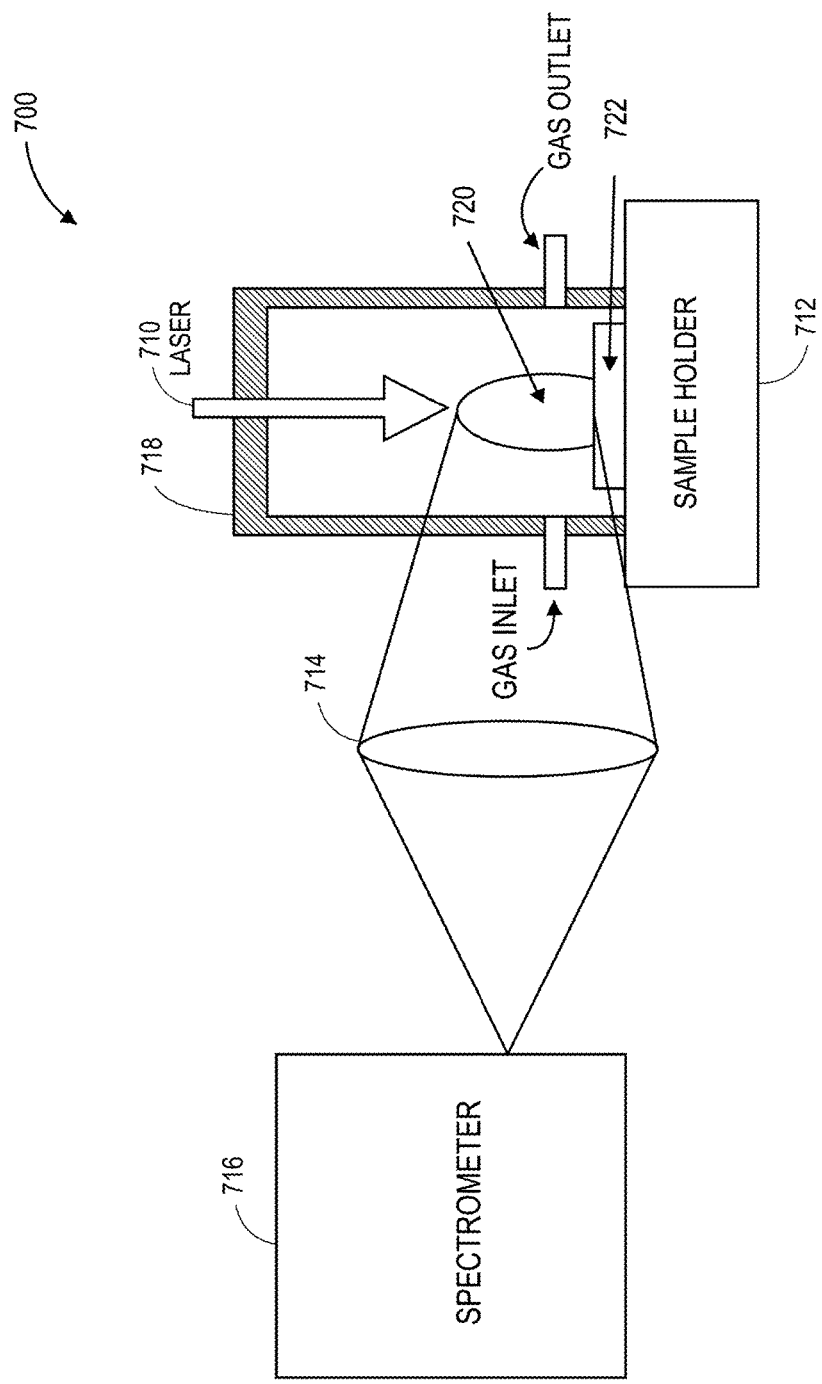
FIG. 18 shows an example of a schematic diagram of an apparatus.

Referring to FIG. 18, in some embodiments an apparatus 700 includes a laser 710, a sample holder 712, an emission collection system 714, a spectrometer 716, and a chamber 718. The sample holder 712 is configured to hold a sample 722. The laser 710 is configured to apply laser energy to the sample 722 and generate a plasma 720. The emission collection system 714 is configured to collect optical or electromagnetic emissions from the plasma 720 that may then be input to the spectrometer 716.

The chamber 718 may contain a specific gas or gasses at a specific pressure or pressures. The gas or gasses may be specified, depending on the sample being analyzed, such that desired molecular species may be formed that aid in quantifying the abundance of isotopes in the sample. For example, a gas may be selected such that the spectra formed by two molecules, each including a different isotope of an element, in the sample have an isotopic spectral shift that is able to be resolved by the spectrometer being used. Further, the sample inside the chamber may be held at a specific temperature. When a sample is held at one temperature versus a different temperature, different molecular species may be formed in the plasma. Using such an apparatus 700, some control over molecular species formed when the plasma reacts with the environment may be achieved; i.e., by controlling the plasma properties, the formation of specific molecules can be controlled.

In some embodiments, to control the gas or gasses with which the plasma may react, the chamber 718 may not be used. Instead, in some embodiments, tubes or other devices may be used to deliver a gas to the region where the plasma is to be formed.

Figure 19:
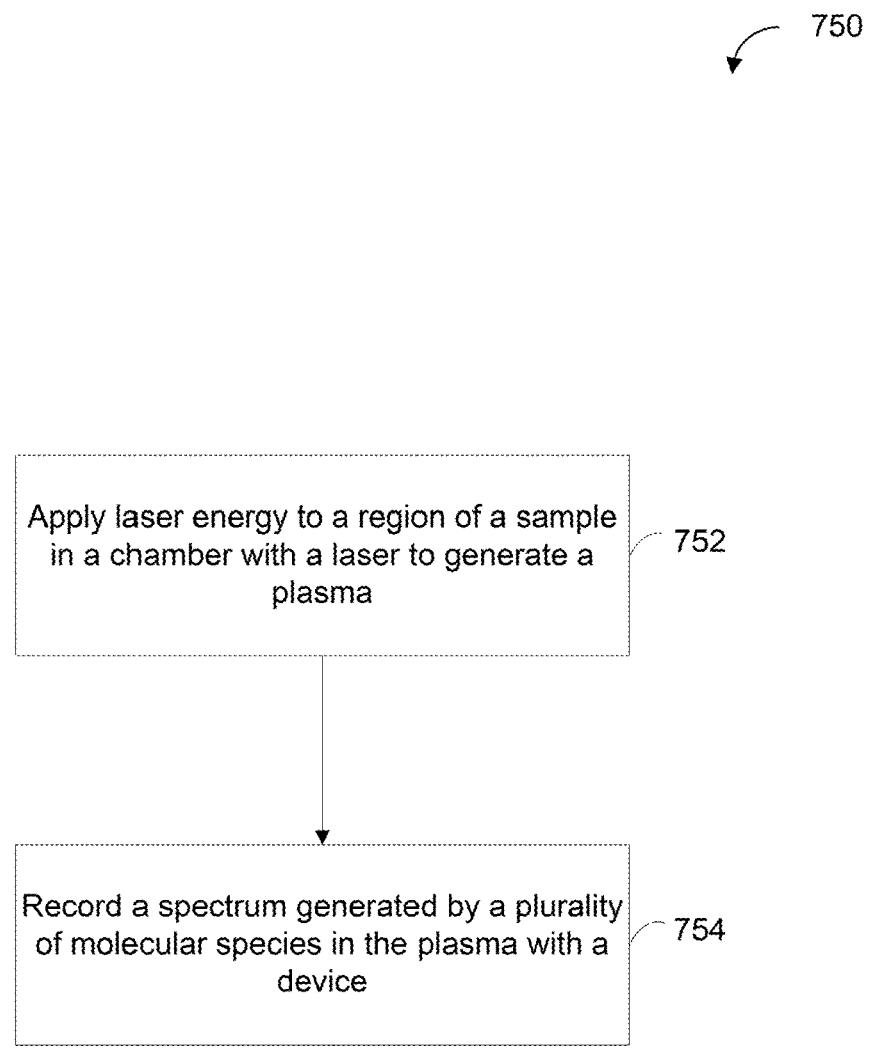
FIG. 19 shows an example of a flow diagram for performing LAMIS.

Referring to FIG. 19, in some embodiments a method 750 may be similar to the method 400 shown in FIG. 16. Starting with operation 752 of the method 750, laser energy is applied to a region of a sample with a laser to generate a plasma. The plasma generated in operation 752 may be generated in the chamber 718 of the apparatus 700. The chamber 718 may contain a specific gas or gasses at a specific pressure or pressures. In operation 754, a spectrum generated by a plurality of molecular species in the plasma is recorded with a spectrometer or other device.

Figure 20:
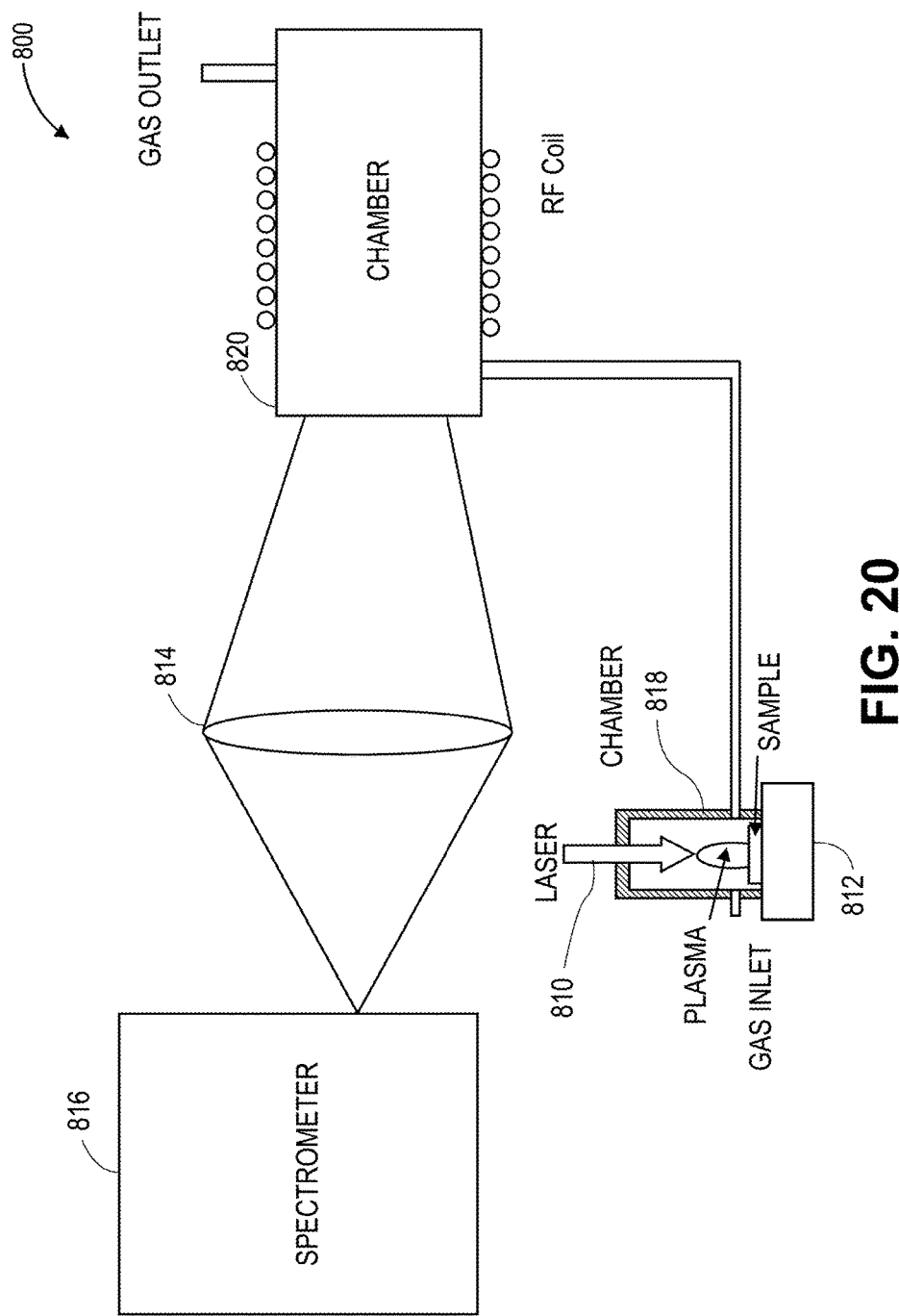
FIG. 20 shows an example of a schematic diagram of an apparatus.

Referring to FIG. 20, in some embodiments an apparatus 800 includes a laser 810, a sample holder 812, an emission collection system 814, a spectrometer 816, a first chamber 818, and a second chamber 820.

Figure 21:
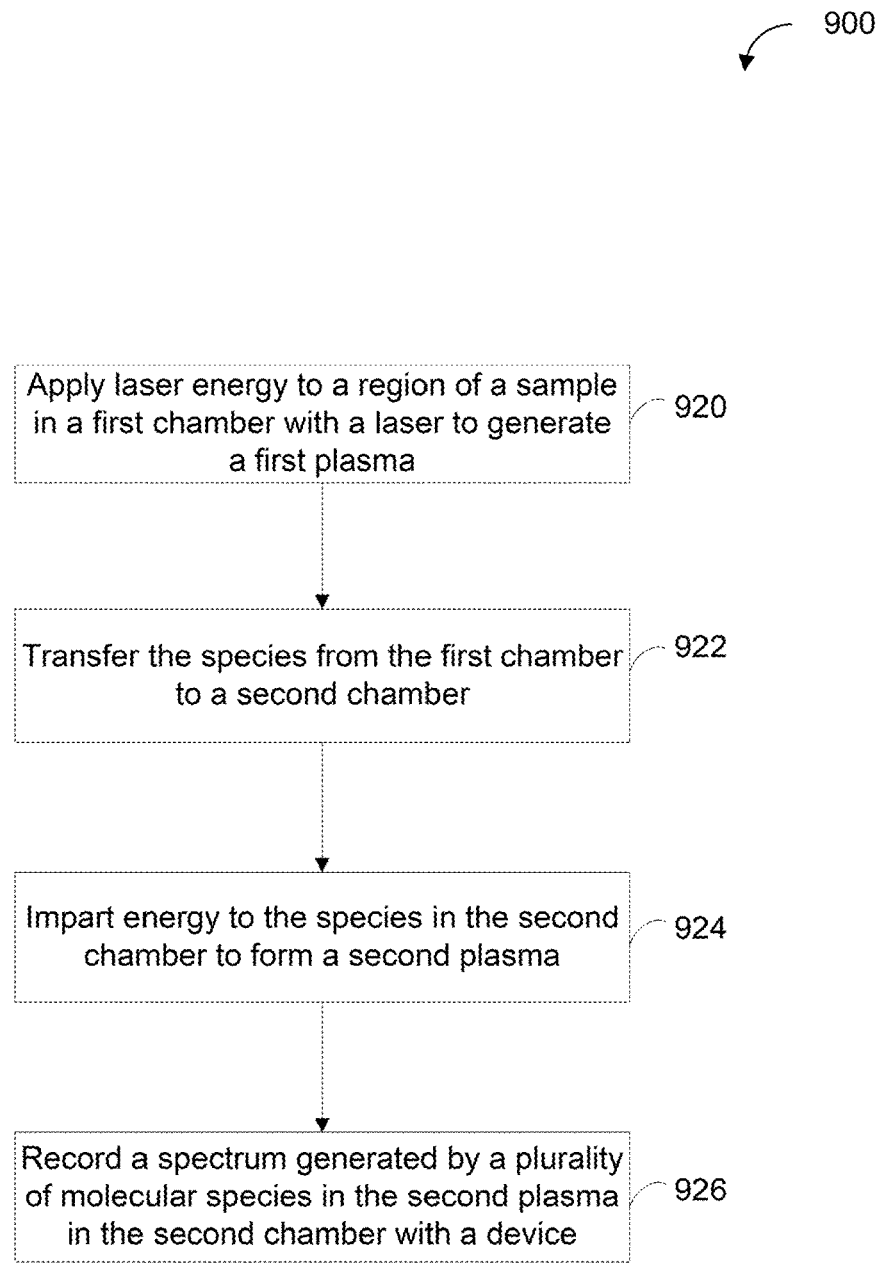
FIG. 21 shows an example of a flow diagram for performing LAMIS.

Referring to FIG. 21, in some embodiments a method 900 may be similar to the method 400 shown in FIG. 16. Starting with operation 920 of the method 900, laser energy is applied to a region of a sample in a first chamber with a laser to generate a first plasma. For example, the plasma generated in operation 920 may be generated in the first chamber 818 of the apparatus 800 shown in FIG. 20. The first chamber 818 may contain a specific gas or gasses at a specific pressure or pressures. The plasma may react with the specific gas or gasses to form a species.

In operation 922, the species may be transferred from the first chamber to a second chamber. For example, the species may be transferred from the first chamber 818 to the second chamber 820 of the apparatus 800 shown in FIG. 20. In operation 924, energy is imparted to the species in the second chamber to form a second plasma. In operation 926, a spectrum generated by a plurality of molecular species in the second plasma is recorded with a spectrometer or other device.

The apparatus 800 may allow for more control of the second plasma in the second chamber 820. For example, a second plasma in the second chamber may be more stable (e.g., it may last for a longer time period). Further, a second plasma in the second chamber may be under conditions that are more favorable to form a desired molecular species.

In some embodiments, additional energy may be imparted to the plasma in the first chamber. In some embodiments, additional energy may be imparted to the plasma in the second chamber. As noted above with respect to FIG. 16 the additional energy may cause molecular species in the plasma to produce additional optical or other electromagnetic emissions that can be detected with the spectrometer. In some embodiments, such additional energy may be imparted to the plasma with a microwave field, a RF field, or an additional pulse of laser energy.

In some embodiments, the methods 400 (described with respect to FIG. 16), 750 (described with respect to FIG. 19), and 900 (described with respect to FIG. 21) may all be followed by the method 500 (described with respect to FIG. 17) to quantify the abundance of isotopes of an element in a sample. Further, in some embodiments, the details described with respect to the method 400 may be applicable to the methods 750 and 900.

Another aspect of the embodiments disclosed herein is an apparatus with a system controller configured to accomplish the methods described herein. For example, a suitable apparatus includes hardware for accomplishing the process operations and a system controller having instructions for controlling process operations in accordance with the disclosed embodiments. Hardware for accomplishing the process operations may include an energy source (e.g., a laser), a sample holder, an emission collection system, and a spectrometer coupled to a detector. The system controller will typically include one or more memory devices and one or more processors configured to execute the instructions so that the apparatus will perform a method in accordance with the disclosed embodiments. Machine-readable media containing instructions for controlling process operations in accordance with the disclosed embodiments may be coupled to the system controller. The embodiments disclosed herein are described below in greater detail by way of specific examples. The following examples are offered for illustrative purposes, and are intended not to limit the invention in any manner.

Example 1

It has been demonstrated that by analyzing optical molecular emission from the plasma, signal could be discriminated from different isotopes that were present in the sample. The laser wavelength in this example/experiment was 1064 nm, the laser energy was 100 mJ, and laser pulse width was 4 ns. However, any laser wavelength, energy, and pulse width could be used as long as it generates a plasma. In this experiment, an Intensified Charge Coupled Device system (ICCD) was coupled to the spectrometer for the detection of plasma optical emission.

Molecular electronic transition wavelength depends on the difference of two electronic states and can be calculated, for example, using the following formula:

$$v = T' - T'' = (T'_e - T''_e) + (G' - G'') + (F' - F'') \quad (1)$$

where the single primed letters refer to the upper state and double primed letters refer to the lower state. Te is electronic energy, G is the vibrational energy, and F is the rotational energy. G is a function of the vibrational quantum number v and F is a function of the rotational number J:

$$G = \omega_e\left(v + \frac{1}{2}\right) - \omega_e x_e\left(v + \frac{1}{2}\right)^2 + \omega_e y_e\left(v + \frac{1}{2}\right)^3 + \ldots \quad (2)$$

$$F = B_v J(J+1) - D_v J^2(J+1)^2 + \ldots$$

For different molecular isotopes, the vibrational and rotational energies are a function of $$\rho = \sqrt{\frac{\mu}{\mu^i}}$$

where $\mu$ is the reduced mass of molecule and i denotes the isotope:

$$w^i_e = \rho w_e \quad w^i_e x^i_e = \rho^2 w_e x_e \quad B^i_v = \rho^2 B_v \quad (3)$$

Equations 1-3 can be used to calculate spectral shifts—also known as isotopic shift—for differential molecular isotopes.

For isotope detection, the isotopic shift (IS) of vibrational band head or the rotational line positions can be used. For vibrational band head difference, IS is given by:

$$\Delta v = (1-\rho)\left[\omega'_e\left(v' + \frac{1}{2}\right) - \omega''_e\left(v'' + \frac{1}{2}\right)\right] - \quad (4)$$
$$(1-\rho^2)\left[\omega'_e x'_e\left(v' + \frac{1}{2}\right)^2 - \omega''_e x''_e\left(v'' + \frac{1}{2}\right)^2\right]$$

According to Eq. 4, IS is large if the difference between quantum number v is also large. When choosing vibrational band head for isotopic detection, the largest differential of v number with a reasonable emission intensity should be used.

Figure 22:
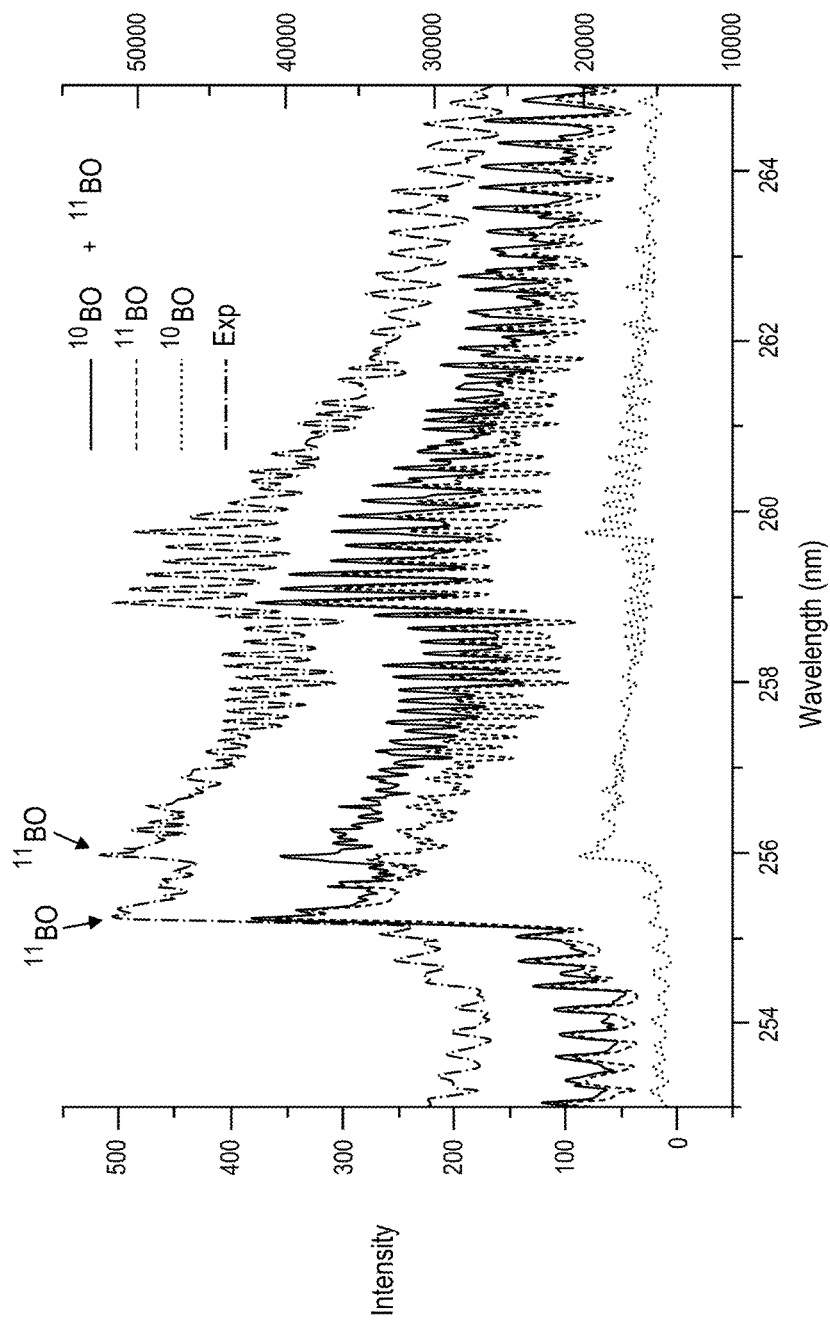

FIG. 22 shows the vibrational band head positions for 10BO and 11BO and demonstrates the large molecular isotopic shift. The dashed/dotted line plot is the experimental data. The dashed and dotted plots are the calculated emission spectra (e.g., using equations (1)-(3)) for $^{11}$BO and $^{10}$BO, respectively. The solid line plot is the combination of $^{11}$BO and $^{10}$BO calculated emission spectra. The emission spectra in FIG. 10 represents transitions of the $B^2\Sigma^+$ (v=0)→$X^2\Sigma^+$ (v=2) electronic system of boron monoxide corresponding to transitions from v'=0 of the upper electronic state, $B^2\Sigma^+$, to v''=2 of the ground electronic state, $X^2\Sigma^+$. Such a transition is referred to as the (0, 2) band of the $B^2\Sigma+→X^2\Sigma^+$ system. The isotope shift for this band is 0.73 nm.

Compared to the atomic IS (e.g., see FIG. 14), the molecular IS is greatly enhanced. The IS of $B^2\Sigma^+$-$X^2\Sigma^+$ (0'-3") is even large (1.14 nm). The emission intensity, however, is weaker. For the B-O $B^2\Sigma^+$-$X^2\Sigma$ Band, the (0-2) band is the best for boron monoxide isotope detection.

For isotope detection, the rotational structure also can be used. The isotope shift for rotational energy is:

$$\Delta F = (1-\rho^2)[B_v J'(J'+1) - B_v J''(J''+1)] \quad (5)$$

IS, according to Eq. 5, depends on both vibrational quantum and rotational quantum numbers. From Eq. 5, the isotopic shift from rotation band also increases with J and v. A wide range of rotational structure from 350 nm to 700 nm can be used detect isotopes.

The results presented in FIG. 22 demonstrate the isotopic detection capabilities using molecular emission. Such data can be used to quantify the concentration of isotopes. One way is to fit the calculated emission spectra to the experimental data.

For example, the experimental data presented in FIG. 22 were fitted in order to determine the isotopic concentration. Using a least squares fitting technique, the experimental data was fitted by allowing the isotopic fraction to vary.

Figure 23:
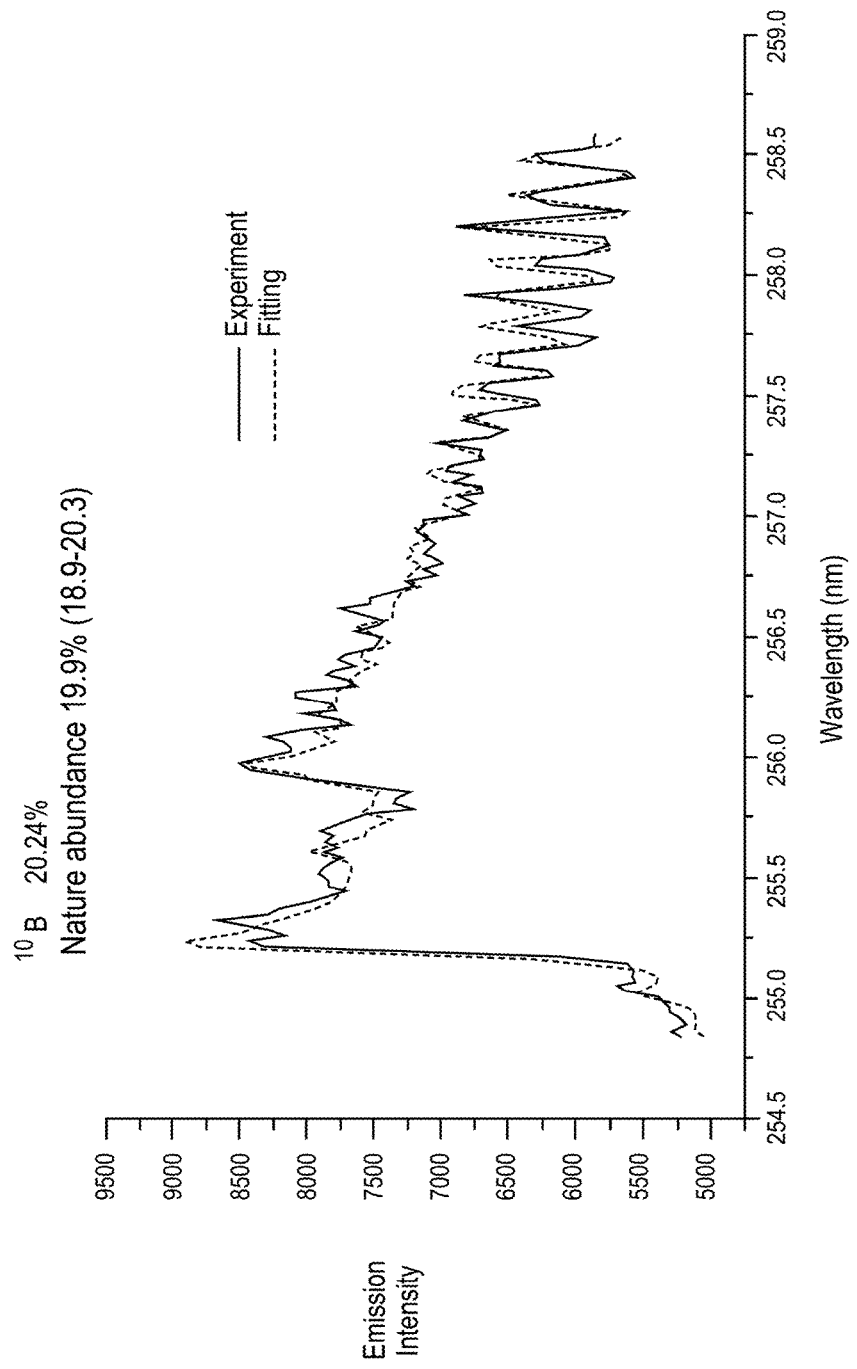

FIG. 23 shows the experimental data (solid) and fitted calculated curve (dashed). The least squares fit resulted in concentration of 20.2% for 10B. The natural abundance of 10B is 19.9%, which is very close to the calculated result. These results demonstrate that least squares fitting could provide quantitative isotopic information.

The embodiments disclosed herein were further demonstrated by using emission of diatomic molecules, such as OH, CN, $C_2$, BO, and SrO. This method can also be applied to other samples.

Example 2

Samples with known boron isotopic ratio were ablated using a Nd:YAG laser with wavelength 1064 nm, a pulse energy of 50 mJ to 100 mJ, and a pulse duration of 4 ns. The laser beam was focused onto the sample with a quartz lens to a spot diameter of about 100 micrometers (μm). A second lens was used to collect the laser-induced plasma emission onto the entrance of a fiber optic cable coupled to a Czerny-Turner spectrometer with an Intensified Charge-Coupled Device (ICCD). The signal acquisition delay after the laser pulse was varied to demonstrate the relative intensities for atomic, ionic, and molecular emission. The spectra represent accumulation of single or multiple laser pulses; the number of pulses for each measurement is noted in the figure descriptions. Additional measurements were performed at different spectral resolutions by changing the entrance slit width of the spectrometer. The spectral resolution was determined by measuring the full width at half maximum (FWHM) of the Hg line. All measurements were performed in air at atmospheric pressure.

A double-pulse setup of some embodiments consisted of two lasers and a detection system. The wavelength of the ablation laser was 355 nm, and its pulse energy was 8.5 mJ. The second laser's wavelength was 1064 nm with a pulse energy of 75 mJ. The second laser propagated orthogonal to the first ablation laser. The time delay between the two laser pulses was 2.4 microseconds (μs). The second laser pulse was focused inside the first laser induced plasma at a height approximately 1 millimeter (mm) above the sample surface. The ICCD acquired spectra at 8 μs delay after the ablation laser. The gated acquisition time was 30 μs. In some embodiments, the pulse could include laser energy, microwave energy, or a spark.

Boron nitride (BN) pressed-powder disks with natural isotopic abundance were used as samples. These BN disks were commercial sputtering targets designed for film deposition in the electronics and optical industry (obtained from Alfa Aesar (Ward Hill, Mass.), 99.99% purity). Additionally, isotope-enriched samples of $^{10}B_2O_3$ and $^{11}B_2O_3$ (99% $^{10}B$ and 95% $^{11}B$) were used as reference standards. The boron oxide samples were purchased from Cambridge Isotope Laboratories, Inc. (Andover, Mass., USA). To prepare the different isotope ratio boron oxide reference samples, different amounts of isotope-enriched $B_2O_3$ were mixed and then pressed with a 7 ton pressure for 4 minutes into one-centimeter diameter pellets.

It has been demonstrated that isotopic shifts can be orders of magnitude larger in molecular versus atomic optical emission. In some embodiments, an ablating laser pulse is impinged on the sample surface that results in explosive vaporization, atomization, and partial ionization of matter from the sample and surrounding air. After the plasma in a plume cools down sufficiently, the molecular radicals form. In particular, the diatomic oxide radicals form when atoms evaporated from the sample react with dissociated atmospheric oxygen. A small deviation in plasma chemistry of different isotopes of the same element may occur, but in general all isotopes undergo very similar reactions. Quantitative calibration then relates the measured spectra of radicals in an ablation plume to the original abundances of isotopes in the sample.

Figure 24:
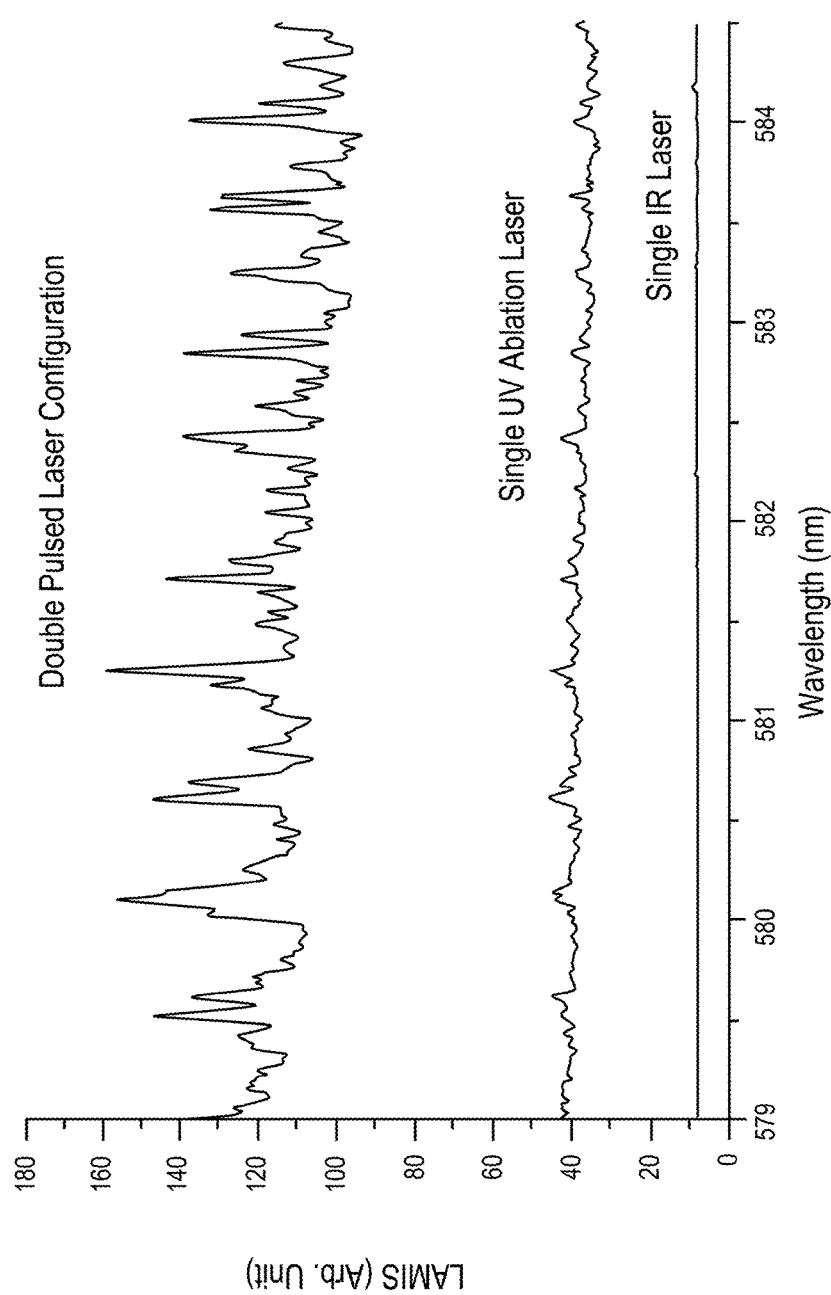

The double-pulse approach, according to some embodiments, in which a second laser pulse is coupled into a laser plasma with a short delay after the first pulse, has been shown to increase atomic and ionic emission. Similar enhancements were measured for molecular emission as shown in FIG. 24. The ablated mass in both double-pulse and single-pulse measurements was the same. Therefore, enhancement in intensity of molecular spectra can be attributed to higher electronic and collisional excitation of molecules in the double-pulse approach. However, it is clear from these data that sensitivity could be increased.

FIG. 24 shows BO emission spectra from laser ablation of the BN sample measured in the double-pulse scheme. The bottom trace shows the effect of firing the second laser without the first ablation pulse. The middle spectrum corresponds to single laser pulse ablation. The top spectrum corresponds to application of the two laser pulses separated by ~1 μs; emission is enhanced by additional heating of laser plasma. All data recorded is from accumulating 100 spectra.

Figure 25:
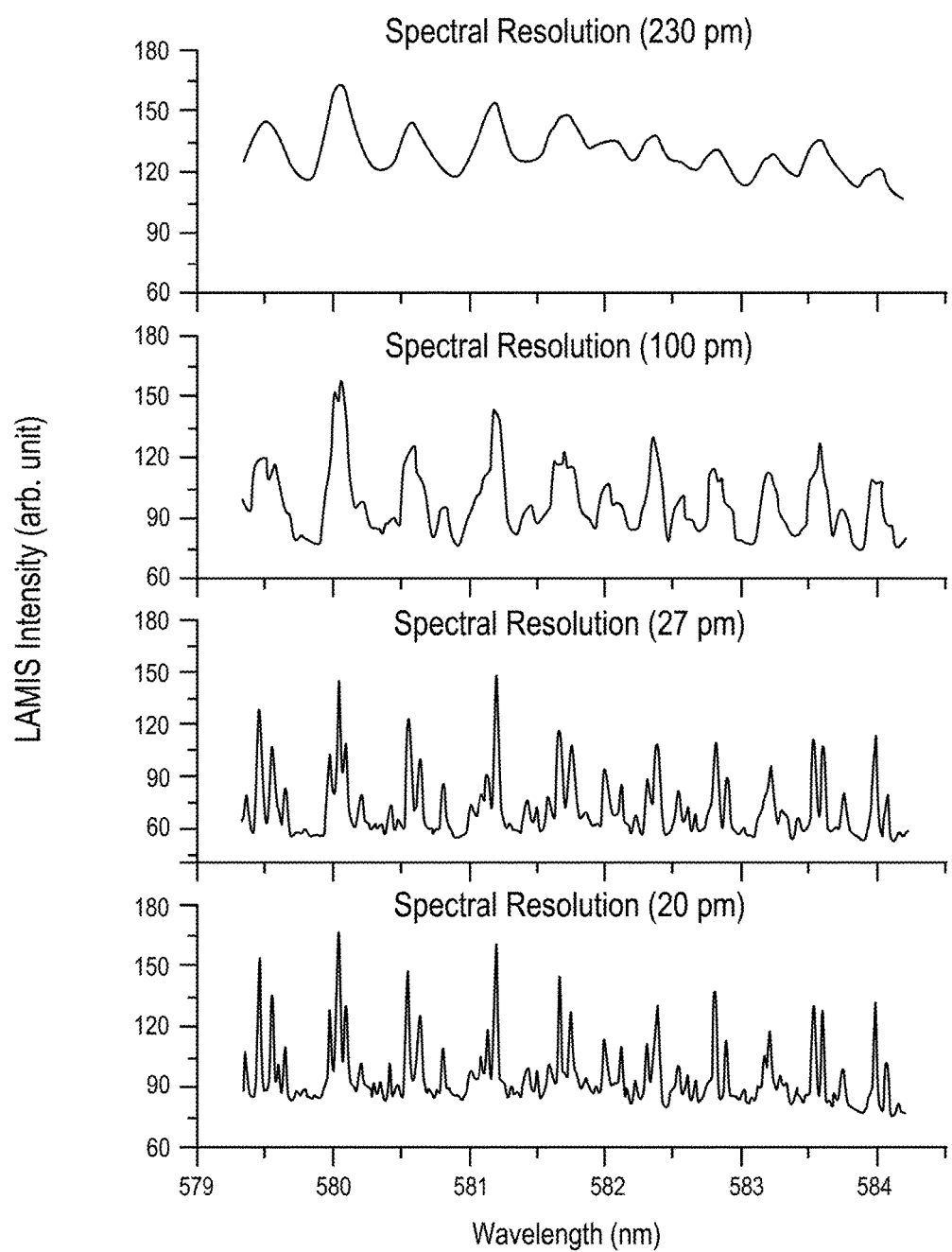

The large isotopic spectral shift in molecular transitions observed in this experiment relaxed requirements on resolution of the spectrometer. In order to investigate the effect of spectral resolution, the resolution of the spectrometer used with was varied from 20 pm to 230 pm, as shown in FIG. 25. FIG. 25 shows BO emission spectra from laser ablation of BN sample measured with different spectral resolution (20 pm, 27 pm, 100 pm, and 230 pm), with delay of 4 ?s and gate width of 30 μs.

Figure 26:
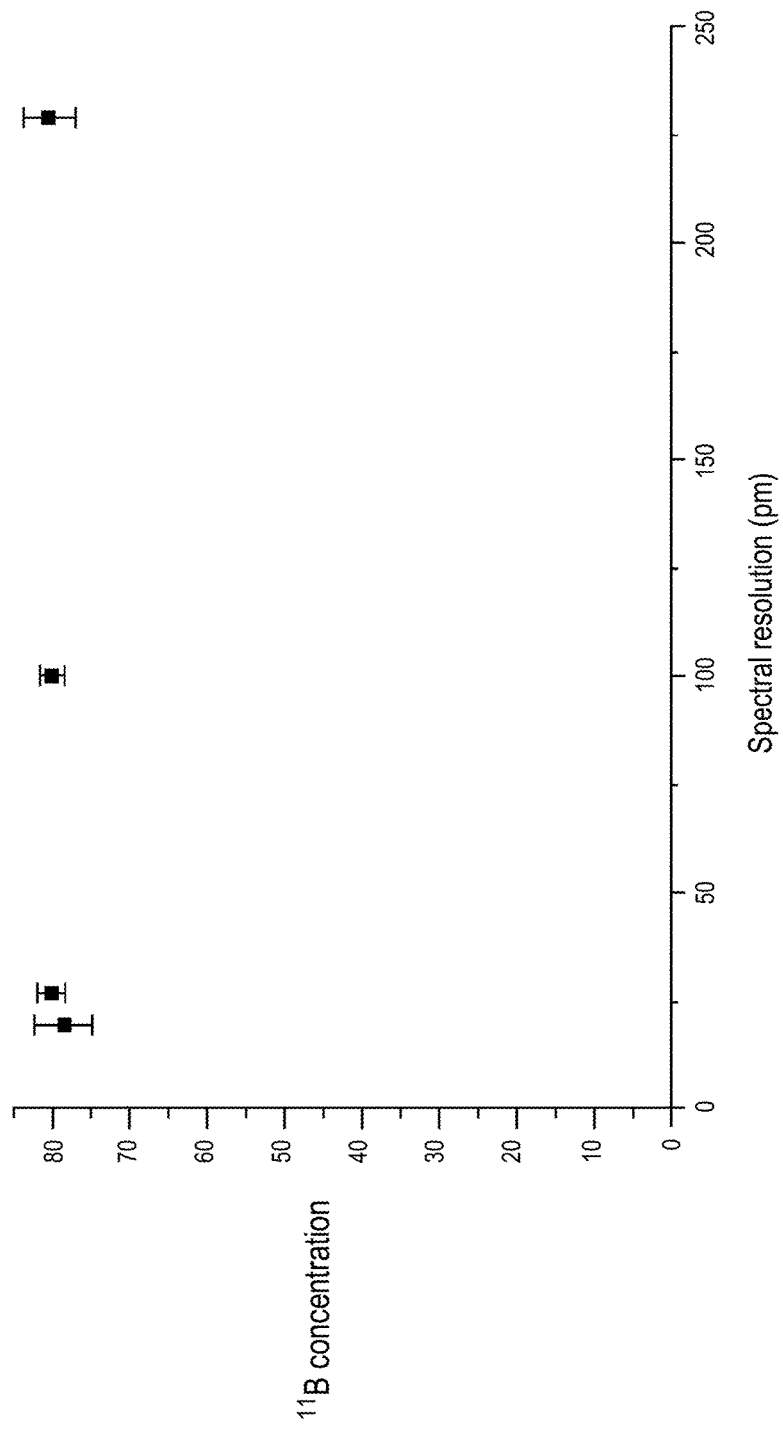

As shown in FIG. 26, calibration in accordance some embodiments (e.g., built using the same PLS routine as described earlier and established from the series of 100 single pulse spectra) did not change within an experimental standard relative deviation of ~3.5%. All data with varied resolution combined together resulted in a value of (79.6±2.8)% of $^{11}B$ isotope abundance in the BN sample, which is in agreement with the natural abundance range of 79.8% to 80.7%31. Therefore, high-resolution spectrometers may not be necessary for the quantitative measurements. The ability to measure isotope abundance with a low resolution spectrometer is a significant attribute of some embodiments. FIG. 26 shows the concentration of $^{11}B$ in the BN sample as predicted by PLS calibration versus spectral resolution of the recording spectrometer.

Example 3

In another experiment, laser energy was applied to vapors of ordinary water (H2O) and heavy water (D2O) and the OH and OD molecular emission from the plasma plume was measured. Molecular spectra in a laser-generated plasma became relatively stronger at long delays in the afterglow. The gate width of the ICCD detector was set to 60 μs with the delay of 25 μs, contrary to a usual value of ~1 μs typically used for atomic detection in LIBS measurements.

Figure 27:
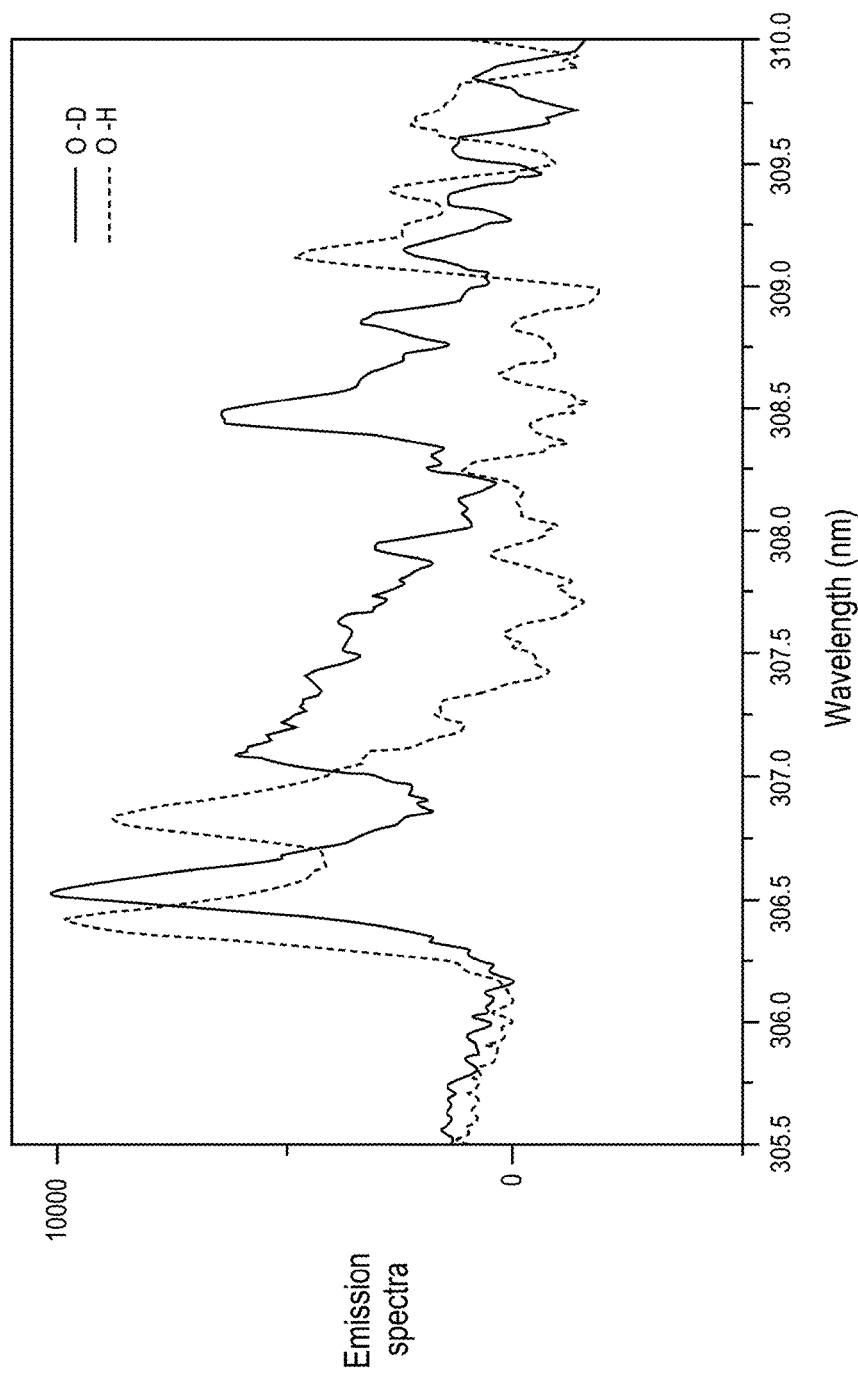
Figure 28:
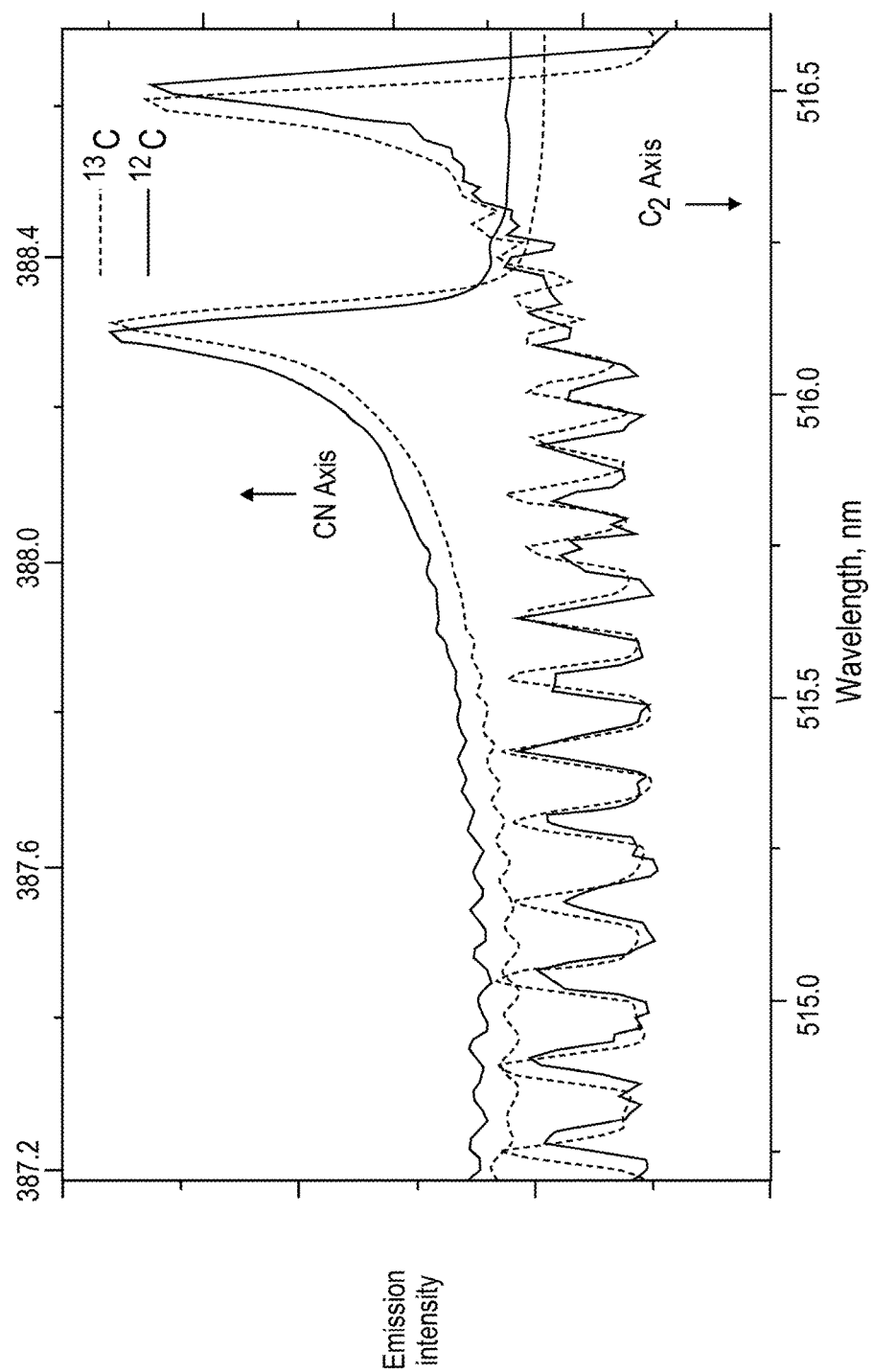
Figure 29:
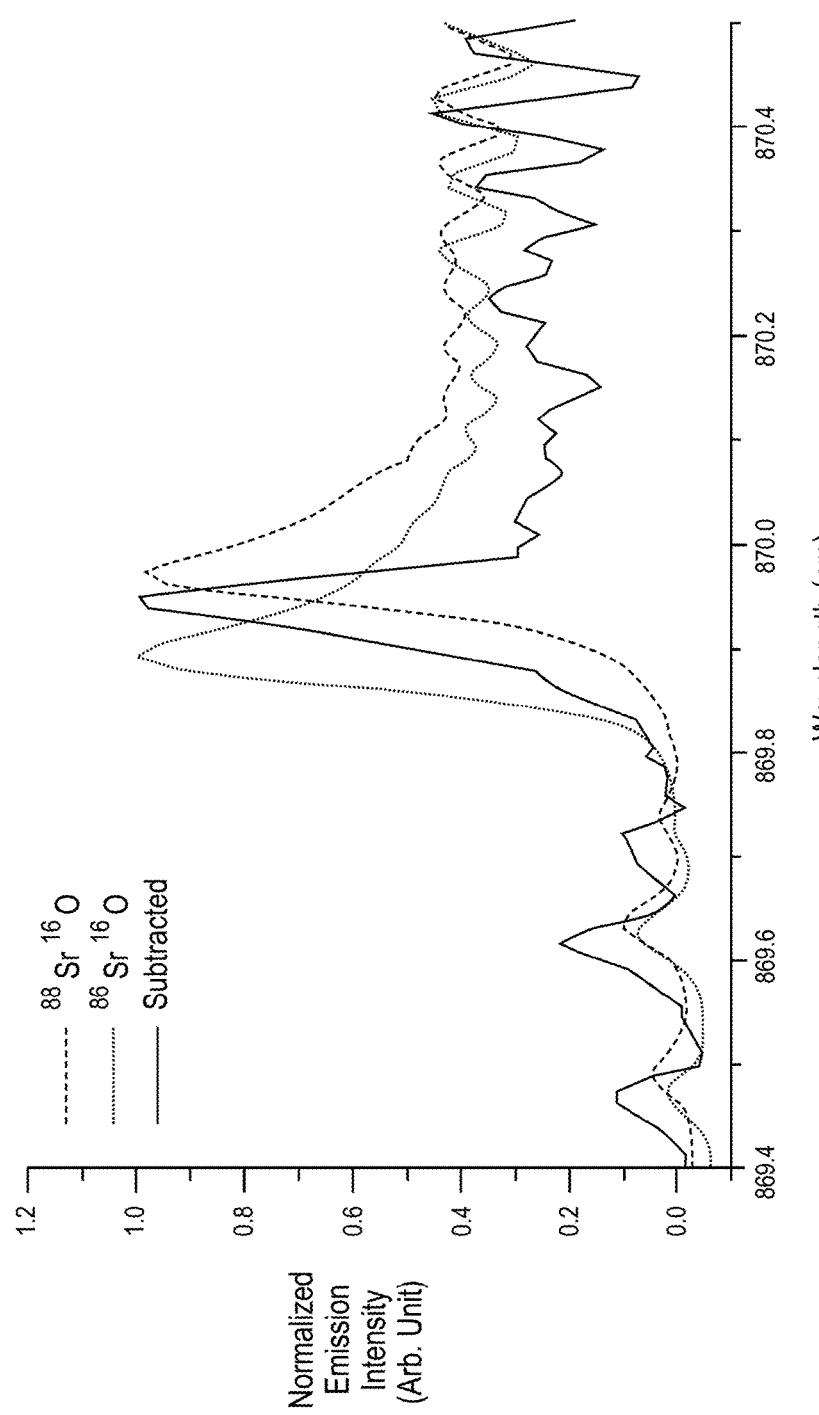
Figure 30A:
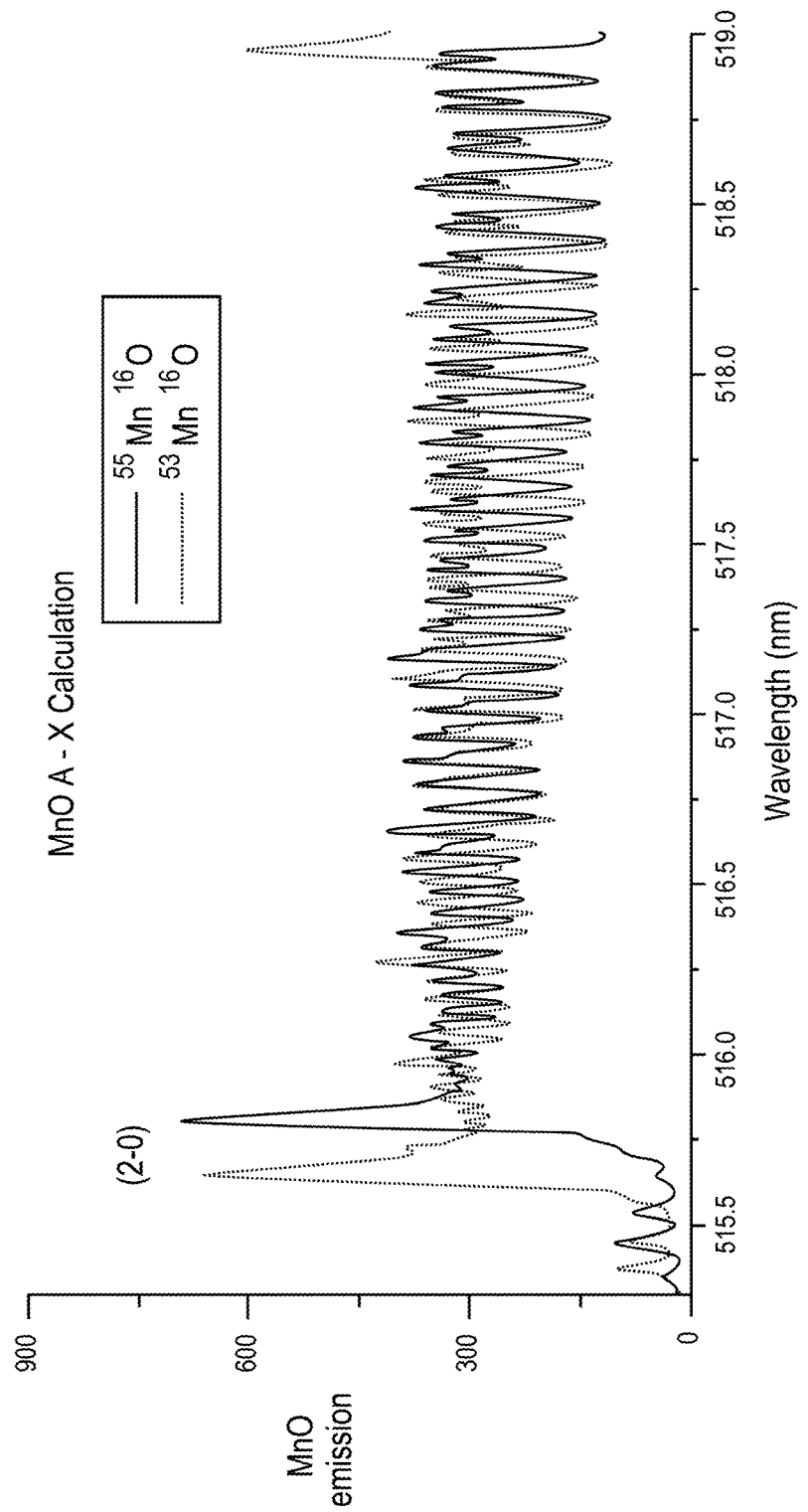
Figure 30B:
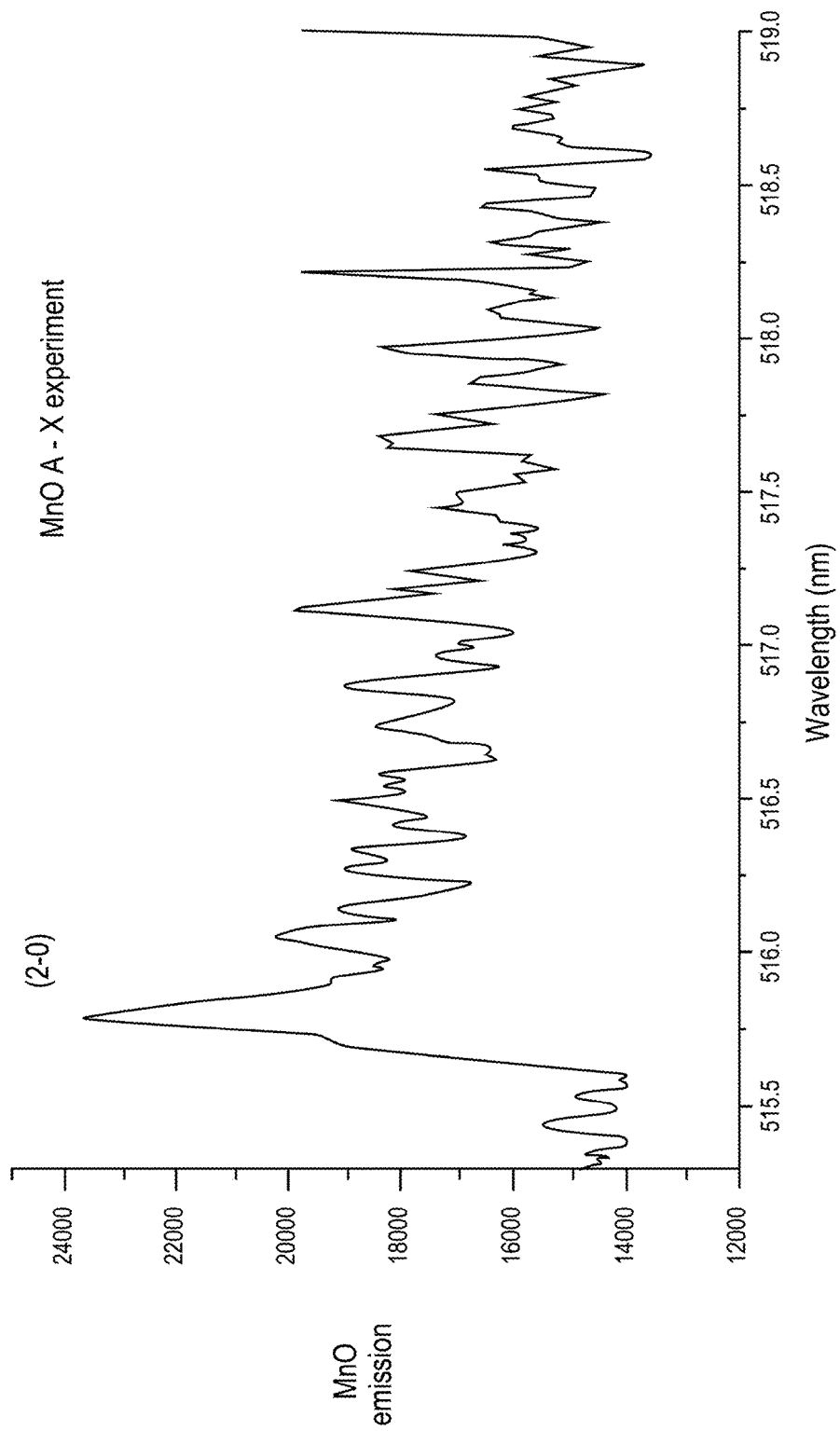

The data shown in FIG. 27 demonstrate the prominent spectral features of OH $A^2\Sigma+-X^2\Pi i$ (0,0) transition at ~306 nm ($R_1$, $R_2$ branch heads) and ~309 nm ($Q_2$ branch head) with partially resolved individual rotational lines. The experimental shift between the Q2 branch heads of OH and OD was approximately 0.68 nm. This shift was larger than the separation of 0.18 nm between H and D atomic lines at 656.29 nm and 656.11 nm, respectively. However, more important in this case was that the hydroxyl spectra were significantly less prone to Stark broadening than the atomic lines of H and D. Spectral lines of light atoms such as hydrogen and deuterium could be broadened up to ~1 nm width in laser ablation plasmas. Segregation of H and D has been measured in laser induced and DC arc plasmas. The possibility of segregation could influence these molecular spectral measurements, and needs to be investigated. However, at the long delay time and atmospheric pressure used in this work, multiple collisions between ablated and atmospheric species would likely equilibrate the spatial isotopic distribution. FIG. 27 shows the emission band of OH and OD generated from water and deuterium oxide, respectively, where the dashed curve represents the OH spectrum, while the solid curve represents the OD spectrum, with spectra accumulated from 600 laser pulses.

Simulation of the $^{16}OH$, $^{18}OH$, and $^{16}OD$ vibronic spectra demonstrated that sufficient spectral resolution (~0.03 nm) to selectively detect all these species simultaneously can be attained with modern compact echelle-based spectrometers. In laser ablation, the number density of species vaporized in each laser shot is usually $10^{15}$ cm$^{-3}$ to $10^{19}$ cm$^{-3}$. Most of the molecular species in a plume ejected from ice are expected to be $^{16}OH$. Following the isotopic abundances, a number of $^{18}OH$ radicals will be approximately 500 times less. Therefore, the estimated $^{18}OH$ number density of at least ~$10^{12}$ cm$^{-3}$ in a laser-vaporized plume from water/ice can be expected. Such quantities of species are readily detectable in emission spectroscopy. The real-time determination of oxygen isotopes from ice may be of significant consequence to studies in paleoclimatology, hydrogeology, and glaciology.

Example 4

In another experiment, carbon isotopic signatures were measured using diatomic CN and $C_2$ radicals that are known to form effectively in laser ablation plumes and are among the well-investigated species. The experiments were performed with regular graphite (99% $^{12}C$)) and isotopically enriched urea (99% $^{13}C$) as the samples. The $C_2$ from the sample and $N_2$ from ambient air are the precursors for CN formation in the laser ablation plasma. The CN radicals are generated in comparable abundance to $C_2$ and both these species are routinely observed in LIBS of carbon-containing samples. At near-threshold ablation of graphite, vapor in the plume is dominated by $C_2$ and $C_3$ radicals that are directly ejected as the intact molecules. Evaporation of carbon in the molecular versus atomic form is thermodynamically favored because of relatively high bond energies of $C_2$ and $C_3$. With the increasing laser fluence, molecular emission remains roughly constant while atomic carbon emission increases drastically indicating the major fraction of the plume becomes atomized.

The spectra of $C_2$ and CN with resolved features attributed to $^{12}C$ and $^{13}C$ isotopes as measured in laser ablation plasma are shown in FIG. 16. The data in FIG. 16 display the (0, 0) band head regions of the $C_2$ $d^3\Pi_g$–$a^3\Pi_u$ (Swan system) and CN $B^2\Sigma+-X^2\Sigma+$ transitions, respectively. The isotopic shifts in the band heads of both radicals were similar and approximately equal to ~0.03 nm. However, the heavier isotope spectrum in CN was shifted toward the violet, but the counterpart in $C_2$ was shifted toward the red. Simulation of the $C_2$ spectrum in the region 875 nm to 890 nm of the Phillips band (2, 0) of the electronic system $A^1\Pi_u$–$X^1\Sigma g+$ indicated that the isotopic shift between $^{12}C_2$ and $^{12}C^{13}C$ can be as large as ~0.3 nm. A similar conclusion was drawn from the simulation of $^{12}C^{14}N$ and $^{13}C^{14}N$ spectra in the region of the $A^2\Pi_i$–$X^2\Sigma+$ (1, 0) transition between 925 nm and 940 nm. In the latter wavelength region, the three isomeric molecules $^{12}C^{14}N$, $^{13}C^{14}N$, and $^{12}C^{15}N$ can be individually resolved with a resolution of ~0.03 nm. FIG. 16 shows the emission spectra of CN and $C_2$ generated from $^{13}C$-enriched urea and predominantly $^{12}C$ graphite.

Example 5

In another experiment, samples with known strontium isotopic content were ablated using a Nd:YAG laser with a wavelength of 1064 nm, a pulse duration of 4 ns, and an adjustable pulse energy within 50 mJ to 100 mJ. The laser beam was focused by a quartz lens on the sample surface to a spot diameter of ~100 pm. A second lens was used to collect the emission from the laser ablation plasma onto the entrance of a fiber optic cable coupled to one of the two Czerny-Turner spectrographs available for this work. An Acton SpectraPro SP2150 spectrograph with a 150 mm focal length and two exchangeable gratings was used for low resolution measurements. These two gratings (150 gr/mm and 600 gr/mm) provided spectral resolution of 5 nm and 1.3 nm, respectively. High resolution measurements were performed using a Horiba JY 1250M spectrograph with a 1250 mm focal length and a grating of 1200 gr/mm. The spectral resolution was 0.04 nm in the latter case.

Both spectrographs were equipped with an Intensified Charge-Coupled Device (ICCD) camera as a detector. The acquisition of spectra was delayed after the laser ablation pulse, and the delay time was varied to maximize intensity of molecular emission while minimizing emission from atoms and atomic ions. The data reported below represent measurements of spectra from a single or accumulated multiple laser pulses. All measurements were performed in air at atmospheric pressure.

Strontium carbonate and strontium halide powders were obtained from commercial sources, then mixed with 10% paraffin as a binder and pressed by a 7 ton press into one-centimeter diameter pellets. $SrCO_3$ powder (98% chemical purity) with natural isotopic abundance was obtained from Sigma-Aldrich Corporation. Isotope-enriched powders of $^{88}SrCO_3$ (99.75% enriched in $^{88}Sr$) and $^{86}SrCO_3$ (96.3% enriched in $^{86}Sr$) were obtained from Cambridge Isotope Laboratories, Inc. Other $SrCO_3$ powders included NIST Standard Reference Material (SRM 987) with the certified values of the atomic isotope fractions in percent: $^{88}Sr$=82.5845±0.0066; $^{87}Sr$=7.0015±0.0026; $^{86}Sr$=9.8566±0.0034; and $^{84}Sr$=0.5574±0.0015[35]. The values of the Sr isotopic percentage were used in this work for proportional subtraction of the SrO spectra.

In addition to $SrCO_3$, several strontium halides were utilized in this study to demonstrate that molecular spectra of different diatomic radicals can be used for isotopic analysis. Strontium halide powders of natural isotopic abundance included $SrF_2$ (Sigma-Aldrich, 98% purity), $SrCl_2$ (Alfa Aesar, 99.5% purity), $SrBr_2$ (Strem Chemicals, 99% purity), and $SrI_2$ (Alfa Aesar, 99.99% purity).

The isotope-enriched samples of $^{88}SrCO_3$ (99.75% enriched) and $^{86}SrCO_3$ (96.3% enriched) were ablated to generate spectra of $^{88}$SrO and $^{86}$SrO, respectively. The NIST isotopic standard SRM-987 was used to provide the summed spectra from all naturally occurring Sr isotopes with the certified atomic isotope percentages of $^{88}$Sr=82.58%, $^{87}$Sr=7.0%, $^{86}$Sr=9.86%, and $^{84}$Sr=0.56%. The spectra in FIG. 17 show unique and well resolved spectral signatures of $^{88}$SrO and $^{86}$SrO. The isotopic shifts of approximately 0.08 nm and 0.15 nm in the band heads of the (1,0) and (2,0) bands were determined from the measured data. These values agree well with the calculated isotopic shifts in the band origins of the SrO molecules.

The results of numerical subtraction of the isotope-enriched $^{88}$SrO and $^{86}$SrO spectra from the SrO spectrum of NIST SRM-987 sample of natural abundance are displayed in FIG. 17 for the (2,0) and (1,0) bands of the $A^1\Sigma^+ \rightarrow X^1\Sigma^+$ system, respectively. The strontium atomic isotope fractions certified for the SRM-987 sample were used as weight factors for this subtraction. The residual is the spectral contribution from $^{87}$SrO for the most part. Thus, the spectra of the three radicals $^{88}$SrO, $^{87}$SrO, and $^{86}$SrO were resolved. A rough estimation of the detection limit of some embodiments disclosed herein is below 1% for $^{87}$Sr.

Example 6

In another experiment, analyses were performed on samples of MnO. FIG. 18A shows calculations of $^{53}$MnO and $^{55}$MnO spectra. FIG. 18B shows experimental values of $^{55}$MnO as detected in the experiment.

Example 7

Isotopic shifts can be orders of magnitude larger in molecular than atomic spectra, as shown in FIG. 31. Atomic isotope shifts depend on the transition. The data in FIG. 31 represent prominent lines used in emission spectroscopy.

The effect of mass difference between isotopes is primarily observed in terms $G_v$ (vibrational energy) and $F_J$ (rotational energy) of vibronic transitions, while for the electronic component Te (electronic energy), the mass effect is significantly smaller. Consequently, molecular transitions involving change of vibrational and rotational states can exhibit significantly larger isotopic shifts than atomic transitions which are purely electronic in nature, as shown in FIG. 19. Larger isotopic shifts significantly simplify measurement requirements. Isotope ratio measurements from molecular spectra are particularly advantageous for light elements, as shown in FIG. 31. Light elements are important for biological organic life sciences. For heavy elements, the molecular isotopic effect is smaller because it scales with the reduced mass of the formed molecules. Moreover, the vibrational and rotational lines in heavy molecules are closer than in light molecules. FIG. 31 shows molecular vs. atomic isotopic shifts for various elements, where molecular shifts were calculated for either the diatomic oxide for each element considered in this plot and atomic isotopic shift values were taken from Stern et al. As shown in FIG. 31, isotopic shifts are much larger, up to several orders of magnitude, for molecular species as opposed to atomic species. The solid triangles in FIG. 31 denote experimental measurement data.

In the foregoing specification, various aspects are described with reference to specific embodiments, but those skilled in the art will recognize that further aspects are not limited thereto. Various features and aspects described above may be used individually or jointly. Other aspects of the invention, including alternatives, modifications, permutations and equivalents of the embodiments described herein, will be apparent to those skilled in the art from consideration of the specification, study of the drawings, and practice of the various aspects. Further, various aspects can be utilized in any number of environments and applications beyond those described herein without departing from the broader spirit and scope of the description. The written description and accompanying drawings are, accordingly, to be regarded as illustrative rather than restrictive.

Although various embodiments have been presented and explained using simplified examples, it will be understood that various changes and modifications are possible with regard to materials, shapes, and dimensions, without departure from the scope of the patent claims. The embodiments and preferred features described above should be considered exemplary, with the invention being defined by the appended claims, which therefore include all such alternatives, modifications, permutations and equivalents as fall within the true spirit and scope of the present disclosure.

What is claimed is:

1. A method for analyzing the composition of a sample using laser ablation spectroscopy, comprising:
    placing a sample on a stage being operable to move in x and y directions of a plane and in a z (height) direction perpendicular to the plane and moving said stage in said respective x and y and z directions,
    automatically maintaining an optimum height of a first sample site on the sample surface while ablating material from the first sample site into a first luminous plasma plume; and automatically maintaining the optimum height of a second sample site while ablating material from the second sample site into a second luminous plasma plume,
        wherein the optimum height is automatically maintained with a stage position controller operable to automatically adjust a height of the stage using a displacement signal proportional to a difference of height of the first sample site relative to a height of the second sample site, and the displacement signal is generated by a position sensor operable to sense the difference of height,
    waiting a preselected interval of time after the start of each ablation wherein an intensity of spectral features emanating from a molecular species increases during the preselected interval and an intensity spectral features emanating from atomic and/or ionic species decreases during the preselected time interval,
    gathering light emanating from each luminous plasma plume after the preselected time interval, and
    quantifying an abundance of isotopes of an element at each sample site based on the intensity of the spectral features from molecular species,
    wherein the quantifying comprises:
        generating a simulated spectrum of the molecular species using a mathematical model,
        performing a numerical fitting of the simulated spectrum of the molecular species to the molecular spectral features, and
        determining the abundance of the isotopes of the element at each sample site from the result of the numerical fitting.

2. The method of claim 1, wherein a pulsable laser is used to perform the ablation and produce the luminous plasma plume.

3. The method of claim 1 wherein the position sensor comprises a triangulation laser, and the stage position control controller comprises an array of motors operable to move the stage a predetermined amount.

4. The method of claim 1, wherein the position sensor displacement signal depends on a laser triangulation of the sample site.

5. The method of claim 1 wherein the triangulation laser provides a visible targeting marker on the first sample site and a visible targeting marker on the second sample site.

6. The method of claim 1, wherein the light is gathered using a detector that is insensitive to light during the preselected time interval, and is switched on to receive the light during another different time interval.

7. The method of claim 6, wherein the switching is performed with an electronically gateable device.

8. The method of claim 1, wherein an isotope concentration of 20 parts per million or less in the sample is determined.

9. The method of claim 1, wherein the sample and the sample stage are at atmospheric pressure.

10. The method of claim 1 wherein the sample and the sample stage are in ambient air under atmospheric conditions.

11. The method of claim 1 wherein material from a sample site is ablated with a laser pulse directed at a first angle with respect to the sample site and another laser pulse directed at a different angle with respect to the sample site is used to impart additional energy to the plasma plume.

12. A method for analyzing a composition of a sample using laser ablation spectroscopy, comprising:
　placing a sample on a stage being operable to move in x and y directions of a plane and in a z direction perpendicular to the plane,
　automatically maintaining a z-coordinate of a first sample site on the sample surface while ablating material from the first sample site into a first luminous plasma plume; and automatically maintaining a z-coordinate of a second sample site while ablating material from the second sample site into a second luminous plasma plume using a controller operable to automatically adjust a z-coordinate of the sample using a displacement signal proportional to a difference of a z-coordinate of the first sample site relative to a z-coordinate of the second sample site,
　waiting a preselected interval of time after the start of each ablation wherein an intensity of spectral features emanating from a molecular species increases during the preselected interval and an intensity spectral features emanating from atomic and/or an ionic species decreases during the interval,
　gathering light emanating from each luminous plasma plume after the preselected time interval, and
　quantifying an abundance of isotopes of an element at each sample site based on the intensity of the spectral features from molecular species,
　wherein the quantifying comprises:
　　generating a simulated spectrum of the molecular species using a mathematical model,
　　performing a numerical fitting of the simulated spectrum of the molecular species to the molecular spectral features, and
　　determining the abundance of the isotopes of the element at each sample site from the result of the numerical fitting.

13. The method of claim 12 further comprising ablating a multiplicity of distinct sample sites distributed throughout the surface of the sample with a laser beam having a preselected spot size in the range of approximately 50 micrometers to 500 micrometers and using spectral features from the sample sites to form a chemical map of the surface having a lateral resolution of the preselected spot size.

14. The method of claim 12 wherein the ablation of each sample site is performed with a laser beam having a preselected spot size in the range of approximately 50 micrometers to 500 micrometers.

15. The method of claim 12 further comprising ablating a multiplicity of distinct sample sites on the surface of the sample and using spectral features from the sample sites to effectuate a chemical map of the surface.

16. The method of claim 12 further comprising ablating a multiplicity of distinct sample sites distributed throughout the surface of the sample with a laser beam having a preselected spot size in the range of approximately 50 micrometers to 500 micrometers and using spectral features from the sample sites to form a chemical map of the surface having a lateral resolution of the preselected spot size.

17. The method of claim 12, wherein the preselected time interval depends on a wavelength, a duration, and/or a fluence of an ablation laser pulse.

18. A method for analyzing a composition of a sample using an interdependent combination of inductively coupled plasma mass spectrometry and laser ablation spectroscopy, the method comprising:
　placing a sample on a stage being operable to move in x and y directions of a plane and in a z (height) direction perpendicular to the plane and moving said stage in said respective x and y directions;
　automatically maintaining an optimum height of a first sample site on the sample surface while ablating material from the first sample site into a first luminous plasma plume with a laser pulse, and automatically maintaining an optimum height of a second sample site while ablating material from the second sample site into a second luminous plasma plume with another laser pulse, wherein the optimum height of the first sample site and second sample site is maintained using a stage position controller operable to automatically adjust a height of the stage based on a displacement signal proportional to a difference in height of the first sample site relative to a height of the second sample site;
　gathering light emanating from each luminous plasma plume into a fiber optic lightguide;
　coupling a portion of the gathered light from each luminous plasma plume into a spectrometer having wavelength separations means and a detector operable to be made insensitive to light during one time interval and switched on to receive light during a different time interval;
　receiving spectral data for each plasma plume, comprising wavelength and intensity values from the spectrometer, in a computer;
　sensing a pulse to pulse difference in an amount of ablated material based on a signal level obtained from the spectral data;
　transporting a gaseous portion of the ablated material to an inductively coupled plasma mass spectrometer;
　receiving ion mass to charge peak intensity values from the inductively coupled plasma mass spectrometer in the computer;
　correcting the ion mass to charge peak intensity values based on the sensed pulse to pulse difference in amount of ablated material; and using the corrected ion mass to charge peak intensity values to determine an abundance of elements at each sample site;

whereby inductively coupled plasma mass spectrometry and laser ablation spectroscopy are used cooperatively to obtain a sample composition comprising an abundance of elements at each sample site.

19. The method of claim 18, wherein analyzing the sample composition further includes using spectral data emanating from a molecular species to determine an abundance of isotopes of an element at each sample site, the method further comprising:

making the detector insensitive to light during a preselected time interval beginning at the start of each laser pulse, wherein intensities of spectral features emanating from the molecular species increase during the preselected time interval, and intensities of spectral features emanating from atomic and/or ionic species decrease during the preselected time interval;

switching the detector on immediately after the preselected time interval;

receiving spectral data for each plasma plume of light entering the spectrometer after the preselected time interval, in the computer;

generating a simulated spectrum for each molecular species with a mathematical model, and numerically fitting a combination of simulated spectra to the spectral data emanating from the molecular species;

whereby the abundance of the isotopes of each element at each sample site is quantified based on the numerical fitting.

20. The method of claim 18 wherein material from a sample site is ablated with a laser pulse directed at a first angle with respect to the sample site and another laser pulse directed at a different angle with respect to the sample site is used to impart additional energy to the plasma plume.

* * * * *